US009062126B2

(12) United States Patent
Zankel et al.

(10) Patent No.: US 9,062,126 B2
(45) Date of Patent: *Jun. 23, 2015

(54) COMPOSITIONS COMPRISING RECEPTOR-ASSOCIATED PROTEIN (RAP) VARIANTS SPECIFIC FOR CR-CONTAINING PROTEINS AND USES THEREOF

(75) Inventors: Todd C. Zankel, San Francisco, CA (US); Christopher M. Starr, Sonoma, CA (US)

(73) Assignee: RAPTOR PHARMACEUTICALS INC., Novato, CA (US)

( * ) Notice: Subject to any disclaimer, the term of this patent is extended or adjusted under 35 U.S.C. 154(b) by 1104 days.

This patent is subject to a terminal disclaimer.

(21) Appl. No.: 11/576,502

(22) PCT Filed: Sep. 18, 2006

(86) PCT No.: PCT/US2006/036453
§ 371 (c)(1),
(2), (4) Date: Jan. 4, 2008

(87) PCT Pub. No.: WO2007/035716
PCT Pub. Date: Mar. 29, 2007

(65) Prior Publication Data
US 2009/0281024 A1   Nov. 12, 2009

Related U.S. Application Data

(60) Provisional application No. 60/717,776, filed on Sep. 16, 2005, provisional application No. 60/813,954, filed on Jun. 14, 2006.

(51) Int. Cl.
| | |
|---|---|
| *A61K 38/16* | (2006.01) |
| *A61K 47/42* | (2006.01) |
| *C07K 14/47* | (2006.01) |
| *C07K 14/705* | (2006.01) |
| *A61K 47/48* | (2006.01) |
| *A61K 38/17* | (2006.01) |

(52) U.S. Cl.
CPC ......... *C07K 14/705* (2013.01); *A61K 47/48246* (2013.01); *C07K 14/47* (2013.01); *A61K 38/1709* (2013.01)

(58) Field of Classification Search
CPC ... C07K 14/705; A61K 38/1709; A61K 38/16
See application file for complete search history.

(56) References Cited

U.S. PATENT DOCUMENTS

| 5,474,766 A | 12/1995 | Schwartz et al. |
| 6,447,775 B1 | 9/2002 | Strickland et al. |
| 2006/0029586 A1 | 2/2006 | Chen et al. |

FOREIGN PATENT DOCUMENTS

WO   WO 00/71714 A2 * 11/2000

OTHER PUBLICATIONS

Migliorini et al. Allosteric modulation of ligand binding to low-density lipoprotein receptor-related protein by the receptor-associated protein requires critical lysine residues within its carboxyl-terminal domain. J Biol Chem. May 2003; 278(20): 17986-17992.*
Van Leuven F et al. Analysis of the human LRPAP1 gene coding for the lipoprotein receptor-associated protein: Identification of 22 polymorphisms and one mutation. Genomics, 1998; 52:145-151.*
Davies J (2003) The cyclization of peptides and depsipeptides. J. Peptide Sci. 9:471-501.*
Allinson et al., ADAMs family members as amyloid precursor protein alpha-secretases. *J. Neurosci. Res.* 74: 342-52 (2003).
Amour et al., The in vitro activity of ADAM-10 is inhibited by TIMP-1 and TIMP-3, *FEBS Lett.* 473: 275-9 (2000).
Andersen et al., Analysis of a two-domain binding site for the urokinase-type plasminogen activator—plasminogen activator inhibitor-1 complex in low-density-lipoprotein-receptor-related protein *Biochem. J.* 357: 289-96 (2001).
Andersen et al., Ca2+ binding to complement-type repeat domains 5 and 6 from the low-density lipoprotein receptor-related protein. *BMC Biochem.* 4, 7, (2003).
Andersen et al., Specific Binding of α-Macroglobulin to Complement-Type Repeat CR4 of the Low-Density Lipoprotein Receptor-Related Protein. *Biochemistry*, 39:10627-33 (2000).
Anderson et al., Dominant Thermodynamic Role of the Third Independent Receptor Binding Site in the Receptor-Associated Protein RAP. *Biochemistry*, 40: 15408-17 (2001).
Anderson et al., Identification of the minimal functional unit in the low density lipoprotein receptor-related protein for binding the receptor-associated protein (RAP). *J. Biol. Chem.* 275: 21017-24 (2000).
Ashcom et al., The human α2-kD cell surface glycoprotein specific for the activated conformation of α2-macroglobulin. *J. Cell Biol.* 110: 1041-8 (1990).
Bard et al., Peripherally administered antibodies against amyloid beta-peptide enter the central nervous system and reduce pathology in a mouse model of Alzheimer disease. *Nat. Med.* 6: 916-9 (2000).
Basu et al., CD91 is a common receptor for heat shock proteins gp96, hsp90, hsp70, and calreticulin. *Immunity*, 14: 303-13 (2001).
Benchenane et al., Tissue-Type Plasminogen Activator Crosses the Intact Blood-Brain Barrier by Low-Density Lipoprotein Receptor-Related Protein-Mediated Transcytosis. *Circulation*, 111, 2241-9 (2005).
Benjannet et al., α1-Antitrypsin Portland Inhibits Processing of Precursors Mediated by Proprotein Convertases Primarily within the Constitutive Secretory Pathway. *J. Biol. Chem.* 272: 26210-8 (1997).
Bickel et al., Delivery of peptides and proteins through the blood-brain barrier. *Adv Drug Deliv Rev.* 46: 247-79 (2001).
Bogan et al., Anatomy of hot spots in protein interfaces. *J. Mol. Biol.* 280: 1-9 (1998).
Bosshart et al., The cytoplasmic domain mediates localization of furin to the trans-Golgi network en route to the endosomal/lysosomal system. J. Cell Biol. 126: 1157-72 (1994).
Boucher et al., LRP: Role in Vascular Wall Integrity and Protection from Atherosclerosis. *Science*, 300: 329-32 (2003).
Bu et al., The roles of receptor-associated protein (RAP) as a molecular chaperone for members of the LDL receptor family. Int. Rev. Cytol. 209: 79-116 (2001).

(Continued)

*Primary Examiner* — Kimberly A Ballard
(74) *Attorney, Agent, or Firm* — Marshall, Gerstein & Borun LLP

(57) ABSTRACT

The present invention relates generally to receptor-selective variants of the low-density lipoprotein receptor-associated protein (RAP) and compositions thereof, methods of generating such variants and methods of using such receptor-selective RAP variant compositions for therapeutic purposes.

47 Claims, 20 Drawing Sheets

(56) References Cited

OTHER PUBLICATIONS

Cam et al., The Low Density Lipoprotein Receptor-related Protein 1B Retains β-Amyloid Precursor Protein at the Cell Surface and Reduces Amyloid-β Peptide Production. J. Biol. Chem. 279: 29639-46 (2004).
Casas et al., Massive CA 1/2 neuronal loss with intraneuronal and N-terminal truncated Aβ42 accumulation in a novel Alzheimer transgenic modal. Am. J. Pathol. 165: 1289-300 (2004).
Christensen et al., Megalin and cubilin: Synergistic endocytic receptors in renal proximal tubule. Am. J. Physiol. Renal Physiol. 280: F562-73 (2001).
Clackson et al., A hot spot of binding energy in a hormone-receptor interface. Science, 267: 383-6 (1995).
Deane et al., LRP/Amyloid β-Peptide Interaction Mediates Differential Brain Efflux of Aβ Isoforms. Neuron, 43: 333-44 (2004).
Dehouck et al., A New Function for the LDL Receptor: Transcytosis of LDL across the Blood-Brain Barrier. J. Cell Biol. 138: 877-89 (1997).
DeLano et al., Unraveling hot spots in binding interfaces: progress and challenges. Curr. Opin. Struct. Biol. 12: 14-20 (2002).
Dolmer et al., Characterization of the Calcium Site in Two Complement-like Domains from the Low-Density Lipoprotein Receptor-Related Protein (LRP) and Comparison with a Repeat from the Low-Density Lipoprotein Receptor. Biochemistry, 37: 17016-23 (1998).
Dolmer et al., NMR Solution Structure of Complement-like Repeat CR3 from the Low Density Lipoprotein Receptor-related Protein. J. Biol. Chem. 275: 3264-9 (2000).
Dwyer et al., High Affinity RNase S-Peptide Variants Obtained by Phage Display Have a Novel "Hot-Spot" of Binding Energy. Biochemistry, 40: 13491-500 (2001).
Fahrenholz et al., alpha-Secretase Activity of the Disintegrin Metalloprotease ADAM 10: Influences of Domain Structure. Ann. NY Acad. Sci. 920: 215-22 (2000).
Fillebeen et al., Receptor-mediated Transcytosis of Lactoferrin through the Blood-Brain Barrier. J. Biol. Chem. 274: 7011-7 (1999).
Fisher et al., Structure of an LDLR-RAP complex reveals a general mode for ligand recognition by lipoprotein receptors. Mol. Cell, 22: 277-83 (2006).
Furukawa et al., Increased activity-regulating and neuroprotective efficacy of alpha-secretase-derived amyloid precursor protein conferred by a C-terminal heparin-binding domain. J. Neurochem. 67: 1882-96 (1996).
Galkin et al., CVS-3983, a selective matriptase inhibitor, suppresses the growth of androgen independent prostate tumor xenografts. Prostate, 61: 228-35 (2004).
Gao et al., Structure-based method for analyzing protein-protein interfaces. J. Mol. Model (Online), 10: 44-54 (2004).
GenBank accession No. O75074, RecName: Full=Low-density lipoprotein receptor-related protein 3; Short=hLRp105; Flags: Precursor, Dec. 15, 2009.
GenBank accession No. O75096, RecName: Full=Low-density lipoprotein receptor-related protein 4; AltName: Full=Multiple epidermal growth factor-like domains 7; Flags: Precursor, Dec. 15, 2009.
GenBank accession No. O75197, RecName: Full=Low-density lipoprotein receptor-related protein 5; Flags: Precursor, Dec. 15, 2009.
GenBank accession No. O75581, RecName: Full=Low-density lipoprotein receptor-related protein 6; Flags: Precursor, Dec. 15, 2009.
GenBank accession No. P01130, RecName: Full=Low-density lipoprotein receptor; Short-LDL receptor; Flags: Precursor, Dec. 15, 2009.
GenBank accession No. P30533, RecName: Full=Alpha-2-macroglobulin receptor-associated protein; Short=Alpha-2-MRAP; AltName: Full-Low density lipoprotein receptor-related protein-associated protein 1; Short=RAP; Flags: Precursor, Dec. 15, 2009.
GenBank accession No. P57727, RecName: Full=Transmembrane protease, serine 3; AltName: Full=Tumor-associated differentially-expressed gene 12 protein; AltName: Full=Serine protease TADG-12, Dec. 15, 2009.
GenBank accession No. P98155, RecName: Full=Very low-density lipoprotein receptor; Short=VLDL receptor; Short=VLDL-R; Flags: Precursor, Dec. 15, 2009.
GenBank accession No. P98157, RecName: Full-Low-density lipoprotein receptor-related protein 1; Short=LRP; AltName: Full=Alpha-2-macroglobulin receptor; Short=A2MR; Flags: Precursor, Nov. 24, 2009.
GenBank accession No. P98164, RecName: Full=Low-density lipoprotein receptor-related protein 2; AltName: Full=Megalin; AltName: Full=Glycoprotein 330; Short=gp330; Flags: Precursor, Dec. 15, 2009.
GenBank accession No. PF06401, C. elegans protein C15C8.4, confirmed by transcript evidence [Caenorhabditis elegans], Nov. 30, 2009.
GenBank accession No. Q07954, RecName: Full=Prolow-density lipoprotein receptor-related protein 1; Short=LRP; AltName: Full=Alpha-2-macroglobulin receptor; Short=A2MR; AltName: Full=Apolipoprotein E receptor; Short=APOER; AltName: CD_antigen=CD91; Contains: RecName: Full=Low-density lipoprotein receptor-related protein 1 85 kDa subunit, Dec. 15, 2009.
GenBank accession No. Q14114, RecName: Full=Low-density lipoprotein receptor-related protein 8; AltName: Full=Apolipoprotein E receptor 2; Flags: Precursor, Dec. 15, 2009.
GenBank accession No. Q6PJ72, Hypothetical protein, Oct. 31, 2006.
GenBank accession No. Q7RTY8, RecName: Full=Transmembrane protease, serine 7; AltName: Full=Matriptase-3, Dec. 15, 2009.
GenBank accession No. Q7Z4F1, RecName: Full=Low-density lipoprotein receptor-related protein 10; Flags: Precursor, Dec. 15, 2009.
GenBank accession No. Q86VZ4, RecName: Full=Low-density lipoprotein receptor-related protein 11; Flags: Precursor, Dec. 15, 2009.
GenBank accession No. Q86YD5, RecName: Full=Low-density lipoprotein receptor class A domain-containing protein 3; Flags: Precursor, Dec. 15, 2009.
GenBank accession No. Q8IU80, RecName: Full=Transmembrane protease, serine 6; AltName: Full=Matriptase-2, Nov. 24, 2009.
GenBank accession No. Q8IZR7, Corin, Oct. 31, 2006.
GenBank accession No. Q8NAN7, CDNA FLJ35062 fis, clone OCBBF2019195, highly similar to Very Low-Density Lipoprotein Receptor (Very low density lipoprotein receptor), Oct. 31, 2006.
GenBank accession No. Q8WVC1, ST14 protein, dated Oct. 31, 2006.
GenBank accession No. Q8ww88, CFI protein, Oct. 31, 2006.
GenBank accession No. Q92673, RecName: Full=Sortilin-related receptor; AltName: Full=Sorting protein-related receptor containing LDLR class A repeats; Short=SorLA; AltName: Full=SorLA-1; AltName: Full=Low-density lipoprotein receptor relative with 11 ligand-binding repeats; Short=LDLR relative with 11 ligand-binding repeats; Short-LR11, Dec. 15, 2009.
GenBank accession No. Q96NT6, CDNA FLJ30101 fis, clone BNGH41000118, highly similar to Homo sapiens low density lipoprotein receptor related protein-deleted in tumor (LRPDIT) mRNA, Oct. 31, 2006.
GenBank accession No. Q9BYE1, RecName: Full=Transmembrane protease, serine 13; AltName: Full=Membrane-type mosaic serine protease; Short=Mosaic serine protease, Dec. 15, 2009.
GenBank accession No. Q9BYE2, RecName: Full=Transmembrane protease, serine 13; AltName: Full=Membrane-type mosaic serine protease; Short=Mosaic serine protease, Dec. 15, 2009.
GenBank accession No. Q9NPFO, RecName: Full=CD320 antigen; AltName: Full=8D6 antigen; AltName: Full=FDC-signaling molecule 8D6; Short=FDC-SM-8D6; AltName: Full=Transcobalamin receptor; Short=TCbIR; AltName: CD_antigen=CD320; Flags: Precursor, Dec. 15, 2009.
GenBank accession No. Q9NRS4, RecName: Full=Transmembrane protease, serine 4; AltName: Full=Membrane-type serine protease 2; Short=MT-SP2, Dec. 15, 2009.
GenBank accession No. Q9NZR2, RecName: Full=Low-density lipoprotein receptor-related protein 1B; AltName: Full=Low-density lipoprotein receptor-related protein-deleted in tumor; Short=LRP-DIT; Flags: Precursor, Dec. 15, 2009.

(56) References Cited

OTHER PUBLICATIONS

GenBank accession No. Q9Y561, RecName: Full=Low-density lipoprotein receptor-related protein 12; AltName: Full=Suppressor of tumorigenicity protein 7; Flags: Precursor, Dec. 15, 2009.
GenBank accession No. X13916, Human mRNA for LDL-receptor related protein, Apr. 18, 1996.
GenBank accession No. Q7Z7K9, LRP1 protein, Oct. 31, 2006.
Gong et al., Alzheimer's disease-affected brain: Presence of oligomeric Aβ ligand (ADDLs) suggests a molecular basis for reversible memory loss. *Proc. Natl. Acad. Sci. USA*. 100: 10417-22 (2003).
Goudriaan et al., Protection from obesity in mice lacking the VLDL receptor. *Arterioscier. Thromb. Vasc. Biol.* 21: 1488-93 (2001).
Goudriaan et al., The VLDL receptor plays a major role in chylomicron metabolism by enhancing LPL-mediated triglyceride hydrolysis. *J. Lipid Res.* 45: 1475-81 (2004).
Hahn-Dantona et al., The Low Density Lipoprotein Receptor-related Protein Modulates Levels of Matrix Metalloproteinase 9 (MMP-9) by Mediating Its Cellular Catabolism. *J. Biol. Chem.* 276: 15498-603 (2001).
Halperin et al., Protein-protein interactions: Coupling of structurally conserved residues and of hot spots across interfaces. Implications for docking. *Structure*, 12: 1027-38 (2004).
Herz et al, Lipoprotein Receptors in the Nervous System. *Annu. Rev. Biochem.* 71: 405-34 (2002).
Herz et al., 39-kDa protein modulates binding of ligands to low density lipoprotein receptor-related protein/α2-macroglobulin receptor. *J. Biol. Chem.* 266: 21232-8 (1991).
Herz et al., Gene transfer and disruption strategies to elucidate hepatic lipoprotein receptor functions. *Atherosclerosis*, 118: S37-41 (1995).
Hickey et al., Apoptosis in Huntington's disease. *Prog. Neuropsychopharmacol. Biol. Psychiatry*, 27: 255-65 (2003).
Hiltunen et al., Expression of LDL receptor, VLDL receptor, LDL receptor-related protein, and scavenger receptor in rabbit atherosclerotic lesions: Marked induction of scavenger receptor and VLDL receptor expression during lesion development. *Circulation*, 97: 1079-86 (1998).
Hoang et al., Expression of LDL receptor-related protein 5 (LRP5) as a novel marker for disease progression in high-grade osteosarcoma. *Int. J. Cancer*, 109: 106-11 (2004).
Hoang et la., Gene Expression Profiling Identifies Matriptase Overexpression in Malignant Mesothelioma. *Chest*, 125: 1843-52 (2004).
Hoe et al., Multiple pathways of apolipoprotein E signaling in primary neurons. *J. Neurochem*,. 93: 145-55 (2005).
Holmen et al., Essential role of beta-satenin in postnatal bone acquisition. *J. Biol. Chem.* 280(22): 21162-8 (2005).
Horn et al., Molecular analysis of ligand binding to the second cluster of complement-type repeats of the low density lipoprotein receptor-related protein. *J. Biol. Chem.* 272: 13608-13 (1997).
Hsia et al., Plaque-independent disruption of neural circuits in Alzheimer's disease mouse models. *Proc. Natl. Acad. Sci. USA*. 96: 3228-33 (1999).
Hsieh et al., Mesd encodes an LRP5/6 chaperone essential for specification of mouse embryonic polarity. *Cell*, 112: 355-67 (2003).
Huang et al., NMR Solution Structure of Complement-like Repeat CR8 from the Low Density Lipoprotein Receptor-related Protein. *J. Biol. Chem.* 274: 14130-6 (1999).
Hung et al., Assembly of adherens junctions is required for sphingosine 1-phosphate-induced matriptase accumulation and activation at mammary epithelial cell-cell contacts. *Am J Physiol Cell Physiol*. 286: C1159-69 (2004).
Hussain et al., Characterication of the ectodomain shedding of the beta-site amyloid precursor protein-cleaving enzyme 1 (BACE1). *J. Biol. Chem.* 278: 36264-8 (2003).
Irie et al., Transendothelial transport of macromolecules: the concept of tissue-blood barriers. *Cell Biol Rev*. 25: 317-33, 340-1 (1991).
Jensen et al., Purification of the human placental alpha2-macroglobulin receptor. *FEBS Lett*. 255: 275-80 (1989).

Johnson et al., Possible role of matriptase in the diagnosis of ovarian cancer. *Expert Rev Mol Diagn*. 3: 331-8 (2003).
Kataoka et al., Role of cancer cell-stroma interaction in invasive growth of cancer cells. *Hum Cell*, 16: 1-14 (2003).
Kim et al., Gene Transfer into Human Hepatoma Cells by Receptor-Associated Protein/Polylysine Conjugates. *Bioconjugate Chem*. 15: 326-32 (2004).
Lee et al., Increased expression of matriptase is associated with histopathologic grades of cervical neoplasia. *Hum Pathol* 36: 626-33 (2005).
Li et al., Identification of a human follicular dendritic cell molecule that stimulates germinal center B cell growth. *J. Exp. Med.* 191: 1077-84 (2000).
Li et al., LRP6 expression promotes cancer cell proliferation and tumorigenesis by altering beta-catenin subcellular distribution. *Oncogene*, 23: 9129-35 (2004).
Li et al., Magnitude of the hydrophobic effect at central versus peripheral sites in protein-protein interfaces. *Structure*, 13: 297-307 (2005).
Li et al., Novel follicular dendritic cell molecule, 8D6, collaborates with CD44 in supporting lymphomagenesis by a Burkitt lymphoma cell line, L3055. *Blood*, 104: 815-21 (2004).
Lin et al., GDNF: A glial cell line-derived neurotrophic factor for midbrain dopaminergic neurons. *Science*, 260: 1130-2 (1993).
Lisi et al., Impaired thyroglobulin (Tg) secretion by FRTL-5 cells transfected with soluble receptor associated protein (RAP): Evidence for a role of RAP in the Tg biosynthetic pathway. *J. Endocrinol. Invest*. 26: 1105-10 (2003).
List et al., Deregulated matriptase causes ras-independent multistage carcinogenesis and promotes ras-mediated malignant transformation. *Genes Dev*. 19: 1934-50 (2005).
Lundgren et al., Tissue distribution of human ngp330/megalin, a putative Ca2+-sensing protein. *J. Histochem. Cytochem*. 45: 383-92 (1997).
Marino et al., Role of Megalin (gp330) in Transcytosis of Thyroglobulin by Thyroid Cells: A Novel Function in the Control of Thyroid Hormone Release. *J. Biol. Chem.* 275: 7125-37 (2000).
Martin et al., Involvement of the Neurotensin Receptor-3 in the Neurotensin-Induced Migration of Human Microglia. *J. Neurosci*. 23: 1198-205 (2003).
May et al., Integration of Endocytosis and Signal Transduction by Lipoprotein Receptors. *Sci STKE 2003*, PE12 (2003).
Mayer et al., Sorting of furin in polarized epithelial and endothelial cells: Expression beyond the Golgi Apparatus. *J. Histochem. Cytochem*. 52: 567-79 (2004).
Medved et al., Domain organization of the 39-kDa receptor-associated protein. *J. Biol.Chem*. 274(2): 717-27 (1999).
Meilinger et al., Removal of lactoferrin from plasma is mediated by binding to low density lipoprotein receptor-related protein/alpha2-macroglobulin receptor and transport to endosomes. *FEBS Lett*. 360: 70-4 (1995).
Melman et al., High affinity binding of receptor-associated protein to heparin and low density lipoprotein receptor-related protein requires similar basic amino acid sequence motifs. *J. Biol. Chem*. 276: 29338-46 (2001).
Meziane et al., Memory-enhancing effects of secreted forms of the beta-amyloid precursor protein in normal and amnestic mice. *Proc. Natl. Acad. Sci. USA*. 95: 12683-8 (1998).
Mikhailenko et al., Functional domains of the very low density lipoprotein receptor: Molecular analysis of ligand binding and acid-dependent ligand dissociate mechanisms. *J. Cell. Sci*. 112(Pt. 19): 3269-3281 (1999).
Mizuguchi et al., LRP5, low-density-lipoprotein-receptor-related protein 5, is a determinant for bone mineral density. *J. Hum. Genet*. 49: 80-6 (2004).
Moestrup et al., Megalin- and Cubilin-Mediated Endocytosis of Protein-Bound Vitamins, Lipids, and Hormones in Polarized Epithelia. *Annu Rev Nutr*. 21: 407-28 (2001).
Nagaike et al., Paradoxically enhanced immunoreactivity of hepatocyte growth factor activator inhibitor type 1 (HAI-1) in cancer cells at the invasion front. *Cancer Sci*. 95: 728-35 (2004).

(56) References Cited

OTHER PUBLICATIONS

Neels et al., Interaction Between Factor VIII and LDL Receptor-related Protein: Modulation of Coagulation? *Trends Cardiovasc Med.* 10: 8-14 (2000).

Neels et al., The second and fourth cluster of class A cysteine-rich repeats of the low density lipoprotein receptor-related protein share ligand-binding properties. *J. Biol. Chem.* 274: 31305-11 (1999).

Nielsen et al., The solution structure of the N-terminal domain of alpha2-macroglobulin receptor-associated protein. *Proc. Natl. Acad. Sci. USA.* 94: 7521-5 (1997).

Obermoeller et al., Differential functions of triplicated repeats suggest two independent roles for the receptor-associated protein as a molecular chaperone. *J. Biol. Chem.* 272: 10761-8 (1997).

Oberst et al., Expression of the Serine Protease Matriptase and Its Inhibitor HAI-1 in Epithelial Ovarian Cancer: Correlation with Clinical Outcome and Tumor Clinicopathological Parameters. *Clin Cancer Res.* 8: 1101-7 (2002).

Oberst et al., Matriptase and HAI-1 Are Expressed by Normal and Malignant Epithelial Cells in Vitro and in Vivo. *Am J Pathol.* 158: 1301-11 (2001).

Oberst et al., The Activation of Matriptase Requires Its Noncatalytic Domains, Serine Protease Domain, and Its Cognate Inhibitor. *J Biol Chem.* 278: 26773-9 (2003).

Obunike et al., Transcytosis of lipoprotein lipase across cultured endothelial cells requires both heparin sulfate proteoglycans and the very low density lipoprotein receptor. *J. Biol. Chem.* 276: 8934-41 (2001).

Olsen, Life without Perlecan Has Its Problems. *J. Cell Biol.* 147: 909-12 (1999).

Orlando et al., Functional domains of the receptor-associated protein (RAP). *Proc. Natl. Acad. Sci. USA.* 3161-3 (1994).

Orlando et al., Identification of the second cluster of ligand-binding repeats in megalin as a site for receptor-ligand interactions. *Proc. Natl. Acad. Sci. USA.* 94: 2368-73 (1997).

Pan et al., Efficient transfer of receptor-associated protein (RAP) across the blood-brain barrier. *J. Cell Sci.* (2004), 117 (Pt 21): 5071-8.

Pfistermueller et al., Preferential recognition of the very low-density lipoprotein receptor ligand binding site by antibodies from phage display libraries. *FEBS Lett.* 396: 14-20 (1996).

Postina et al., A disintegrin-metalloproteinase prevents amyloid plaque formation and hippocampal defects in an Alzheimer's disease mouse model. *J. Clin. Invest.* 113: 1456-64 (2004).

Prince et al., Lipoprotein Receptor Binding, Cellular Uptake, and Lysosomal Delivery of Fusions between the Receptor-associated Protein (RAP) and α-I-Iduronidase or Acid α-Glucosidase. *J. Biol. Chem.* 279: 35037-46 (2004).

Qiu et al., ApoE isoforms affect neuronal N-methyl-image-aspartate calcium responses and toxicity via receptor-mediated processes. *Neuroscience*, 122: 291-303 (2003).

Qu et al., Role of VLDL receptor in the process of foam cell formation. *J. Huazhong Univ. Sci. Technolog. Med. Sci.* 24: 1-4, 8 (2004).

Rall et al., The domain structure of human receptor-associated protein. *J. Biol. Chem.* 273(37): 24152-7 (1998).

Rohn et al., Bi-directional trafficking between the trans-Golgi network and the endosomal/lysosomal system. *J. Cell Sci.* 113(Pt.12): 2093-101 (2000).

Rudenko et al., Structure of the LDL Receptor Extracellular Domain at Endosomal pH *Science*, 298: 2353-8 (2002).

Santin et al., Gene expression profiles in primary ovarian serous papillary tumors and normal ovarian epithelium: Identification of candidate molecular markers for ovarian cancer diagnosis and therapy. *Int. J. Cancer*, 112: 14-25 (2004).

Santin et al., The novel serine protease tumor-associated differentially expressed gene-15 (Matriptase/MT-SP1) is highly overexpressed in cervical carcinoma. *Cancer*, 98: 1898-904 (2003).

Savonen et al., The carboxyl-terminal domain of receptor-associated protein facilitates protein folding and trafficking of the very low density lipoprotein receptor by interaction with the three amino-terminal ligand-binding repeats of the receptor. *J. Biol. Chem.* 274(36): 25877-82 (1999).

Schenk et al., Immunization with amyloid-beta attenuates Alzheimer-disease-like pathology in the PDAPP mouse. *Nature*, 400: 173-7 (1999).

Schmitz et al., Hippocampal neuron loss exceeds amyloid plaque load in a transgenic mouse model of Alzheimer's disease. *Am. J. Pathol.* 164: 1495-502 (2004).

Schneider et al., LDL receptor relatives at the crossroad of endocytosis and signaling. *Cell Mol Life Sci.* 60: 892-903 (2003).

Selkoe et al., Amyloid beta-protein and the genetics of Alzheimer's disease. *J. Biol. Chem.* 271: 18295-18298 (1996).

Shayo et al., The putative blood-brain barrier transporter for the β-amyloid binding protein apolipoprotein j is saturated at physiological concentrations. *Life Sci.* 60: PL115-8 (1997).

Sidhu et al., Phage display for selection of novel binding peptides. *Methods Enzymol.* 328: 333-63 (2000).

Simonovic et al., Calcium Coordination and pH Dependence of the Calcium Affinity of Ligand-Binding Repeat CR7 from the LRP. Comparison with Related Domains from the LRP and the LDL Receptor. *Biochemistry*, 40: 15127-34 (2001).

Srour et al., TACE/ADAM-17 maturation and activation of sheddase activity require proprotein convertase activity. *FEBS Lett.* 554: 275-83 (2003).

Suzuki et al., Inhibition of Tumor Invasion by Genomic Down-regulation of Matriptase through Suppression of Activation of Receptor-bound Pro-urokinase. *J Biol Chem.* 279: 14899-908 (2004).

Tacken et al., Living up to a name: the role of the VLDL receptor in lipid metabolism. *Curr. Opin. Lipidol.* 12: 275-9 (2001).

Takahashi et al., The very low density lipoprotein (VLDL) receptor—a peripheral lipoprotein receptor for remnant lipoproteins into fatty acid active tissues. *Mol. Cell. Biochem.* 248: 121-7 (2003).

Tanimoto et al., Ovarian Tumor Cells Express a Transmembrane Serine Protease: A Potential Candidate for Early Diagnosis and Therapeutic Intervention. *Tumour Biol.* 22: 104-14 (2001).

Tanimoto et al., Transmembrane serine protease TADG-15 (ST14/Matriptase/MT-SPI): Expression and prognostic value in ovarian cancer. *Br. J. Cancer*, 92: 278-83 (2005).

Thompson et al., CLUSTAL W: improving the sensitivity of progressive multiple sequence alignment through sequence weighting, position-specific gap penalties and weight matrix choice. *Nucleic Acids Res.* 22: 4673-80 (1994).

Tsai et al., Fibrillar amyloid deposition leads to local synaptic abnormalities and breakage of neuronal branches. *Nat. Neurosci.* 7: 1181-3 (2004).

Tsuzuki et al., Evidence for the occurrence of membrane-type serine protease 1/matriptase on the basolateral sides of enterocytes. *Biochem J* 388: 679-87 (2005).

Vash et al., Three Complement-Type Repeats of the Low-Density Lipoprotein Receptor-Related Protein Define a Common Binding Site for RAP, PAI-1, and Lactoferrin. *Blood*, 92: 3277-85 (1998).

Verdaguer et al., X-ray structure of a minor group human rhinovirus bound to a fragment of its cellular receptor protein. *Nat Struct Mol Biol.* 11: 429-34 (2004).

Wang et al., Role of Calcium in Protein Folding and Function of Tva, the Receptor of Subgroup A Avian Sarcoma and Leukosis Virus. *J. Virol.* 75: 2051-8 (2001).

Warshawsky et al., Binding analysis of amino-terminal and carboxyl-terminal regions of the 39-kDa protein to the low density lipoprotein receptor-related protein. *J. Biol. Chem.* 269: 3325-30 (1994).

Westerndorf et al., Wnt signaling in osteoblasts and bone diseases. *Gene*, 341: 19-39 (2004).

Williams et al., A novel mechanism for controlling the activity of alpha2-macroglobulin receptor/low density lipoprotein receptor-related protein. *J. Biol. Chem.* 267: 9035-40 (1992).

Wyne et al., Expression of the VLDL receptor in endothelial cells. *Arterioscler. Thromb. Vasc. Biol.* 16: 407-15 (1996).

Xia et al., Intramembrane proteolysis by presenilin and presenilin-like proteases. *J. Cell Sci.* 116: 2839-44 (2003).

(56) References Cited

OTHER PUBLICATIONS

Yagyu et al., Very low density lipoprotein (VLDL) receptor-deficient mice have deduced lipoprotein lipase activity. *J. Biol. Chem.* 277: 10037-43 (2002).

Zerbinatti et al., Increased soluble amyloid-beta peptide and memory deficits in amyloid model mice overexpressing the low-density lipoprotein receptor-related protein. *Proc. Natl. Acad. Sci. USA.* 101: 1075-80 (2004).

Zhang et al., The LRP5 high-bone-mass G171V mutation disrupts LRP5 interaction with Mesd. *Mol. Cell Biol.* 24: 4677-84 (2004).

Zheng et al., Organ distribution in rats of two members of the low-density lipoprotein receptor gene family, gp330 and LRP/alpa 2MR, and the receptor-associated protein (RAP). *J. Histochem. Cytochem.* 42: 531-42 (1994).

Zlokovic et al., Glycoprotein 330/megalin: Probable role in receptor-mediated transport of apolipoprotein J alone and in a complex with Alzheimer disease amyloid beta at the blood-brain and blood-cerebrospinal fluid barriers. *Proc. Natl. Acad. Sci. USA.* 93: 4229-34 (1996).

\* cited by examiner

FIGURE 2

| Name | Sequence | A | C | A' | C' | SEQ ID NO |
|---|---|---|---|---|---|---|
| | | A xcBxCxD | | | | |
| LRP1CR3 | RPQCQ-PGEFACANS--RCIQERW--KCDGDNDCLDNSDEAPALCHQHT------ | W | D | W | D | SEQ ID NO: 69 |
| LRP1CR4 | ---CP-SDRFKCENN--RCIPNRW--LCDGDNDCGNSEDESNATCSART------ | W | D | W | D | SEQ ID NO: 70 |
| LRP1CR5 | ---CP-PNQFSCASG--RCIP1SW--TCDLDDCGDRSDES-ASCAY--------- | | | | | SEQ ID NO: 71 |
| VLDLRCR6 | HTKCP-ASEIQCGSG--ECIHKKW--RCDGDPDCKDGSDEVNCPSRT-------- | W | D | R | I | SEQ ID NO: 72 |
| VLDLRCR7 | ---CR-PDQFECEDG--SCIHGSR--QCNGIRDCVDGSDEVNCKNVNQ------- | R | I | K | E | SEQ ID NO: 73 |
| VLDLRCR8 | ---CLGPGKFKCRSG--ECIDISK--VCNQEQDCRDWSDEPLKECHINE------ | | | | | SEQ ID NO: 74 |
| MATCR1 | ---PC--PGQFTCRTG--RCIRKEL--RCDGWADCTDHSDELNCS---------- | L | W | W | V | SEQ ID NO: 75 |
| MATCR2 | ---CDAGHQFTCKNK--FCKPLFW--VCDSVNDCGDNSDEQGCS---------- | W | V | Q | K | SEQ ID NO: 76 |
| MATCR3 | ---CP-AQTFRCSNG--KCLSKSQ--QCNGKDDCGDGSDEASCPKVNVVT----- | Q | K | P | K | SEQ ID NO: 77 |
| MATCR4 | ---CT-KHTYRCLNG--LCLSKGNPECDGKEDCSDGSDEKDCD----------- | | | | | SEQ ID NO: 78 |
| LRP2CR8 | PTEQCGLFSFPCKNG--RCVPNYY--LCDGVDDCHDNSDEQLCGTLNNT------ | Y | V | W | R | SEQ ID NO: 79 |
| LRP2CR9 | ---CS-SSAFTCGHG--ECIPAHW--RCDKRNDCVDGSDEHNCPTHAF------- | | | | | SEQ ID NO: 80 |
| LRP2CR27 | ---CR-LGQFQCSDG--NCTSPQT--LCNAHQNCPDGSDEDRLLCENHH------ | T | H | W | F | SEQ ID NO: 81 |
| LRP2CR28 | ---CD-SNEWQCANK--RCIPESW--QCDTFNDCOEDNSDEDSSHCAS------- | | | | | SEQ ID NO: 82 |
| LRP2CR30 | ---LCDNFTEFSCKTNY--RCIPKWA--VCNGVDDCRDNSDEQGCEERT------- | A | V | W | Q | SEQ ID NO: 83 |
| LRP2CR31 | ---CHPVGDFRCKNH--RCIPLRW--QCDGQNDCGDNSDEENCAPRE-------- | | | | | SEQ ID NO: 84 |
| LRP2CR34 | DGAYCQATMFECKNH--VCIPPYW--KCDGDDDCGDDSDEELHLCLDVP------ | W | D | E | V | SEQ ID NO: 85 |
| LRP2CR35 | ---CNSPNRFRCDNN--RCIYSHE--VCNGVDDCGBGTDTTEEHCRKPTPKP--- | E | V | N | A | SEQ ID NO: 86 |
| LRP2CR36 | ---CT-EYEYKCGNG--HCIPHDN--VCDDADDCGDWSDELGCNKGKERTCAENI | | | | | SEQ ID NO: 87 |
| LRP6CR1 | --PTCS-PQQFTCFTGEIDCIPVAW--RCDGFTECEDHSDELNCPV--------- | W | F | L | D | SEQ ID NO: 88 |
| LRP6CR2 | ---CS-ESQFQCASG--QCIDGAL--RCNGDANCQDKSDEKNCEVL-------- | L | D | K | N | SEQ ID NO: 89 |
| LRP6CR3 | ---CL-IDQFRCANG--QCIGKHK--KCDHNVDCSDKSDFLDCYPT-------- | | | | | SEQ ID NO: 90 |

Figure 3.
Native CR proteins
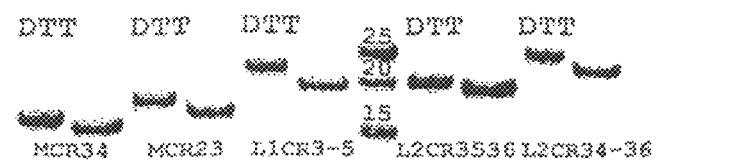
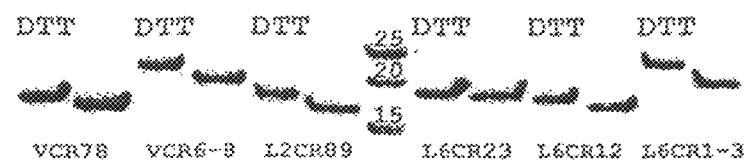
LRP2 CR89 variants

Figure 5a.
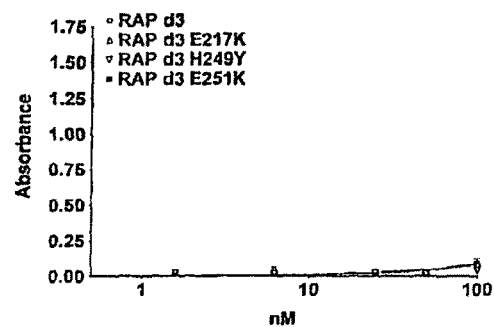
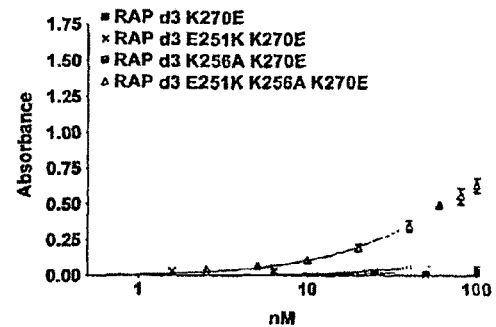
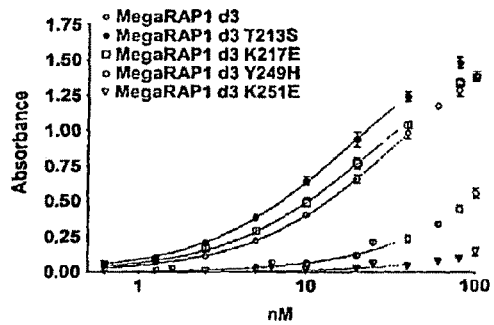
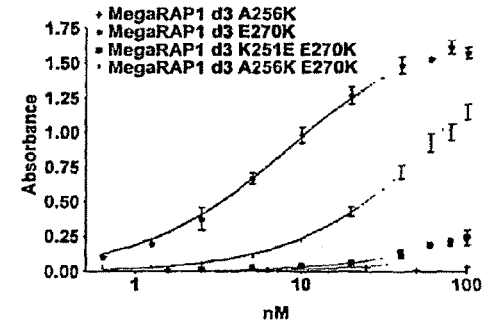

Figure 5b.
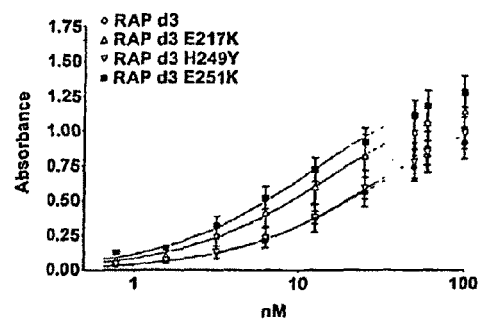
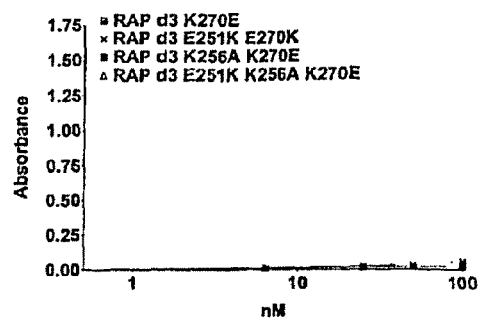
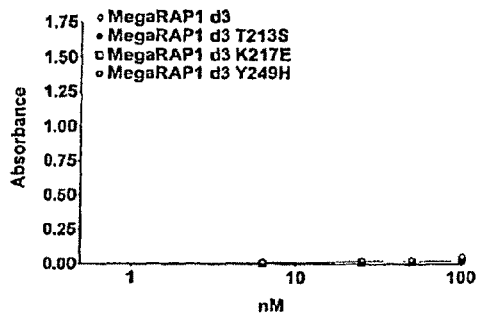
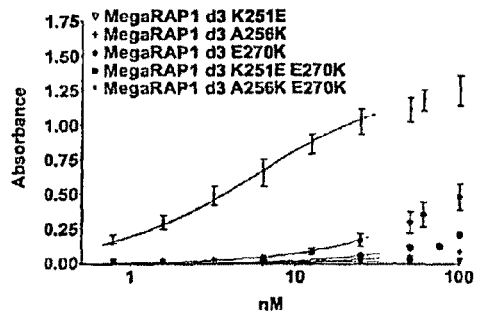

Figure 8. Amino acid sequences of RAP d3 variants selected on CR pairs d3
LDRLRRVSHQGYSTEAEFEEPRVIDLWDLEQSANLTDKELEAFREELKHFEAKIEKHNHYQKQ
LEIAHEKLRHAESVGDGERVSRSREKHALLEGRTKELGYTVKKHLQDLSGRISRAR
(SEQ ID NO: 92)

MegaRAP1
LDRLRRVSHQGYSTEAEFEEPRVIDLWDLEQSANLTDKELEAFREELKHFKAKIEAHNHYQKQ
LEIAHEDLRHAESVGDGERVSRSREKHALLEGRTKELGYTVKKHLQDLSGRISRAR
(SEQ ID NO: 93)

VRAP2
LDRLRRVSHQGYSTEAEFEEPRVIDLWDLEQSANLTDKELEAFREELKHFTAKIEIHNHYQKQL
EIAHEELRHAESVGDGERVSRSREKHALLEGLTKELGYTVKKHLQDLSGRISRAR
(SEQ ID NO: 95)

MatRAP1
LDRLRRVSHQGYSTEAEFEEPRVIDLWDLEQSANLTDKELEAFREELKHFAAKIEVYNHYQKQ
LEFAHEWLRHAESVGDGERVSRSREKHALLEGRTKELGYTVKKHLQDLSGRISRAR
(SEQ ID NO: 96)

MatRAP2
LDRLRRVSHQGYSTEAEFEEPRVIDLWDLEQSANLTDKELEAFREELKHFGAKIERHNHYQKQ
LEFAHEWLRHAESVGDSERVSRSREKHALLEGRTKELGYTVKKHLQDLSGRISRAR
(SEQ ID NO: 97)

320RAP1
LDRLRRVSHQGYSTEAEFEEPRVIDLWDLEQSANLTDKELEAFREELKHFAAKIESHNHYQKQL
EIAHESMRHAESVGYGERMSRSREKHALLEGRTKELGYTVTMHLQDLSG RISRAR
(SEQ ID NO: 98)

Figure 9. Relative affinity of sequentially-truncated forms of MatRAP1 to MAT CR12.
(fnctn is the relative binding signal under isomolar conditions)

| fnctn | ID  | Sequence | aa | SEQ |
|-------|-----|----------|-----|-----|
| 0.22  | MR1 | ALDRLRRVSHQGYSTEAEFEEPRVIDLWDLEQSANLTDKELEAFREELKGHFAAKIEVYNHYQKQLEFAHEWLRHAESVGDGERVSRSREKHALLEGRTKELGYTVKKHLQDLSGRISRARAFAE | 119 | 102 |
| 0.10  | 1   | ------------AGYSTEAEFEEPRVIDLWDLEQSANLTDKELEAFREELKHFAAKIEVYNHYQKQLEFAHEWLRHAESVGDGERVSRSREKHALLEGRTKELGYTVKKHLQDLSGRISRARAFAE | 109 | 103 |
| 0.35  | 2   | ------------------------------ASANLTDKELEAFREELKHFAAKIEVYNHYQKQLEFAHEWLRHAESVGDGERVSRSREKHALLEGRTKELGYTVKKHLQDLSGRISRARAFAE | 88 | 104 |
| 0.65  | 3   | ---------------------------------------------AFREELKHFAAKIEVYNHYQKQLEFAHEWLRHAESVGDGERVSRSREKHALLEGRTKELGYTVKKHLQDLSGRISRARAFAE | 77 | 105 |
| 0     | 4   | -----------------------------------------------------------AKIEVYNHYQKQLEFAHEWLRHAESVGDGERVSRSREKHALLEGRTKELGYTVKKHLQDLSGRISRARAFAE | 67 | 106 |
| 0     | 6   | -----------------------------------------------------------------AHNHYQKQLEFAHEWLRHAESVGDGERVSRSREKHALLEGRTKELGYTVKKHLQDLSGRISRARAFAE | 63 | 107 |
| 0     | 8   | -----------------------------------------------------------------------AEFAHEWLRHAESVGDGERVSRSREKHALLEGRTKELGYTVKKHLQDLSGRISRARAFAE | 55 | 108 |
| 0     | 7   | ---------------------------------------------------------------------------AHEWLRHAESVGDGERVSRSREKHALLEGRTKELGYTVKKHLQDLSGRISRARAFAE | 52 | 109 |
| 1.3   | 3R1 | ---------------------------------------------AFREELKHFAAKIEVYNHYQKQLEFAHEWLRHAESVGDGERVSRSREKHALLEGRTKELGYTVKKHLQDLSGRISRARB | 77 | 110 |
| 2.7   | 3R2 | ---------------------------------------------AFREELKHFAAKIEVYNHYQKQLEFAHEWLRHAESVGDGERVSRSREKHALLEGRTKELGYTVKKHLQDLSGB | 71 | 111 |
| 0     | 3R4 | ---------------------------------------------AFREELKHFAAKIEVYNHYQKQLEFAHEWLRHAESVGDGERVSRSREKHALLEB | 52 | 112 |
| 0     | 3R5 | ---------------------------------------------AFREELKHFAAKIEVYNHYQKQLEFAHEWLRHAESVGDGERVSRSB | 44 | 113 |
| 0     | 3R6 | ---------------------------------------------AFREELKHFAAKIEVYNHYQKQLEFAHEWLRHAESB | 34 | 114 |

A – MHHHHHHSSGLVPRGSGMKETAAAKFERQHMDSPDLGTDDDKAMADIGS (SEQ ID NO: 99)

B – KLAAALEHHHHHH (SEQ ID NO: 100)

C – GPLGS (SEQ ID NO: 101)

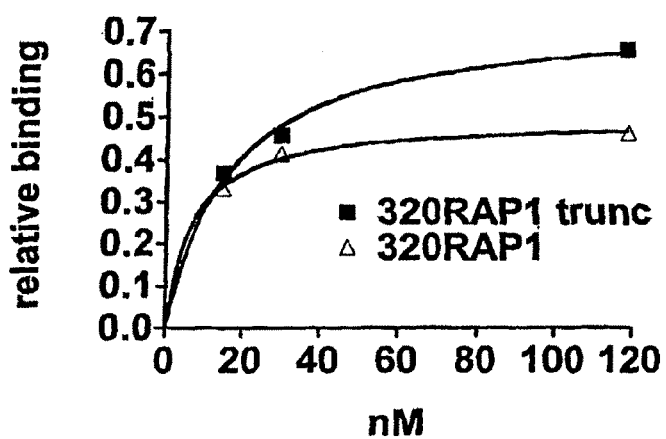
Figure 10. Binding of a RAP variant (320RAP) and its 71 amino acid truncated form (see Figure 14 for identical truncation of MATRAP1) selected on the FDC-8D6 antigen CR pair.

Figure 11. Reducing (left) and non-reducing (right) Western blots of RAP-GDNF (higher band) and GDNF (lower band).
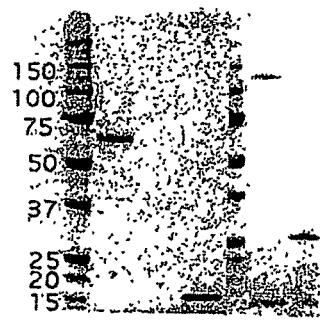

Figure 12. Binding of RAP-GDNF to GFRα by solid phase assay.
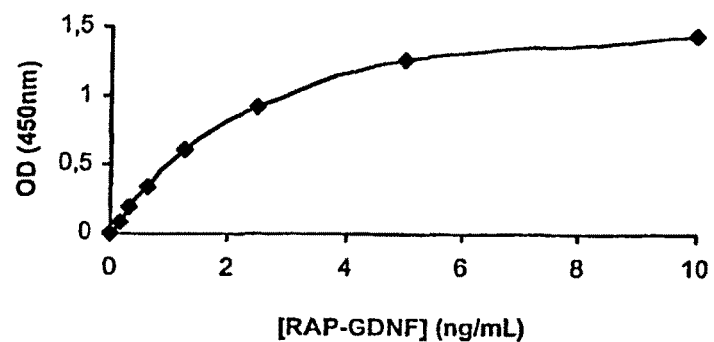

Figure 13. Immunoprecipitation of Ret in SK-N-SH cells after treatment with RAP-GDNF and GFRα and anti-phosphotyrosine antibodies.
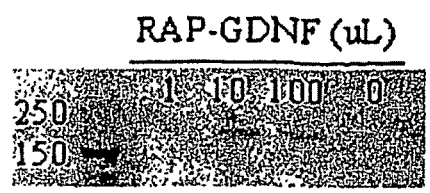

Figure 14. Immunoprecipitation of a RAP-GDNF/GFRα/phospho-Ret complex using anti-RAP-agarose beads.
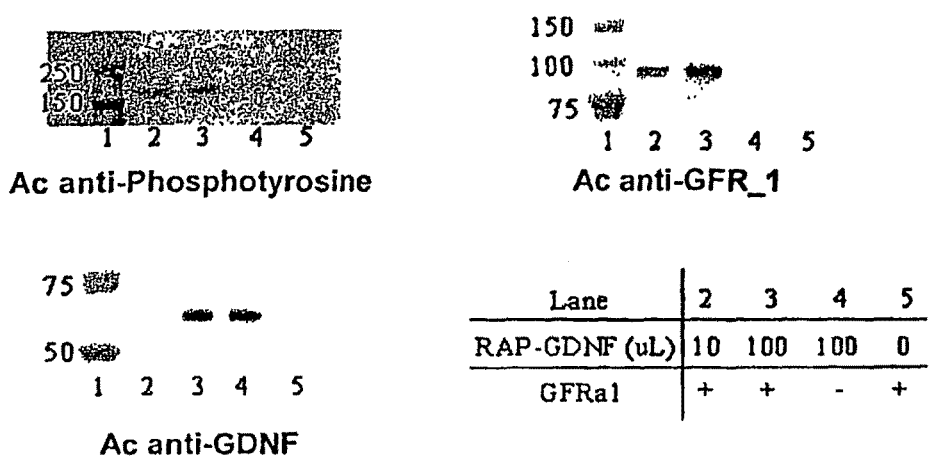

Figure 15a. Induction of neurite outgrowth by GDNF and RAP-GDNF in PC12 cells.
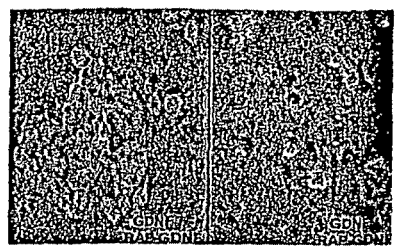

Figure 15b. Dose-response of PC12 neurite outgrowth with GDNF and RAP-GDNF concentration.
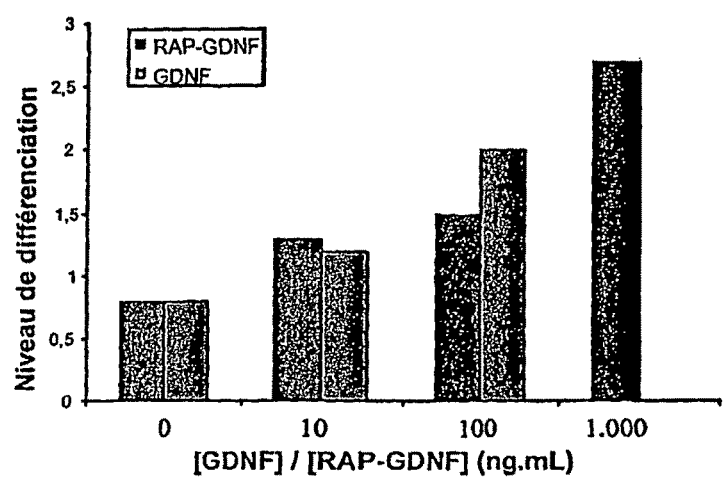

Figure 16

| d3 sequence | variable positions | | | | | | LRP2 CR89 | | LRP1 CR3-5 | |
|---|---|---|---|---|---|---|---|---|---|---|
| | 213 | 217 | 249 | 251 | 256 | 270 | $K_d$ (nM) | % max | $K_d$ (nM) | % max |
| RAP | S | E | H | E | K | K | NF | 5% | 16 ± 4 | 76% |
| RAP E217K | S | K | H | E | K | K | NF | 5% | 9 ± 1 | 91% |
| RAP H249Y | S | E | Y | E | K | K | NF | 2% | 28 ± 8 | 90% |
| RAP E251K | S | E | H | K | K | K | NF | 5% | 7 ± 1 | 100% |
| RAP K270E | S | E | H | E | K | E | NF | 2% | NF | 4% |
| RAP K256A, K270E | S | E | H | E | A | E | NF | 3% | NF | 2% |
| RAP E251K, K270E | S | E | H | K | K | E | NF | 2% | NF | 4% |
| RAP E251K, K256A, K270E | S | E | H | K | A | E | 114 ± 32 | 40% | NF | 2% |
| MegaRAP1 | T | K | Y | K | A | E | 38 ± 3 | 88% | NF | 4% |
| MegaRAP1 T213S | S | K | Y | K | A | E | 19 ± 1 | 94% | NF | 2% |
| MegaRAP1 K217E | T | E | Y | K | A | E | 25 ± 1 | 88% | NF | 2% |
| MegaRAP1 Y249H | T | K | H | K | A | E | NF | 35% | NF | 2% |
| MegaRAP1 K251E | T | K | Y | E | A | E | NF | 11% | NF | 2% |
| MegaRAP1 A256K | T | K | Y | K | K | E | NF | 2% | NF | 6% |
| MegaRAP1 E270K | T | K | Y | K | A | K | 8 ± 1 | 100% | 114 ± 31 | 85% |
| MegaRAP1 A256K, E270K | T | K | Y | K | K | K | 72 ± 11 | 73% | 4 ± 0.3 | 93% |
| MegaRAP1 K251E, E270K | T | K | Y | E | A | K | 153 ± 104 | 16% | NF | 16% |

Figure 17

| LRP2 CR89 variants | | | | RAP d3 | | MegaRAP1 d3 | |
|---|---|---|---|---|---|---|---|
| 1040 | 1047 | 1081 | 1088 | $K_d$ (nM) | % max bind | $K_d$ (nM) | % max bind |
| A | C | AÖ | CÖ | | | | |
| Y | V | W | R | NF | 7% | 33 ± 2 | 100% |
| Y | V | W | D | NF | 7% | 78 ± 25 | 55% |
| Y | D | W | D | NF | 6% | NF | 3% |
| Y | D | W | R | NF | 6% | NF | 11% |
| W | V | W | R | NF | 9% | NF | 5% |
| W | D | W | R | NF | 11% | NF | 3% |
| W | V | W | D | NF | 16% | NF | 4% |
| W | D | W | D | NF | 15% | NF | 1% |

Figure 18

| d3 | CR | K$_d$ | 249 | 251 | 256 | 257 | 266 | 270 | 279 | 280 | 296 | 305 |
|---|---|---|---|---|---|---|---|---|---|---|---|---|
| RAP | LRP1 CR3-5 | 16 ± 4 | H | E | K | H | I | K | D | G | R | K |
| MegaRAP1 | LRP2 CR89 | 38 ± 3 | Y | K | A | | | E | | | | |
| VRAP2 | VLDLR CR78 | 44 ± 9 | | T | L | | | Y | | | L | |
| MatRAP1 | MAT CR12 | ND | | A | V | Y | F | W | | I | | |
| MatRAP2 | MAT CR23 | ND | | G | R | | F | W | | S | | |
| 320RAP1 | 8D6 CR12 | ND | | A | S | | | S | Y | | | M |

SEQUENCE LISTING

```
<160> NUMBER OF SEQ ID NOS: 121

<210> SEQ ID NO 1
<211> LENGTH: 1493
<212> TYPE: DNA
<213> ORGANISM: Homo sapiens

<400> SEQUENCE: 1
tgagcggggg atgatggcgc cgcggagggt caggtcgttt ctgcgcgggc tcccggcgct      60
gctactgctg ctgctcttcc tcgggccctg gcccgctgcg agccacggcg gcaagtactc     120
gcgggagaag aaccagccca gccgtcccc gaaacgcgag tccggagagg agttccgcat     180
ggagaagttg aaccagctgt gggagaaggc ccagcgactg catcttcctc ccgtgaggct     240
ggccgagctc cacgctgatc tgaagataca ggagagggac gaactcgcct ggaagaaact     300
aaagcttgac ggcttggacg aagatgggga gaaggaagcg agactcatac gcaacctcaa     360
tgtcatcttg gccaagtatg gtctggacgg aaagaaggac gctcggcagg tgaccagcaa     420
ctccctcagt ggcacccagg aagacgggct ggatgacccc aggctggaaa agctgtggca     480
caaggcgaag acctctggga aattctccgg cgaagaactg acaagctct ggcgggagtt     540 cctgcatcac aaagagaaag ttcacgagta caacgtcctg ctggagaccc tgagcaggac     600
cgaagaaatc cacgagaacg tcattagccc ctcggacctg agcgacatca agggcagcgt     660
cctgcacagc aggcacacgg agctgaagga gaagctgcgc agcatcaacc agggcctgga     720
ccgcctgcgc agggtcagcc accagggcta cagcactgag gctgagttcg aggagcccag     780
ggtgattgac ctgtgggacc tggcgcagtc cgccaacctc acggacaagg agctggaggc     840 gttccggag gagctcaagc acttcgaagc caaaatcgag aagcacaacc actaccagaa     900
gcagctggag attgcgcacg agaagctgag gcacgcagag agcgtgggcg acggcgagcg     960
tgtgagccgc agccgcgaga gcacgccct gctggagggg cggaccaagg agctgggcta    1020
cacggtgaag aagcatctgc aggacctgtc cggcaggatc ccagagctc ggcacaacga    1080
```

```
actctgaagg cactggggag cccagcccgg cagggaagag gccagcgtga aggacctggg   1140
ctcttggccg tggcatttcc gtggacagcc cgccgtcagg gtggctgggg ctggcacggg   1200
tgtcgaggca ggaaggattg tttctggtga ctgcagccgc tgccgtcgcg acacagggct   1260
tggtggtggt agcatttggg tctgagatcg gcccagctct gactgaaggg gcttggcttc   1320
cactcagcat cagcgtggca gtcaccaccc cagtgaggac ctcgatgtcc agctgctgtc   1380
aggtctgata gtcctctgct aaacaacac gatttacata aaaaatctta cacatctgcc   1440
accggaaata ccatgcacag agtccttaaa aaatagagtg cagtatttaa acc           1493
```

<210> SEQ ID NO 2
<211> LENGTH: 357
<212> TYPE: PRT
<213> ORGANISM: Homo sapiens

<400> SEQUENCE: 2

```
Met Ala Pro Arg Arg Val Arg Ser Phe Leu Arg Gly Leu Pro Ala Leu
  1               5                  10                  15

Leu Leu Leu Leu Leu Phe Leu Gly Pro Trp Pro Ala Ala Ser His Gly
             20                  25                  30

Gly Lys Tyr Ser Arg Glu Lys Asn Gln Pro Lys Pro Ser Pro Lys Arg
         35                  40                  45

Glu Ser Gly Glu Glu Phe Arg Met Glu Lys Leu Asn Gln Leu Trp Glu
     50                  55                  60

Lys Ala Gln Arg Leu His Leu Pro Pro Val Arg Leu Ala Glu Leu His
 65                  70                  75                  80

Ala Asp Leu Lys Ile Gln Glu Arg Asp Glu Leu Ala Trp Lys Lys Leu
                 85                  90                  95

Lys Leu Asp Gly Leu Asp Glu Asp Gly Glu Lys Glu Ala Arg Leu Ile
            100                 105                 110

Arg Asn Leu Asn Val Ile Leu Ala Lys Tyr Gly Leu Asp Gly Lys Lys
        115                 120                 125

Asp Ala Arg Gln Val Thr Ser Asn Ser Leu Ser Gly Thr Gln Glu Asp
    130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
            180                 185                 190

Leu Ser Arg Thr Glu Glu Ile His Glu Asn Val Ile Ser Pro Ser Asp
        195                 200                 205

Leu Ser Asp Ile Lys Gly Ser Val Leu His Ser Arg His Thr Glu Leu
    210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Phe Glu Glu Pro Arg
                245                 250                 255

Val Ile Asp Leu Trp Asp Leu Ala Gln Ser Ala Asn Leu Thr Asp Lys
            260                 265                 270

Glu Leu Glu Ala Phe Arg Glu Glu Leu Lys His Phe Glu Ala Lys Ile
        275                 280                 285

Glu Lys His Asn His Tyr Gln Lys Gln Leu Glu Ile Ala His Glu Lys
    290                 295                 300
```

```
Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
                325                 330                 335

Thr Val Lys Lys His Leu Gln Asp Leu Ser Gly Arg Ile Ser Arg Ala
            340                 345                 350

Arg His Asn Glu Leu
            355

<210> SEQ ID NO 3
<211> LENGTH: 66
<212> TYPE: DNA
<213> ORGANISM: Artificial sequence
<220> FEATURE:
<223> OTHER INFORMATION: Synthetic primer - LRP6CR1F

<400> SEQUENCE: 3
gcgataggat ccccaacatg ttctcctcag cagtttactt gtttcacggg ggaaattgac      60
tgtatc                                                                66

<210> SEQ ID NO 4
<211> LENGTH: 70
<212> TYPE: DNA
<213> ORGANISM: Artificial sequence
<220> FEATURE:
<223> OTHER INFORMATION: Synthetic primer - LRP6CR2R

<400> SEQUENCE: 4
gcgataaagc ttttatcaaa gcacttcaca gttcttctca tctgatttgt cctggcagtt      60
tgcatctcca                                                            70

<210> SEQ ID NO 5
<211> LENGTH: 65
<212> TYPE: DNA
<213> ORGANISM: Artificial sequence
<220> FEATURE:
<223> OTHER INFORMATION: Synthetic primer - LRP6CR2F

<400> SEQUENCE: 5
gcgataggat cccctgtatg ctcagagtcc cagttccagt gtgccagtgg gcagtgtatt      60
gatgg                                                                 65

<210> SEQ ID NO 6
<211> LENGTH: 63
<212> TYPE: DNA
<213> ORGANISM: Artificial sequence
<220> FEATURE:
<223> OTHER INFORMATION: Synthetic primer - LPR6CR3R

<400> SEQUENCE: 6
gcgataaagc tttcactaag tcggataaca atccagttca tctgacttgt cactgcaatc      60
cac                                                                   63

<210> SEQ ID NO 7
<211> LENGTH: 60
<212> TYPE: DNA
<213> ORGANISM: Artificial sequence
<220> FEATURE:
<223> OTHER INFORMATION: Synethic primer - VLDLRCR6F

<400> SEQUENCE: 7
gcgataggat cccacaccaa gtgtccagcc agcgaaatcc agtgcggctc tggcgagtgc      60
```

<210> SEQ ID NO 8
<211> LENGTH: 51
<212> TYPE: DNA
<213> ORGANISM: Artificial sequence
<220> FEATURE:
<223> OTHER INFORMATION: Synthetic primer - VLDLRCR7F

<400> SEQUENCE: 8
gcgataggat ccacttgccg acctgaccaa tttgaatgtg aggatggcag c        51

<210> SEQ ID NO 9
<211> LENGTH: 64
<212> TYPE: DNA
<213> ORGANISM: Artificial sequence
<220> FEATURE:
<223> OTHER INFORMATION: Synthetic primer - VLDLRCR8R

<400> SEQUENCE: 9
gcgataaagc ttttatcatt cgtttatatg acactctttc aggggctcat cactccagtc    60
cctg                                                                 64

<210> SEQ ID NO 10
<211> LENGTH: 57
<212> TYPE: DNA
<213> ORGANISM: Artificial sequence
<220> FEATURE:
<223> OTHER INFORMATION: Synthetic primer - LRP2CR8F

<400> SEQUENCE: 10
gcgataggat cccccacgga gcagtgtggc ttattttcct tcccctgtaa aaatggc       57

<210> SEQ ID NO 11
<211> LENGTH: 73
<212> TYPE: DNA
<213> ORGANISM: Artificial sequence
<220> FEATURE:
<223> OTHER INFORMATION: Synthetic primer - LRP2CR9R

<400> SEQUENCE: 11
gcgataaagc ttttatcatg cgtgggtggg gcagttgtgc tcatcactgc catccacaca    60
gtcgttgcgt ttg                                                       73

<210> SEQ ID NO 12
<211> LENGTH: 70
<212> TYPE: DNA
<213> ORGANISM: Artificial sequence
<220> FEATURE:
<223> OTHER INFORMATION: Synthetic primer - LRP2CR34F

<400> SEQUENCE: 12
gcgataggat ccgatggtgc atactgccag gctactatgt tcgaatgcaa aaaccatgtt    60
tgtatcccgc                                                           70

<210> SEQ ID NO 13
<211> LENGTH: 63
<212> TYPE: DNA
<213> ORGANISM: Artificial sequence
<220> FEATURE:
<223> OTHER INFORMATION: Synthetic primer - LRP2CR35F

<400> SEQUENCE: 13
gcgataggat ccgatgttcc ctgtaattca ccaaaccgtt tccggtgtga caacaatcgc    60

```
tgc                                                                63
```

<210> SEQ ID NO 14
<211> LENGTH: 70
<212> TYPE: DNA
<213> ORGANISM: Artificial sequence
<220> FEATURE:
<223> OTHER INFORMATION: Synthetic primer - LRP2CR36R

<400> SEQUENCE: 14

```
gcgataaagc ttttatcata tattttcagc acatgttctt tcttttcctt tattgcaacc   60
cagttcatcg                                                         70
```

<210> SEQ ID NO 15
<211> LENGTH: 54
<212> TYPE: DNA
<213> ORGANISM: Artificial sequence
<220> FEATURE:
<223> OTHER INFORMATION: Synthetic primer - ST14F1

<400> SEQUENCE: 15

```
gcgataggat ccccatgccc ggggcagttc acgtgccgca cggggcggtg tatc         54
```

<210> SEQ ID NO 16
<211> LENGTH: 54
<212> TYPE: DNA
<213> ORGANISM: Artificial sequence
<220> FEATURE:
<223> OTHER INFORMATION: Synthetic primer - ST14F2

<400> SEQUENCE: 16

```
gcgataggat cctgcgacgc cggccaccag ttcacgtgca agaacaagtt ctgc         54
```

<210> SEQ ID NO 17
<211> LENGTH: 53
<212> TYPE: DNA
<213> ORGANISM: Artificial sequence
<220> FEATURE:
<223> OTHER INFORMATION: Synthetic primer - ST14F3

<400> SEQUENCE: 17

```
gcgataggat ccagttgtcc ggcccagacc ttcaggtgtt ccaatgggaa gtg          53
```

<210> SEQ ID NO 18
<211> LENGTH: 59
<212> TYPE: DNA
<213> ORGANISM: Artificial sequence
<220> FEATURE:
<223> OTHER INFORMATION: Synthetic primer - ST14R1

<400> SEQUENCE: 18

```
gcgataaagc ttttatcaac ccctgctcgt cgctgttgtc tccgcagtcg ttcacactg    59
```

<210> SEQ ID NO 19
<211> LENGTH: 43
<212> TYPE: DNA
<213> ORGANISM: Artificial sequence
<220> FEATURE:
<223> OTHER INFORMATION: Synthetic primer - ST14R2

<400> SEQUENCE: 19

```
gcgataaagc ttttatcaac tgcacccctg ctcgtcgctg ttg                     43
```

<210> SEQ ID NO 20
<211> LENGTH: 64

```
<212> TYPE: DNA
<213> ORGANISM: Artificial sequence
<220> FEATURE:
<223> OTHER INFORMATION: Synthetic primer - ST14R3

<400> SEQUENCE: 20
gcgataaagc ttttatcagt cgcagtcctt ctcatctgag ccgtcgctac agtcctcctt    60
cccg                                                                 64

<210> SEQ ID NO 21
<211> LENGTH: 39
<212> TYPE: DNA
<213> ORGANISM: Artificial sequence
<220> FEATURE:
<223> OTHER INFORMATION: Synthetic primer - LRP1CR3F

<400> SEQUENCE: 21
gcgataggat cccccagtg ccagccaggc gagtttgcc                            39

<210> SEQ ID NO 22
<211> LENGTH: 45
<212> TYPE: DNA
<213> ORGANISM: Artificial sequence
<220> FEATURE:
<223> OTHER INFORMATION: Synthetic primer - LRP1CR5R

<400> SEQUENCE: 22
gcgataagct ttcaataggc acacgaagca gactcatcag agcgg                    45

<210> SEQ ID NO 23
<211> LENGTH: 56
<212> TYPE: DNA
<213> ORGANISM: Artificial sequence
<220> FEATURE:
<223> OTHER INFORMATION: Synthetic primer - 8D6AF

<400> SEQUENCE: 23
gcgataggat cctcgtgccc acccaccaag ttccagtgcc gcaccagtgg cttatg        56

<210> SEQ ID NO 24
<211> LENGTH: 50
<212> TYPE: DNA
<213> ORGANISM: Artificial sequence
<220> FEATURE:
<223> OTHER INFORMATION: Synthetic primer - 8D65AR

<400> SEQUENCE: 24
gcgataaagc ttttatcatc cacagccgag ctcgtcgctg gagtcgggac               50

<210> SEQ ID NO 25
<211> LENGTH: 28
<212> TYPE: DNA
<213> ORGANISM: Artificial sequence
<220> FEATURE:
<223> OTHER INFORMATION: Synthetic primer - CR89YWF

<400> SEQUENCE: 25
gtgcccaatt actggctctg tgatggag                                       28

<210> SEQ ID NO 26
<211> LENGTH: 28
<212> TYPE: DNA
<213> ORGANISM: Artificial sequence
<220> FEATURE:
<223> OTHER INFORMATION: Synthetic primer - CR89YWR
```

<400> SEQUENCE: 26
ctccatcaca gagccagtaa ttgggcac                                28

<210> SEQ ID NO 27
<211> LENGTH: 31
<212> TYPE: DNA
<213> ORGANISM: Artificial sequence
<220> FEATURE:
<223> OTHER INFORMATION: Synthetic primer - CR89V1047DF

<400> SEQUENCE: 27
ctctgtgatg gagacgatga ttgtcatgat a                            31

<210> SEQ ID NO 28
<211> LENGTH: 31
<212> TYPE: DNA
<213> ORGANISM: Artificial sequence
<220> FEATURE:
<223> OTHER INFORMATION: Synthetic primer - CR89V1047DR

<400> SEQUENCE: 28
tatcatgaca atcatcgtct ccatcacaga g                            31

<210> SEQ ID NO 29
<211> LENGTH: 41
<212> TYPE: DNA
<213> ORGANISM: Artificial sequence
<220> FEATURE:
<223> OTHER INFORMATION: Synthetic primer - CR89R1088DF

<400> SEQUENCE: 29
cacactggcg ctgtgacaaa gacaacgact gtgtggatgg c                 41

<210> SEQ ID NO 30
<211> LENGTH: 41
<212> TYPE: DNA
<213> ORGANISM: Artificial sequence
<220> FEATURE:
<223> OTHER INFORMATION: Synthetic primer - CR89R1088DR

<400> SEQUENCE: 30
gccatccaca cagtcgttgt ctttgtcaca gcgccagtgt g                 41

<210> SEQ ID NO 31
<211> LENGTH: 36
<212> TYPE: DNA
<213> ORGANISM: Artificial sequence
<220> FEATURE:
<223> OTHER INFORMATION: Synthetic primer - RAP2KXF

<400> SEQUENCE: 31
ccctcggacg tcagcgacat caagggcagc gtcctg                       36

<210> SEQ ID NO 32
<211> LENGTH: 65
<212> TYPE: DNA
<213> ORGANISM: Artificial sequence
<220> FEATURE:
<223> OTHER INFORMATION: Synthetic primer - RAP2KX2
<220> FEATURE:
<221> NAME/KEY: misc_feature
<222> LOCATION: (29)..(30)
<223> OTHER INFORMATION: n is a, c, g, or t

<400> SEQUENCE: 32
ctccagctgc ttctggtagt ggttgtgvnn ctcctcgatt ttggcttcga agtgcttgag    60
ctcct 65

<210> SEQ ID NO 33
<211> LENGTH: 58
<212> TYPE: DNA
<213> ORGANISM: Artificial sequence
<220> FEATURE:
<223> OTHER INFORMATION: Synthetic primer - RAP2KX1
<220> FEATURE:
<221> NAME/KEY: misc_feature
<222> LOCATION: (25)..(26)
<223> OTHER INFORMATION: n is a, c, g, or t

<400> SEQUENCE: 33
aagcagctgg agattgcgca cgagnnbctg aggcacgcag agagcgtggg cgaacggc 58

<210> SEQ ID NO 34
<211> LENGTH: 19
<212> TYPE: DNA
<213> ORGANISM: Artificial sequence
<220> FEATURE:
<223> OTHER INFORMATION: Synthetic primer - RAPmut1R

<400> SEQUENCE: 34
ggtgcggggc ctcaccggt 19

<210> SEQ ID NO 35
<211> LENGTH: 29
<212> TYPE: DNA
<213> ORGANISM: Artificial sequence
<220> FEATURE:
<223> OTHER INFORMATION: Synthetic primer - MORPHF4

<400> SEQUENCE: 35
ggcccagatc taccggtttc tgcctcggc 29

<210> SEQ ID NO 36
<211> LENGTH: 76
<212> TYPE: DNA
<213> ORGANISM: Artificial sequence
<220> FEATURE:
<223> OTHER INFORMATION: Synthetic primer - D3HALFR2
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t

<400> SEQUENCE: 36
gtgcgcaatc tcgagctgct tctggtagtg gttgtgvnnc tcgattttgg cvnngaagtg 60
cttgagctcc tcccgg 76

<210> SEQ ID NO 37
<211> LENGTH: 67
<212> TYPE: DNA
<213> ORGANISM: Artificial sequence
<220> FEATURE:
<223> OTHER INFORMATION: Synthetic primer - D3HALFF2
<220> FEATURE:
<221> NAME/KEY: misc_feature
<222> LOCATION: (35)..(36)
<223> OTHER INFORMATION: n is a, c, g, or t

<400> SEQUENCE: 37

```
ccactaccag aagcagctcg agattgcgca cgagnnbctg aggcacgcag agagcgtggg    60
cgacggc                                                              67
```

<210> SEQ ID NO 38
<211> LENGTH: 33
<212> TYPE: DNA
<213> ORGANISM: Artificial sequence
<220> FEATURE:
<223> OTHER INFORMATION: Synthetic primer - MORPHR3

<400> SEQUENCE: 38

```
gagtgcggcc gcaagcttat cttctgcctc ggc                                 33
```

<210> SEQ ID NO 39
<211> LENGTH: 40
<212> TYPE: DNA
<213> ORGANISM: Artificial sequence
<220> FEATURE:
<223> OTHER INFORMATION: Synthetic primer - d3 Rescue F

<400> SEQUENCE: 39

```
gcgataggat ccctggaccg cctgcgcagg gtcagccacc                          40
```

<210> SEQ ID NO 40
<211> LENGTH: 42
<212> TYPE: DNA
<213> ORGANISM: Artificial sequence
<220> FEATURE:
<223> OTHER INFORMATION: Synthetic primer - d3 Rescue R

<400> SEQUENCE: 40

```
gcgataaagc ttttatcaag atctaccggt ttctgcctcg gc                       42
```

<210> SEQ ID NO 41
<211> LENGTH: 56
<212> TYPE: DNA
<213> ORGANISM: Artificial sequence
<220> FEATURE:
<223> OTHER INFORMATION: Synthetic primer - V2AR1

<400> SEQUENCE: 41

```
agggtcagcc accagggcta cagcactgag gctaagttcg aggagcccag ggtgat        56
```

<210> SEQ ID NO 42
<211> LENGTH: 56
<212> TYPE: DNA
<213> ORGANISM: Artificial sequence
<220> FEATURE:
<223> OTHER INFORMATION: Synthetic primer - V2AR2

<400> SEQUENCE: 42

```
cagccaccag ggctacacca ctgaggctga gttcgaggag cccagggtga ttgacc        56
```

<210> SEQ ID NO 43
<211> LENGTH: 56
<212> TYPE: DNA
<213> ORGANISM: Artificial sequence
<220> FEATURE:
<223> OTHER INFORMATION: Synthetic primer - V2AR3

<400> SEQUENCE: 43

```
ggaggcgttc cgggaggagc tcaagcactt caaagccaaa attgaggccc acaacc        56
```

<210> SEQ ID NO 44
<211> LENGTH: 56

```
<212> TYPE: DNA
<213> ORGANISM: Artificial sequence
<220> FEATURE:
<223> OTHER INFORMATION: Synthetic primer - V2AR4

<400> SEQUENCE: 44
cgttccggga ggagctcaag tacttcgaag ccaaaattga ggcccacaac cactac      56

<210> SEQ ID NO 45
<211> LENGTH: 58
<212> TYPE: DNA
<213> ORGANISM: Artificial sequence
<220> FEATURE:
<223> OTHER INFORMATION: Synthetic primer - V2AR5

<400> SEQUENCE: 45
gctcaagtac ttcaaagcca aaattgagaa gcacaaccac taccagaagc agctggag    58

<210> SEQ ID NO 46
<211> LENGTH: 58
<212> TYPE: DNA
<213> ORGANISM: Artificial sequence
<220> FEATURE:
<223> OTHER INFORMATION: Synthetic primer - V2AR6

<400> SEQUENCE: 46
agaagcagct ggagattgcg cacgagaagc tgaggcacgc agagagcgtg ggcgacgg    58

<210> SEQ ID NO 47
<211> LENGTH: 56
<212> TYPE: DNA
<213> ORGANISM: Artificial sequence
<220> FEATURE:
<223> OTHER INFORMATION: Synthetic primer - V2ARR1

<400> SEQUENCE: 47
atcaccctgg gctcctcgaa cttagcctca gtgctgtagc cctggtggct gaccct      56

<210> SEQ ID NO 48
<211> LENGTH: 56
<212> TYPE: DNA
<213> ORGANISM: Artificial sequence
<220> FEATURE:
<223> OTHER INFORMATION: Synthetic primer - V2ARR2

<400> SEQUENCE: 48
ggtcaatcac cctgggctcc tcgaactcag cctcagtggt gtagccctgg tggctg      56

<210> SEQ ID NO 49
<211> LENGTH: 56
<212> TYPE: DNA
<213> ORGANISM: Artificial sequence
<220> FEATURE:
<223> OTHER INFORMATION: Synthetic primer - V2ARR3

<400> SEQUENCE: 49
ggttgtgggc ctcaattttg gctttgaagt gcttgagctc ctcccggaac gcctcc      56

<210> SEQ ID NO 50
<211> LENGTH: 56
<212> TYPE: DNA
<213> ORGANISM: Artificial sequence
<220> FEATURE:
<223> OTHER INFORMATION: Synthetic primer - V2ARR4

<400> SEQUENCE: 50
```

```
gtagtggttg tgggcctcaa ttttggcttc gaagtacttg agctcctccc ggaacg      56

<210> SEQ ID NO 51
<211> LENGTH: 58
<212> TYPE: DNA
<213> ORGANISM: Artificial sequence
<220> FEATURE:
<223> OTHER INFORMATION: Synthetic primer - V2ARR5

<400> SEQUENCE: 51
ctccagctgc ttctggtagt ggttgtgctt ctcaattttg gctttgaagt acttgagc    58

<210> SEQ ID NO 52
<211> LENGTH: 58
<212> TYPE: DNA
<213> ORGANISM: Artificial sequence
<220> FEATURE:
<223> OTHER INFORMATION: Synthetic primer - V2ARR6

<400> SEQUENCE: 52
ccgtcgccca cgctctctgc gtgcctcagc ttctcgtgcg caatctccag ctgcttct    58

<210> SEQ ID NO 53
<211> LENGTH: 41
<212> TYPE: DNA
<213> ORGANISM: Artificial sequence
<220> FEATURE:
<223> OTHER INFORMATION: Synthetic primer - K256AF

<400> SEQUENCE: 53
cttcgaagcc aaaatcgagg cgcacaacca ctaccagaag c                     41

<210> SEQ ID NO 54
<211> LENGTH: 41
<212> TYPE: DNA
<213> ORGANISM: Artificial sequence
<220> FEATURE:
<223> OTHER INFORMATION: Synthetic primer - K256AR

<400> SEQUENCE: 54
gcttctggta gtggttgtgc gcctcgattt tggcttcgaa g                     41

<210> SEQ ID NO 55
<211> LENGTH: 39
<212> TYPE: DNA
<213> ORGANISM: Artificial sequence
<220> FEATURE:
<223> OTHER INFORMATION: Synthetic primer - K270EF

<400> SEQUENCE: 55
gctggagatt gcgcacgagg agctgaggca cgcagagag                        39

<210> SEQ ID NO 56
<211> LENGTH: 39
<212> TYPE: DNA
<213> ORGANISM: Artificial sequence
<220> FEATURE:
<223> OTHER INFORMATION: Synthetic primer - K270ER

<400> SEQUENCE: 56
ctctctgcgt gcctcagctc ctcgtgcgca atctccagc                        39

<210> SEQ ID NO 57
<211> LENGTH: 42
<212> TYPE: DNA
<213> ORGANISM: Artificial sequence
```

```
<220> FEATURE:
<223> OTHER INFORMATION: Synthetic primer - d3E251KF

<400> SEQUENCE: 57
gaggagctca agcacttcaa agccaaaatc gagaagcaca ac                    42

<210> SEQ ID NO 58
<211> LENGTH: 42
<212> TYPE: DNA
<213> ORGANISM: Artificial sequence
<220> FEATURE:
<223> OTHER INFORMATION: Synthetic primer - d3E251KF

<400> SEQUENCE: 58
gttgtgcttc tcgattttgg ctttgaagtg cttgagctcc tc                    42

<210> SEQ ID NO 59
<211> LENGTH: 42
<212> TYPE: DNA
<213> ORGANISM: Artificial sequence
<220> FEATURE:
<223> OTHER INFORMATION: Synthetic primer - d3E217KF

<400> SEQUENCE: 59
cagggctaca gcactgaggc taagttcgag gagcccaggg tg                    42

<210> SEQ ID NO 60
<211> LENGTH: 42
<212> TYPE: DNA
<213> ORGANISM: Artificial sequence
<220> FEATURE:
<223> OTHER INFORMATION: Synthetic primer - d3E217KR

<400> SEQUENCE: 60
caccctgggc tcctcgaact tagcctcagt gctgtagccc tg                    42

<210> SEQ ID NO 61
<211> LENGTH: 40
<212> TYPE: DNA
<213> ORGANISM: Artificial sequence
<220> FEATURE:
<223> OTHER INFORMATION: Synthetic primer - d3H249YF

<400> SEQUENCE: 61
gttccgggag gagctcaagt acttcgaagc caaaatcgag                       40

<210> SEQ ID NO 62
<211> LENGTH: 40
<212> TYPE: DNA
<213> ORGANISM: Artificial sequence
<220> FEATURE:
<223> OTHER INFORMATION: Synthetic primer - d3H249YR

<400> SEQUENCE: 62
ctcgattttg gcttcgaagt acttgagctc ctcccggaac                       40

<210> SEQ ID NO 63
<211> LENGTH: 8
<212> TYPE: PRT
<213> ORGANISM: Artificial sequence
<220> FEATURE:
<223> OTHER INFORMATION: LDLR CR1

<400> SEQUENCE: 63

Trp Val Cys Asp Gly Ser Ala Glu
1               5
```

<210> SEQ ID NO 64
<211> LENGTH: 8
<212> TYPE: PRT
<213> ORGANISM: Artificial sequence
<220> FEATURE:
<223> OTHER INFORMATION: LDLR CR3

<400> SEQUENCE: 64

Phe Val Cys Asp Ser Asp Arg Asp
1               5

<210> SEQ ID NO 65
<211> LENGTH: 8
<212> TYPE: PRT
<213> ORGANISM: Artificial sequence
<220> FEATURE:
<223> OTHER INFORMATION: LDLR CR5

<400> SEQUENCE: 65

Trp Arg Cys Asp Gly Gly Pro Asp
1               5

<210> SEQ ID NO 66
<211> LENGTH: 8
<212> TYPE: PRT
<213> ORGANISM: Artificial sequence
<220> FEATURE:
<223> OTHER INFORMATION: LDLR CR6

<400> SEQUENCE: 66

Arg Gln Cys Asp Arg Glu Tyr Asp
1               5

<210> SEQ ID NO 67
<211> LENGTH: 8
<212> TYPE: PRT
<213> ORGANISM: Artificial sequence
<220> FEATURE:
<223> OTHER INFORMATION: LDLR CR7

<400> SEQUENCE: 67

Lys Val Cys Asn Met Ala Arg Asp
1               5

<210> SEQ ID NO 68
<211> LENGTH: 8
<212> TYPE: PRT
<213> ORGANISM: Artificial sequence
<220> FEATURE:
<223> OTHER INFORMATION: TVA  CR

<400> SEQUENCE: 68

Trp Leu Cys Asp Gly His Pro Asp
1               5

<210> SEQ ID NO 69
<211> LENGTH: 44
<212> TYPE: PRT
<213> ORGANISM: Artificial sequence
<220> FEATURE:
<223> OTHER INFORMATION: LRP1CR3

<400> SEQUENCE: 69

Arg Pro Gln Cys Gln Pro Gly Glu Phe Ala Cys Ala Asn Ser Arg Cys
1               5                   10                  15

-continued

Ile Gln Glu Arg Trp Lys Cys Asp Gly Asp Asn Asp Cys Leu Asp Asn
            20                  25                  30

Ser Asp Glu Ala Pro Ala Leu Cys His Gln His Thr
        35                  40

<210> SEQ ID NO 70
<211> LENGTH: 41
<212> TYPE: PRT
<213> ORGANISM: Artificial sequence
<220> FEATURE:
<223> OTHER INFORMATION: LRP1CR4

<400> SEQUENCE: 70

Cys Pro Ser Asp Arg Phe Lys Cys Glu Asn Asn Arg Cys Ile Pro Asn
1               5                   10                  15

Arg Trp Leu Cys Asp Gly Asp Asn Asp Cys Gly Asn Ser Glu Asp Glu
            20                  25                  30

Ser Asn Ala Thr Cys Ser Ala Arg Thr
        35                  40

<210> SEQ ID NO 71
<211> LENGTH: 38
<212> TYPE: PRT
<213> ORGANISM: Artificial sequence
<220> FEATURE:
<223> OTHER INFORMATION: LRP1CR5

<400> SEQUENCE: 71

Cys Pro Pro Asn Gln Phe Ser Cys Ala Ser Gly Arg Cys Ile Pro Ile
1               5                   10                  15

Ser Trp Thr Cys Asp Leu Asp Asp Cys Gly Asp Arg Ser Asp Glu
            20                  25                  30

Ser Ala Ser Cys Ala Tyr
        35

<210> SEQ ID NO 72
<211> LENGTH: 42
<212> TYPE: PRT
<213> ORGANISM: Artificial sequence
<220> FEATURE:
<223> OTHER INFORMATION: VLDLRCR6

<400> SEQUENCE: 72

His Thr Lys Cys Pro Ala Ser Glu Ile Gln Cys Gly Ser Gly Glu Cys
1               5                   10                  15

Ile His Lys Lys Trp Arg Cys Asp Gly Asp Pro Asp Cys Lys Asp Gly
            20                  25                  30

Ser Asp Glu Val Asn Cys Pro Ser Arg Thr
        35                  40

<210> SEQ ID NO 73
<211> LENGTH: 40
<212> TYPE: PRT
<213> ORGANISM: Artificial sequence
<220> FEATURE:
<223> OTHER INFORMATION: VLDLRCR7

<400> SEQUENCE: 73

Cys Arg Pro Asp Gln Phe Glu Cys Glu Asp Gly Ser Cys Ile His Gly
1               5                   10                  15

Ser Arg Gln Cys Asn Gly Ile Arg Asp Cys Val Asp Gly Ser Asp Glu
            20                  25                  30

-continued

Val Asn Cys Lys Asn Val Asn Gln
            35                  40

<210> SEQ ID NO 74
<211> LENGTH: 42
<212> TYPE: PRT
<213> ORGANISM: Artificial sequence
<220> FEATURE:
<223> OTHER INFORMATION: VLDLRCR8

<400> SEQUENCE: 74

Cys Leu Gly Pro Gly Lys Phe Lys Cys Arg Ser Gly Glu Cys Ile Asp
1               5                   10                  15

Ile Ser Lys Val Cys Asn Gln Glu Gln Asp Cys Arg Asp Trp Ser Asp
            20                  25                  30

Glu Pro Leu Lys Glu Cys His Ile Asn Glu
            35                  40

<210> SEQ ID NO 75
<211> LENGTH: 36
<212> TYPE: PRT
<213> ORGANISM: Artificial sequence
<220> FEATURE:
<223> OTHER INFORMATION: MATCR1

<400> SEQUENCE: 75

Pro Cys Pro Gly Gln Phe Thr Cys Arg Thr Gly Arg Cys Ile Arg Lys
1               5                   10                  15

Glu Leu Arg Cys Asp Gly Trp Ala Asp Cys Thr Asp His Ser Asp Glu
            20                  25                  30

Leu Asn Cys Ser
        35

<210> SEQ ID NO 76
<211> LENGTH: 37
<212> TYPE: PRT
<213> ORGANISM: Artificial sequence
<220> FEATURE:
<223> OTHER INFORMATION: MATCR2

<400> SEQUENCE: 76

Cys Asp Ala Gly His Gln Phe Thr Cys Lys Asn Lys Phe Cys Lys Pro
1               5                   10                  15

Leu Phe Trp Val Cys Asp Ser Val Asn Asp Cys Gly Asp Asn Ser Asp
            20                  25                  30

Glu Gln Gly Cys Ser
        35

<210> SEQ ID NO 77
<211> LENGTH: 42
<212> TYPE: PRT
<213> ORGANISM: Artificial sequence
<220> FEATURE:
<223> OTHER INFORMATION: MATCR3

<400> SEQUENCE: 77

Cys Pro Ala Gln Thr Phe Arg Cys Ser Asn Gly Lys Cys Leu Ser Lys
1               5                   10                  15

Ser Gln Gln Cys Asn Gly Lys Asp Asp Cys Gly Asp Gly Ser Asp Glu
            20                  25                  30

Ala Ser Cys Pro Lys Val Asn Val Val Thr
            35                  40

```
<210> SEQ ID NO 78
<211> LENGTH: 37
<212> TYPE: PRT
<213> ORGANISM: Artificial sequence
<220> FEATURE:
<223> OTHER INFORMATION: MATCR4

<400> SEQUENCE: 78

Cys Thr Lys His Thr Tyr Arg Cys Leu Asn Gly Leu Cys Leu Ser Lys
1               5                   10                  15

Gly Asn Pro Glu Cys Asp Gly Lys Glu Asp Cys Ser Asp Gly Ser Asp
            20                  25                  30

Glu Lys Asp Cys Asp
            35

<210> SEQ ID NO 79
<211> LENGTH: 45
<212> TYPE: PRT
<213> ORGANISM: Artificial sequence
<220> FEATURE:
<223> OTHER INFORMATION: LRP2CR8

<400> SEQUENCE: 79

Pro Thr Glu Gln Cys Gly Leu Phe Ser Phe Pro Cys Lys Asn Gly Arg
1               5                   10                  15

Cys Val Pro Asn Tyr Tyr Leu Cys Asp Gly Val Asp Asp Cys His Asp
            20                  25                  30

Asn Ser Asp Glu Gln Leu Cys Gly Thr Leu Asn Asn Thr
            35                  40                  45

<210> SEQ ID NO 80
<211> LENGTH: 40
<212> TYPE: PRT
<213> ORGANISM: Artificial sequence
<220> FEATURE:
<223> OTHER INFORMATION: LRP2CR9

<400> SEQUENCE: 80

Cys Ser Ser Ser Ala Phe Thr Cys Gly His Gly Glu Cys Ile Pro Ala
1               5                   10                  15

His Trp Arg Cys Asp Lys Arg Asn Asp Cys Val Asp Gly Ser Asp Glu
            20                  25                  30

His Asn Cys Pro Thr His Ala Phe
            35                  40

<210> SEQ ID NO 81
<211> LENGTH: 41
<212> TYPE: PRT
<213> ORGANISM: Artificial sequence
<220> FEATURE:
<223> OTHER INFORMATION: LRP2CR27

<400> SEQUENCE: 81

Cys Arg Leu Gly Gln Phe Gln Cys Ser Asp Gly Asn Cys Thr Ser Pro
1               5                   10                  15

Gln Thr Leu Cys Asn Ala His Gln Asn Cys Pro Asp Gly Ser Asp Glu
            20                  25                  30

Asp Arg Leu Leu Cys Glu Asn His His
            35                  40

<210> SEQ ID NO 82
<211> LENGTH: 39
```

```
<212> TYPE: PRT
<213> ORGANISM: Artificial sequence
<220> FEATURE:
<223> OTHER INFORMATION: LRP2CR28

<400> SEQUENCE: 82

Cys Asp Ser Asn Glu Trp Gln Cys Ala Asn Lys Arg Cys Ile Pro Glu
1               5                   10                  15

Ser Trp Gln Cys Asp Thr Phe Asn Asp Cys Glu Asp Asn Ser Asp Glu
                20                  25                  30

Asp Ser Ser His Cys Ala Ser
            35

<210> SEQ ID NO 83
<211> LENGTH: 42
<212> TYPE: PRT
<213> ORGANISM: Artificial sequence
<220> FEATURE:
<223> OTHER INFORMATION: LRP2CR30

<400> SEQUENCE: 83

Leu Cys Asp Asn Phe Thr Glu Phe Ser Cys Lys Thr Asn Tyr Arg Cys
1               5                   10                  15

Ile Pro Lys Trp Ala Val Cys Asn Gly Val Asp Cys Arg Asp Asn
                20                  25                  30

Ser Asp Glu Gln Gly Cys Glu Glu Arg Thr
            35                  40

<210> SEQ ID NO 84
<211> LENGTH: 40
<212> TYPE: PRT
<213> ORGANISM: Artificial sequence
<220> FEATURE:
<223> OTHER INFORMATION: LRP2CR31

<400> SEQUENCE: 84

Cys His Pro Val Gly Asp Phe Arg Cys Lys Asn His His Cys Ile Pro
1               5                   10                  15

Leu Arg Trp Gln Cys Asp Gly Gln Asn Asp Cys Gly Asp Asn Ser Asp
                20                  25                  30

Glu Glu Asn Cys Ala Pro Arg Glu
            35                  40

<210> SEQ ID NO 85
<211> LENGTH: 45
<212> TYPE: PRT
<213> ORGANISM: Artificial sequence
<220> FEATURE:
<223> OTHER INFORMATION: LRP2CR34

<400> SEQUENCE: 85

Asp Gly Ala Tyr Cys Gln Ala Thr Met Phe Glu Cys Lys Asn His Val
1               5                   10                  15

Cys Ile Pro Pro Tyr Trp Lys Cys Asp Gly Asp Asp Cys Gly Asp
                20                  25                  30

Gly Ser Asp Glu Glu Leu His Leu Cys Leu Asp Val Pro
            35                  40                  45

<210> SEQ ID NO 86
<211> LENGTH: 45
<212> TYPE: PRT
<213> ORGANISM: Artificial sequence
<220> FEATURE:
```

<223> OTHER INFORMATION: LRP2CR35

<400> SEQUENCE: 86

Cys Asn Ser Pro Asn Arg Phe Arg Cys Asp Asn Asn Arg Cys Ile Tyr
1               5                   10                  15

Ser His Glu Val Cys Asn Gly Val Asp Asp Cys Gly Asp Gly Thr Asp
            20                  25                  30

Glu Thr Glu Glu His Cys Arg Lys Pro Thr Pro Lys Pro
        35                  40                  45

<210> SEQ ID NO 87
<211> LENGTH: 47
<212> TYPE: PRT
<213> ORGANISM: Artificial sequence
<220> FEATURE:
<223> OTHER INFORMATION: LRP2CR36

<400> SEQUENCE: 87

Cys Thr Glu Tyr Glu Tyr Lys Cys Gly Asn Gly His Cys Ile Pro His
1               5                   10                  15

Asp Asn Val Cys Asp Asp Ala Asp Cys Gly Asp Trp Ser Asp Glu
            20                  25                  30

Leu Gly Cys Asn Lys Gly Lys Glu Arg Thr Cys Ala Glu Asn Ile
        35                  40                  45

<210> SEQ ID NO 88
<211> LENGTH: 41
<212> TYPE: PRT
<213> ORGANISM: Artificial sequence
<220> FEATURE:
<223> OTHER INFORMATION: LRP6CR1

<400> SEQUENCE: 88

Pro Thr Cys Ser Pro Gln Gln Phe Thr Cys Phe Thr Gly Glu Ile Asp
1               5                   10                  15

Cys Ile Pro Val Ala Trp Arg Cys Asp Gly Phe Thr Glu Cys Glu Asp
            20                  25                  30

His Ser Asp Glu Leu Asn Cys Pro Val
        35                  40

<210> SEQ ID NO 89
<211> LENGTH: 38
<212> TYPE: PRT
<213> ORGANISM: Artificial sequence
<220> FEATURE:
<223> OTHER INFORMATION: LRP6CR2

<400> SEQUENCE: 89

Cys Ser Glu Ser Gln Phe Gln Cys Ala Ser Gly Gln Cys Ile Asp Gly
1               5                   10                  15

Ala Leu Arg Cys Asn Gly Asp Ala Asn Cys Gln Asp Lys Ser Asp Glu
            20                  25                  30

Lys Asn Cys Glu Val Leu
        35

<210> SEQ ID NO 90
<211> LENGTH: 38
<212> TYPE: PRT
<213> ORGANISM: Artificial sequence
<220> FEATURE:
<223> OTHER INFORMATION: LRP6CR3

<400> SEQUENCE: 90

Cys Leu Ile Asp Gln Phe Arg Cys Ala Asn Gly Gln Cys Ile Gly Lys
1               5                   10                  15

His Lys Lys Cys Asp His Asn Val Asp Cys Ser Asp Lys Ser Asp Glu
            20                  25                  30

Leu Asp Cys Tyr Pro Thr
            35

<210> SEQ ID NO 91
<211> LENGTH: 118
<212> TYPE: PRT
<213> ORGANISM: Artificial sequence
<220> FEATURE:
<223> OTHER INFORMATION: 8D6 CR12

<400> SEQUENCE: 91

Gly Ser Ser Cys Pro Pro Thr Lys Phe Gln Cys Arg Thr Ser Gly Leu
1               5                   10                  15

Cys Val Pro Leu Thr Trp Arg Cys Asp Arg Asp Leu Asp Cys Ser Asp
            20                  25                  30

Gly Ser Asp Glu Glu Cys Arg Ile Glu Pro Cys Thr Gln Lys Gly
            35                  40                  45

Gln Cys Pro Pro Pro Gly Leu Pro Cys Pro Cys Thr Gly Val Ser
50                  55                  60

Asp Cys Ser Gly Gly Thr Asp Lys Lys Leu Arg Asn Cys Ser Arg Leu
65                  70                  75                  80

Ala Cys Leu Ala Gly Glu Leu Arg Cys Thr Leu Ser Asp Asp Cys Ile
            85                  90                  95

Pro Leu Thr Trp Arg Cys Asp Gly His Pro Asp Cys Pro Asp Ser Ser
            100                 105                 110

Asp Glu Leu Gly Cys Gly
            115

<210> SEQ ID NO 92
<211> LENGTH: 119
<212> TYPE: PRT
<213> ORGANISM: Homo sapiens

<400> SEQUENCE: 92

Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Gln Gln Ser
            20                  25                  30

Ala Asn Leu Thr Asp Lys Glu Leu Glu Ala Phe Arg Glu Glu Leu Lys
            35                  40                  45

His Phe Glu Ala Lys Ile Glu Lys His Asn His Tyr Gln Lys Gln Leu
50                  55                  60

Glu Ile Ala His Glu Lys Leu Arg His Ala Glu Ser Val Gly Asp Gly
65                  70                  75                  80

Glu Arg Val Ser Arg Ser Arg Glu Lys His Ala Leu Leu Glu Gly Arg
            85                  90                  95

Thr Lys Glu Leu Gly Tyr Thr Val Lys Lys His Leu Gln Asp Leu Ser
            100                 105                 110

Gly Arg Ile Ser Arg Ala Arg
            115

<210> SEQ ID NO 93
<211> LENGTH: 119

<212> TYPE: PRT
<213> ORGANISM: Homo sapiens

<400> SEQUENCE: 93

```
Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Glu Gln Ser
            20                  25                  30

Ala Asn Leu Thr Asp Lys Glu Leu Glu Ala Phe Arg Glu Glu Leu Lys
        35                  40                  45

His Phe Lys Ala Lys Ile Glu Ala His Asn His Tyr Gln Lys Gln Leu
    50                  55                  60

Glu Ile Ala His Glu Asp Leu Arg His Ala Glu Ser Val Gly Asp Gly
65                  70                  75                  80

Glu Arg Val Ser Arg Ser Arg Glu Lys His Ala Leu Leu Glu Gly Arg
                85                  90                  95

Thr Lys Glu Leu Gly Tyr Thr Val Lys Lys His Leu Gln Asp Leu Ser
            100                 105                 110

Gly Arg Ile Ser Arg Ala Arg
        115
```

<210> SEQ ID NO 94
<211> LENGTH: 118
<212> TYPE: PRT
<213> ORGANISM: Homo sapiens

<400> SEQUENCE: 94

```
Gly Ser Ser Cys Pro Pro Thr Lys Phe Gln Cys Arg Thr Ser Gly Leu
1               5                   10                  15

Cys Val Pro Leu Thr Trp Arg Cys Asp Arg Asp Leu Asp Cys Ser Asp
            20                  25                  30

Gly Ser Asp Glu Glu Glu Cys Arg Ile Glu Pro Cys Thr Gln Lys Gly
        35                  40                  45

Gln Cys Pro Pro Pro Gly Leu Pro Cys Pro Cys Thr Gly Val Ser Asp
    50                  55                  60

Cys Ser Gly Gly Thr Asp Lys Lys Leu Arg Asn Cys Ser Arg Leu
65                  70                  75                  80

Ala Cys Leu Ala Gly Glu Leu Arg Cys Thr Leu Ser Asp Asp Cys Ile
                85                  90                  95

Pro Leu Thr Trp Arg Cys Asp Gly His Pro Asp Cys Pro Asp Ser Ser
            100                 105                 110

Asp Glu Leu Gly Cys Gly
        115
```

<210> SEQ ID NO 95
<211> LENGTH: 119
<212> TYPE: PRT
<213> ORGANISM: Artificial Sequence
<220> FEATURE:
<223> OTHER INFORMATION: Synthetic peptide

<400> SEQUENCE: 95

```
Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Glu Gln Ser
            20                  25                  30

Ala Asn Leu Thr Asp Lys Glu Leu Glu Ala Phe Arg Glu Glu Leu Lys
        35                  40                  45
```

```
His Phe Thr Ala Lys Ile Glu Ile His Asn His Tyr Gln Lys Gln Leu
            50                  55                  60

Glu Ile Ala His Glu Glu Leu Arg His Ala Glu Ser Val Gly Asp Gly
65                  70                  75                  80

Glu Arg Val Ser Arg Ser Arg Glu Lys His Ala Leu Leu Glu Gly Leu
                85                  90                  95

Thr Lys Glu Leu Gly Tyr Thr Val Lys Lys His Leu Gln Asp Leu Ser
                100                 105                 110

Gly Arg Ile Ser Arg Ala Arg
            115

<210> SEQ ID NO 96
<211> LENGTH: 119
<212> TYPE: PRT
<213> ORGANISM: Artificial Sequence
<220> FEATURE:
<223> OTHER INFORMATION: Synthetic peptide

<400> SEQUENCE: 96

Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Glu Gln Ser
                20                  25                  30

Ala Asn Leu Thr Asp Lys Glu Leu Glu Ala Phe Arg Glu Glu Leu Lys
            35                  40                  45

His Phe Ala Ala Lys Ile Glu Val Tyr Asn His Tyr Gln Lys Gln Leu
            50                  55                  60

Glu Phe Ala His Glu Trp Leu Arg His Ala Glu Ser Val Gly Asp Gly
65                  70                  75                  80

Glu Arg Val Ser Arg Ser Arg Glu Lys His Ala Leu Leu Glu Gly Arg
                85                  90                  95

Thr Lys Glu Leu Gly Tyr Thr Val Lys Lys His Leu Gln Asp Leu Ser
                100                 105                 110

Gly Arg Ile Ser Arg Ala Arg
            115

<210> SEQ ID NO 97
<211> LENGTH: 119
<212> TYPE: PRT
<213> ORGANISM: Artificial Sequence
<220> FEATURE:
<223> OTHER INFORMATION: Synthetic peptide

<400> SEQUENCE: 97

Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Glu Gln Ser
                20                  25                  30

Ala Asn Leu Thr Asp Lys Glu Leu Glu Ala Phe Arg Glu Glu Leu Lys
            35                  40                  45

His Phe Gly Ala Lys Ile Glu Arg His Asn His Tyr Gln Lys Gln Leu
            50                  55                  60

Glu Phe Ala His Glu Trp Leu Arg His Ala Glu Ser Val Gly Asp Ser
65                  70                  75                  80

Glu Arg Val Ser Arg Ser Arg Glu Lys His Ala Leu Leu Glu Gly Arg
                85                  90                  95

Thr Lys Glu Leu Gly Tyr Thr Val Lys Lys His Leu Gln Asp Leu Ser
```

Gly Arg Ile Ser Arg Ala Arg
        115

<210> SEQ ID NO 98
<211> LENGTH: 113
<212> TYPE: PRT
<213> ORGANISM: Artificial Sequence
<220> FEATURE:
<223> OTHER INFORMATION: Synthetic peptide

<400> SEQUENCE: 98

Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Glu Gln Ser
            20                  25                  30

Ala Asn Leu Thr Asp Lys Glu Leu Glu Ala Phe Arg Glu Glu Leu Lys
        35                  40                  45

His Phe Ala Ala Lys Ile Glu Ser His Asn His Tyr Gln Lys Gln Leu
    50                  55                  60

Glu Ile Ala His Glu Ser Met Arg His Ala Glu Ser Val Gly Tyr Gly
65                  70                  75                  80

Glu Arg Met Ser Arg Ser Arg Glu Lys His Ala Leu Leu Glu Gly Arg
                85                  90                  95

Thr Lys Glu Leu Gly Tyr Thr Val Thr Met His Leu Gln Asp Leu Ser
            100                 105                 110

Gly

<210> SEQ ID NO 99
<211> LENGTH: 49
<212> TYPE: PRT
<213> ORGANISM: Artificial Sequence
<220> FEATURE:
<223> OTHER INFORMATION: Synthetic peptide

<400> SEQUENCE: 99

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser

<210> SEQ ID NO 100
<211> LENGTH: 13
<212> TYPE: PRT
<213> ORGANISM: Artificial Sequence
<220> FEATURE:
<223> OTHER INFORMATION: Synthetic peptide

<400> SEQUENCE: 100

Lys Leu Ala Ala Ala Leu Glu His His His His His His
1               5                   10

<210> SEQ ID NO 101
<211> LENGTH: 5
<212> TYPE: PRT
<213> ORGANISM: Artificial Sequence
<220> FEATURE:
<223> OTHER INFORMATION: Synthetic peptide

<400> SEQUENCE: 101

Gly Pro Leu Gly Ser
1               5

<210> SEQ ID NO 102
<211> LENGTH: 172
<212> TYPE: PRT
<213> ORGANISM: Artificial Sequence
<220> FEATURE:
<223> OTHER INFORMATION: Synthetic peptide

<400> SEQUENCE: 102

Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser Leu Asp Arg Leu Arg Val Ser His Gln Gly Tyr Ser Thr Glu
    50                  55                  60

Ala Glu Phe Glu Glu Pro Arg Val Ile Asp Leu Trp Asp Leu Glu Gln
65                  70                  75                  80

Ser Ala Asn Leu Thr Asp Lys Glu Leu Glu Ala Phe Arg Glu Glu Leu
                85                  90                  95

Lys His Phe Ala Ala Lys Ile Glu Val Tyr Asn His Tyr Gln Lys Gln
            100                 105                 110

Leu Glu Phe Ala His Glu Trp Leu Arg His Ala Glu Ser Val Gly Asp
        115                 120                 125

Gly Glu Arg Val Ser Arg Ser Arg Glu Lys His Ala Leu Leu Glu Gly
    130                 135                 140

Arg Thr Lys Glu Leu Gly Tyr Thr Val Lys Lys His Leu Gln Asp Leu
145                 150                 155                 160

Ser Gly Arg Ile Ser Arg Ala Arg Ala Phe Ala Glu
                165                 170

<210> SEQ ID NO 103
<211> LENGTH: 162
<212> TYPE: PRT
<213> ORGANISM: Artificial Sequence
<220> FEATURE:
<223> OTHER INFORMATION: Synthetic peptide

<400> SEQUENCE: 103

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser Gly Tyr Ser Thr Glu Ala Glu Phe Glu Glu Pro Arg Val Ile Asp
    50                  55                  60

Leu Trp Asp Leu Glu Gln Ser Ala Asn Leu Thr Asp Lys Glu Leu Glu
65                  70                  75                  80

Ala Phe Arg Glu Glu Leu Lys His Phe Ala Ala Lys Ile Glu Val Tyr
                85                  90                  95

Asn His Tyr Gln Lys Gln Leu Glu Phe Ala His Glu Trp Leu Arg His
            100                 105                 110

```
Ala Glu Ser Val Gly Asp Gly Glu Arg Val Ser Arg Ser Arg Glu Lys
            115                 120                 125

His Ala Leu Leu Glu Gly Arg Thr Lys Glu Leu Gly Tyr Thr Val Lys
            130                 135                 140

Lys His Leu Gln Asp Leu Ser Gly Arg Ile Ser Arg Ala Arg Ala Phe
145                 150                 155                 160

Ala Glu

<210> SEQ ID NO 104
<211> LENGTH: 141
<212> TYPE: PRT
<213> ORGANISM: Artificial Sequence
<220> FEATURE:
<223> OTHER INFORMATION: Synthetic peptide

<400> SEQUENCE: 104

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser Ser Ala Asn Leu Thr Asp Lys Glu Leu Glu Ala Phe Arg Glu Glu
50                  55                  60

Leu Lys His Phe Ala Ala Lys Ile Glu Val Tyr Asn His Tyr Gln Lys
65                  70                  75                  80

Gln Leu Glu Phe Ala His Glu Trp Leu Arg His Ala Glu Ser Val Gly
                85                  90                  95

Asp Gly Glu Arg Val Ser Arg Ser Arg Glu Lys His Ala Leu Leu Glu
            100                 105                 110

Gly Arg Thr Lys Glu Leu Gly Tyr Thr Val Lys Lys His Leu Gln Asp
            115                 120                 125

Leu Ser Gly Arg Ile Ser Arg Ala Arg Ala Phe Ala Glu
        130                 135                 140

<210> SEQ ID NO 105
<211> LENGTH: 130
<212> TYPE: PRT
<213> ORGANISM: Artificial Sequence
<220> FEATURE:
<223> OTHER INFORMATION: Synthetic peptide

<400> SEQUENCE: 105

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser Phe Arg Glu Glu Leu Lys His Phe Ala Ala Lys Ile Glu Val Tyr
50                  55                  60

Asn His Tyr Gln Lys Gln Leu Glu Phe Ala His Glu Trp Leu Arg His
65                  70                  75                  80

Ala Glu Ser Val Gly Asp Gly Glu Arg Val Ser Arg Ser Arg Glu Lys
                85                  90                  95

His Ala Leu Leu Glu Gly Arg Thr Lys Glu Leu Gly Tyr Thr Val Lys
            100                 105                 110
```

Lys His Leu Gln Asp Leu Ser Gly Arg Ile Ser Arg Ala Arg Ala Phe
            115                 120                 125

Ala Glu
    130

<210> SEQ ID NO 106
<211> LENGTH: 120
<212> TYPE: PRT
<213> ORGANISM: Artificial Sequence
<220> FEATURE:
<223> OTHER INFORMATION: Synthetic peptide

<400> SEQUENCE: 106

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser Lys Ile Glu Arg His Asn His Tyr Gln Lys Gln Leu Glu Phe Ala
    50                  55                  60

His Glu Trp Leu Arg His Ala Glu Ser Val Gly Asp Gly Glu Arg Val
65                  70                  75                  80

Ser Arg Ser Arg Glu Lys His Ala Leu Leu Glu Gly Arg Thr Lys Glu
                85                  90                  95

Leu Gly Tyr Thr Val Lys Lys His Leu Gln Asp Leu Ser Gly Arg Ile
            100                 105                 110

Ser Arg Ala Arg Ala Phe Ala Glu
        115                 120

<210> SEQ ID NO 107
<211> LENGTH: 116
<212> TYPE: PRT
<213> ORGANISM: Artificial Sequence
<220> FEATURE:
<223> OTHER INFORMATION: Synthetic peptide

<400> SEQUENCE: 107

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser His Asn His Tyr Gln Lys Gln Leu Glu Phe Ala His Glu Trp Leu
    50                  55                  60

Arg His Ala Glu Ser Val Gly Asp Gly Glu Arg Val Ser Arg Ser Arg
65                  70                  75                  80

Glu Lys His Ala Leu Leu Glu Gly Arg Thr Lys Glu Leu Gly Tyr Thr
                85                  90                  95

Val Lys Lys His Leu Gln Asp Leu Ser Gly Arg Ile Ser Arg Ala Arg
            100                 105                 110

Ala Phe Ala Glu
        115

<210> SEQ ID NO 108
<211> LENGTH: 108
<212> TYPE: PRT

```
<213> ORGANISM: Artificial Sequence
<220> FEATURE:
<223> OTHER INFORMATION: Synthetic peptide

<400> SEQUENCE: 108

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser Glu Phe Ala His Glu Trp Leu Arg His Ala Glu Ser Val Gly Asp
    50                  55                  60

Gly Glu Arg Val Ser Arg Ser Arg Glu Lys His Ala Leu Leu Glu Gly
65                  70                  75                  80

Arg Thr Lys Glu Leu Gly Tyr Thr Val Lys Lys His Leu Gln Asp Leu
                85                  90                  95

Ser Gly Arg Ile Ser Arg Ala Arg Ala Phe Ala Glu
            100                 105

<210> SEQ ID NO 109
<211> LENGTH: 105
<212> TYPE: PRT
<213> ORGANISM: Artificial Sequence
<220> FEATURE:
<223> OTHER INFORMATION: Synthetic peptide

<400> SEQUENCE: 109

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser His Glu Trp Leu Arg His Ala Glu Ser Val Gly Asp Gly Glu Arg
    50                  55                  60

Val Ser Arg Ser Arg Glu Lys His Ala Leu Leu Glu Gly Arg Thr Lys
65                  70                  75                  80

Glu Leu Gly Tyr Thr Val Lys Lys His Leu Gln Asp Leu Ser Gly Arg
                85                  90                  95

Ile Ser Arg Ala Arg Ala Phe Ala Glu
            100                 105

<210> SEQ ID NO 110
<211> LENGTH: 139
<212> TYPE: PRT
<213> ORGANISM: Artificial Sequence
<220> FEATURE:
<223> OTHER INFORMATION: Synthetic peptide

<400> SEQUENCE: 110

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser Phe Arg Glu Glu Leu Lys His Phe Ala Ala Lys Ile Glu Val Tyr
    50                  55                  60
```

Asn His Tyr Gln Lys Gln Leu Glu Phe Ala His Glu Trp Leu Arg His
65                  70                  75                  80

Ala Glu Ser Val Gly Asp Gly Glu Arg Val Ser Arg Ser Arg Glu Lys
                85                  90                  95

His Ala Leu Leu Glu Gly Arg Thr Lys Glu Leu Gly Tyr Thr Val Lys
            100                 105                 110

Lys His Leu Gln Asp Leu Ser Gly Arg Ile Ser Arg Ala Arg Lys Leu
        115                 120                 125

Ala Ala Ala Leu Glu His His His His His
    130                 135

<210> SEQ ID NO 111
<211> LENGTH: 133
<212> TYPE: PRT
<213> ORGANISM: Artificial Sequence
<220> FEATURE:
<223> OTHER INFORMATION: Synthetic peptide

<400> SEQUENCE: 111

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser Phe Arg Glu Glu Leu Lys His Phe Ala Ala Lys Ile Glu Val Tyr
    50                  55                  60

Asn His Tyr Gln Lys Gln Leu Glu Phe Ala His Glu Trp Leu Arg His
65                  70                  75                  80

Ala Glu Ser Val Gly Asp Gly Glu Arg Val Ser Arg Ser Arg Glu Lys
                85                  90                  95

His Ala Leu Leu Glu Gly Arg Thr Lys Glu Leu Gly Tyr Thr Val Lys
            100                 105                 110

Lys His Leu Gln Asp Leu Ser Gly Lys Leu Ala Ala Ala Leu Glu His
        115                 120                 125

His His His His
    130

<210> SEQ ID NO 112
<211> LENGTH: 114
<212> TYPE: PRT
<213> ORGANISM: Artificial Sequence
<220> FEATURE:
<223> OTHER INFORMATION: Synthetic peptide

<400> SEQUENCE: 112

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser Phe Arg Glu Glu Leu Lys His Phe Ala Ala Lys Ile Glu Val Tyr
    50                  55                  60

Asn His Tyr Gln Lys Gln Leu Glu Phe Ala His Glu Trp Leu Arg His
65                  70                  75                  80

Ala Glu Ser Val Gly Asp Gly Glu Arg Val Ser Arg Ser Arg Glu Lys

His Ala Leu Leu Glu Lys Leu Ala Ala Ala Leu Glu His His His His
            100                 105                 110

His His

<210> SEQ ID NO 113
<211> LENGTH: 106
<212> TYPE: PRT
<213> ORGANISM: Artificial Sequence
<220> FEATURE:
<223> OTHER INFORMATION: Synthetic peptide

<400> SEQUENCE: 113

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser Phe Arg Glu Glu Leu Lys His Phe Ala Ala Lys Ile Glu Val Tyr
    50                  55                  60

Asn His Tyr Gln Lys Gln Leu Glu Phe Ala His Glu Trp Leu Arg His
65                  70                  75                  80

Ala Glu Ser Val Gly Asp Gly Glu Arg Val Ser Arg Ser Lys Leu Ala
                85                  90                  95

Ala Ala Leu Glu His His His His His His
            100                 105

<210> SEQ ID NO 114
<211> LENGTH: 96
<212> TYPE: PRT
<213> ORGANISM: Artificial Sequence
<220> FEATURE:
<223> OTHER INFORMATION: Synthetic peptide

<400> SEQUENCE: 114

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Lys Ala Met Ala Asp Ile Gly
        35                  40                  45

Ser Phe Arg Glu Glu Leu Lys His Phe Ala Ala Lys Ile Glu Val Tyr
    50                  55                  60

Asn His Tyr Gln Lys Gln Leu Glu Phe Ala His Glu Trp Leu Arg His
65                  70                  75                  80

Ala Glu Ser Lys Leu Ala Ala Ala Leu Glu His His His His His
                85                  90                  95

<210> SEQ ID NO 115
<211> LENGTH: 57
<212> TYPE: DNA
<213> ORGANISM: Artificial Sequence
<220> FEATURE:
<223> OTHER INFORMATION: Synthetic nucleotide

<400> SEQUENCE: 115
gcgataggat ccttctgccg actgggacag ttccagtgca gtgacggcaa ctgcacc        57

<210> SEQ ID NO 116
<211> LENGTH: 58
<212> TYPE: DNA
<213> ORGANISM: Artificial Sequence
<220> FEATURE:
<223> OTHER INFORMATION: Synthetic nucleotide

<400> SEQUENCE: 116
gcgataaagc ttctattagc tggcacagtg ggaactgtct tcatctgagt tatcctca    58

<210> SEQ ID NO 117
<211> LENGTH: 57
<212> TYPE: DNA
<213> ORGANISM: Artificial Sequence
<220> FEATURE:
<223> OTHER INFORMATION: Synthetic nucleotide

<400> SEQUENCE: 117
gcgataggat ccctctgtga caacttcaca gaattcagct gcaaacaaa ttaccgc    57

<210> SEQ ID NO 118
<211> LENGTH: 45
<212> TYPE: DNA
<213> ORGANISM: Artificial Sequence
<220> FEATURE:
<223> OTHER INFORMATION: Synthetic nucleotide

<400> SEQUENCE: 118
gcgataaagc ttttatcact cccggggagc acagttttcc tcatc    45

<210> SEQ ID NO 119
<211> LENGTH: 53
<212> TYPE: DNA
<213> ORGANISM: Artificial Sequence
<220> FEATURE:
<223> OTHER INFORMATION: Synthetic nucleotide

<400> SEQUENCE: 119
gcgataggat ccagttgtcc ggcccagacc ttcaggtgtt ccaatgggaa gtg    53

<210> SEQ ID NO 120
<211> LENGTH: 43
<212> TYPE: DNA
<213> ORGANISM: Artificial Sequence
<220> FEATURE:
<223> OTHER INFORMATION: Synthetic nucleotide

<400> SEQUENCE: 120
gcgataaagc ttttatcaac tgcaccctg ctcgtcgctg ttg    43

<210> SEQ ID NO 121
<211> LENGTH: 323
<212> TYPE: PRT
<213> ORGANISM: Homo sapiens

<400> SEQUENCE: 121

Tyr Ser Arg Glu Lys Asn Gln Pro Lys Pro Ser Pro Lys Arg Glu Ser
1               5                   10                  15

Gly Glu Glu Phe Arg Met Glu Lys Leu Asn Gln Leu Trp Glu Lys Ala
            20                  25                  30

Gln Arg Leu His Leu Pro Pro Val Arg Leu Ala Glu Leu His Ala Asp
        35                  40                  45

Leu Lys Ile Gln Glu Arg Asp Glu Leu Ala Trp Lys Lys Leu Lys Leu
    50                  55                  60

```
Asp Gly Leu Asp Glu Asp Gly Glu Lys Glu Ala Arg Leu Ile Arg Asn
 65                  70                  75                  80

Leu Asn Val Ile Leu Ala Lys Tyr Gly Leu Asp Gly Lys Lys Asp Ala
                 85                  90                  95

Arg Gln Val Thr Ser Asn Ser Leu Ser Gly Thr Gln Glu Asp Gly Leu
                100                 105                 110

Asp Asp Pro Arg Leu Glu Lys Leu Trp His Lys Ala Lys Thr Ser Gly
            115                 120                 125

Lys Phe Ser Gly Glu Glu Leu Asp Lys Leu Trp Arg Glu Phe Leu His
        130                 135                 140

His Lys Glu Lys Val His Glu Tyr Asn Val Leu Leu Glu Thr Leu Ser
145                 150                 155                 160

Arg Thr Glu Glu Ile His Glu Asn Val Ile Ser Pro Ser Asp Leu Ser
                165                 170                 175

Asp Ile Lys Gly Ser Val Leu His Ser Arg His Thr Glu Leu Lys Glu
                180                 185                 190

Lys Leu Arg Ser Ile Asn Gln Gly Leu Asp Arg Leu Arg Arg Val Ser
            195                 200                 205

His Gln Gly Tyr Ser Thr Glu Ala Glu Phe Glu Glu Pro Arg Val Ile
        210                 215                 220

Asp Leu Trp Asp Leu Ala Gln Ser Ala Asn Leu Thr Asp Lys Glu Leu
225                 230                 235                 240

Glu Ala Phe Arg Glu Glu Leu Lys His Phe Glu Ala Lys Ile Glu Lys
                245                 250                 255

His Asn His Tyr Gln Lys Gln Leu Glu Ile Ala His Glu Lys Leu Arg
                260                 265                 270

His Ala Glu Ser Val Gly Asp Gly Glu Arg Val Ser Arg Ser Arg Glu
            275                 280                 285

Lys His Ala Leu Leu Glu Gly Arg Thr Lys Glu Leu Gly Tyr Thr Val
        290                 295                 300

Lys Lys His Leu Gln Asp Leu Ser Gly Arg Ile Ser Arg Ala Arg His
305                 310                 315                 320

Asn Glu Leu
```

COMPOSITIONS COMPRISING RECEPTOR-ASSOCIATED PROTEIN (RAP) VARIANTS SPECIFIC FOR CR-CONTAINING PROTEINS AND USES THEREOF

FIELD OF THE INVENTION

The present invention relates to receptor-selective variants of the low-density lipoprotein receptor-associated protein (RAP) and compositions thereof, methods of generating such variants and methods of using such receptor-selective RAP variant compositions for therapeutic purposes. The invention also relates to antibodies that bind selectively to one or a small subset of complement-type repeat (CR)-containing proteins.

BACKGROUND OF THE INVENTION

The low-density lipoprotein receptor domain class A, or complement-type repeat (CR), constitutes a large family of conserved protein sequences. Structural data on members of this family suggests that CR sequences adopt a characteristic fold, the LDL receptor-like module (Structural Classification of Proteins, SCOP, terminology). CR sequences are found in a variety of different types of proteins including the low density lipoprotein receptor family and the type II transmembrane serine protease (matriptase) family. The LDLR are a family of cell-surface, transmembrane proteins that mediate a wide variety of physiological phenomena. Mechanisms of action include both trafficking of bound ligands and signal transduction from the extracellular space (1). The LDLR participate in various cellular functions, including but not limited to the metabolism of lipoproteins (2, 3), control of matrix metalloproteases and coagulation factors (4-6), specification of cell fate (3, 7), guidance of neural cell migration (7, 8), induction of proliferation in tumor cells (9, 10), binding of rhinovirus (11, 12), signalling by neurotransmitters (13, 14), acquisition of antigens by antigen presenting cells (15), trancytosis of ligands across the blood-brain barrier (16-19), recovery of proteins from glomerular filtrate (20), transport of endocrine hormones (21), efflux of amyloid β peptide from the brain (22), activation of bone deposition (23) and regulation of endothelial cell proliferation (24). The capacity of the LDLR to serve in so many roles derives in part from the diverse set of ligands to which these receptors are able to bind. Another feature of this receptor family is the diverse, and often unique, tissue distribution patterns of each LDLR. The type II transmembrane serine protease family includes corin and the matriptases ST14, matriptase-2 and matriptase-3. Matriptase (MT-SP1, ST14, TADG-15) is overexpressed in a variety of epithelial tumors (carcinomas) (25-33). Following transactivation induced by hepatocyte activator inhibitor-1 (HAI-1), matriptase promotes tumor growth and metastasis by degrading extracellular matrix components directly or by activating other proteases, such as urokinase plasminogen activator (uPA), resulting in matrix-degradative events (26, 34, 35). In addition to the LDLR and matriptase families, a variety of other proteins have CR domains. One such protein, the FDC-8D6 antigen (CD320) has a pair of such domains and plays an important role in B-cell differentiation in lymphatic follicles (36, 37).

The important roles that CR-containing proteins play in pathophysiological processes, along with the unique tissue-distribution profiles of some members of these families, make these proteins useful drug targets. Protein-selective drugs could directly impact the function of a targeted protein, diminishing the supporting effects that the protein has on a particular disease state. Alternatively, the drug could take advantage of the tissue distribution of the targeted protein to efficiently deliver other therapeutic molecules to a particular tissue affected by a disease. Despite considerable evidence of the importance of CR-containing proteins in mammalian physiology and pathophysiology, there are few examples of drugs that act selectively on particular members of the LDLR or CR-containing protein families. The ability to create molecules that bind specific members of these families would provide a means of developing such drugs.

Thus, there exists a need for agents with improved ability to bind selectively to specific receptors including but not limited to members of the LDLR and type II transmembrane serine protease families, either to directly affect the behavior of these CR-containing proteins through the selective binding event or to facilitate delivery of a therapeutic agent to its site of action through the selective binding event.

One example where such receptor-selective molecules might be valuable is in the delivery of therapeutic molecules to the brain. There are approximately 4.5 million people in the US suffering from Alzheimer's disease, and another million with Parkinson's disease. Protein therapeutics for both disorders have shown promise in pre-clinical trials, but obstacles related to drug delivery have slowed development of these drugs (38, 39). The blood-brain barrier (BBB) is a physical and metabolic barrier that separates the peripheral circulation from the central nervous system (CNS). While the BBB serves to protect the microenvironment of the brain, it also presents a challenge to the delivery of therapeutic drugs to the CNS (40, 41). Vehicle-mediated delivery has been widely explored as a means of protein-based drug delivery, but progress to date has been limited. Megalin is expressed on the BBB and there is evidence suggesting that this receptor can mediate transport of ligands into the brain. The best characterized ligands for megalin, including RAP and a variety of lipoproteins, may also exhibit nonspecific binding to other LDLR or are present at saturating levels in blood, competing with the binding of therapeutics. More selective ligands for megalin, molecules with no significant competition from endogenous ligands, would have improved trans-barrier transport properties.

Similarly, the VLDLR has been shown to be expressed on brain capillary endothelium and to mediate transport of lipoprotein lipase across the endothelium of the aorta (Wyne, et al. (1996) Arterioscler Thromb Vasc Biol 16, 407-415; Obunike, et al. (2001) J Biol Chem 276, 8934-8941). Molecules that selectively bind to VLDLR or fusions containing drugs conjugated to such molecules might be expected to have enhanced distribution to the brain. There are potential applications for VLDLR-selective agents outside of brain delivery. The VLDLR has also been implicated in foam cell formation by mediating uptake of excess free fatty acids (FFA) into vascular macrophages (Hiltunen, et al., (1998) Circulation 97, 1079-1086; Qu, et al., (2004) J Huazhong Univ Sci Technolog Med Sci 24, 1-4, 8). Molecules that selectively bind to VLDLR might be developed to block association of lipoprotein particles with macrophages and inhibit foam cell formation. Such molecules would also be expected to limit transfer of FFA from circulating lipoprotein into adipocytes, slowing the progression toward obesity in susceptible subjects (Goudriaan, et al. (2001) Arterioscler Thromb Vasc Biol 21, 1488-1493; Goudriaan, et al. (2004) J Lipid Res 45, 1475-1481; Tacken, et al. (2001) Curr Opin Lipidol 12, 275-279; Yagyu, et al., (2002) J Biol Chem 277, 10037-10043). The high level of expression of VLDLR on the luminal surface of muscle endothelium, along with the low level of expression of VLDLR in liver, would be expected to drive distribution of VLDLR-selective RAP variants to muscle tissue after intravenous administration. Molecules with therapeutic effects on muscle tissue could be attached to VLDLR-selective agents to improve distribution of such molecules to muscle.

Treatments for other diseases may also be developed using ligands with enhanced selectivity for particular CR domains or combinations of CR domains. Overexpression of at least two LDLR, LRP5, LRP6, as well as matriptase (MT-ST1, ST14, TADG-15), has been associated with increased tumorigenicity of the affected tissue (Li, et al., (2004) Oncogene 23, 9129-9135; Hoang, et al., (2004) Int J Cancer 109, 106-111; Tanimoto, et al., (2005) Br J Cancer 92, 278-283; Santin, et al., (2004) Int J Cancer 112, 14-25; Santin, et al., (2003) Cancer 98, 1898-1904; Tanimoto, et al., (2001) Tumour Biol 22, 104-114). Molecules that bind to these proteins may provide a means of diminishing their tumorigenic effects, especially by interfering with their functions directly or but also potentially by targeting tissues that overexpress these proteins with anti-tumor drugs attached to the selective molecule. Matriptase is anchored in the lateral or basolateral membranes of epithelial cells through an N-terminal type II transmembrane domain (42). The membrane-embedded sequence is followed by an extracellular SEA domain, two CUB domains, four CR domains and a trypsin domain at the C-terminus of the protein. Mutagenesis of the CR sequences within matriptase results in a failure of the resulting protease mutant to become activated (43). Similarly, an antibody that binds to the third CR domain of matriptase blocks activation of the enzyme (44). A RAP variant with affinity for one of the two CR pairs within matriptase that include the third CR domain would be expected to interfere with proteolytic activation, in a manner similar to the observed inhibition by the antibody to this region. Such a variant would be expected to diminish the metastatic and tumorigenic effects of matriptase overexpression in affected tissues.

There are approximately eight million women in the US with osteoporosis. Enhanced Wnt signaling through the LDLR LRP5 has been demonstrated to increase osteoblast differentiation, inhibit osteoclast activity and enhance bone deposition (Westendorf, et al. (2004) Gene 341, 19-39; Zhang, et al., (2004) Mol Cell Biol 24, 4677-4684; Mizuguchi, et al. (2004) J Hum Genet. 49, 80-86). This mechanism has been validated with osteoblast-specific APC (adenomatous polyposis coli) knockout mice and with LRP5 mutants that are insensitive to DKK (Dickkopf)-1 and sclerostin-mediated inhibition (Zhang, et al., (2004) Mol Cell Biol 24, 4677-4684; Holmen, et al. (2005) J Biol Chem). Intravenously-administered molecules that selectively bind LRP5 and interfere with inhibitor binding to LRP5 or otherwise enhance Wnt signaling through LRP5, might counter the effects of osteoporosis. Such molecules are not currently available.

Non-Hodgkin's lymphoma (NHL) involves the proliferation and extranodal migration of a class of immune cells called B-cells. NHL is the leading cause of death from cancer in males between the ages of 20 and 39. Studies have shown that the FDC-8D6 antigen protein (CD320) facilitates neoplastic B-cell growth (36, 37). 8D6 antigen contains a single pair of CR domains. Agents, such as RAP variants, that bind to and block the function of 8D6 antigen might then be expected to slow the progression of non-Hodgkin's lymphoma in humans.

Given the widespread participation of CR-containing proteins throughout mammalian physiology, polypeptides with binding-selectivity for particular CR domains have many possible pharmaceutical applications.

SUMMARY OF THE INVENTION

The invention relates to RAP variants and derivatives that selectively bind a specific complement type repeat-containing protein, or small subset of CR-containing proteins; and uses of such variants as inhibitors or enhancers of such CR-containing proteins, and uses of such variants for the targeted delivery of diagnostic or therapeutic agents to tissues expressing such CR-containing proteins.

In one aspect, the invention provides a receptor-binding polypeptide moiety (also referred to herein as a RAP variant) that is a variant of the alpha-2-macroglobulin/low density lipoprotein receptor-related protein-associated protein 1 (RAP, Uniprot accession P30533, Pfam accession numbers PF06400 and PF06401) with selective binding affinities for a unique protein or subset of proteins that contain complement-type repeats (CR). The present invention contemplates RAP sequence variants that have binding complementarity for CR pairs that are not bound with high affinity by wild-type RAP and which are found in either one particular LDLR or other CR-containing protein (i.e. are unique) or which are found within a small subset of LDLR or other CR-containing proteins (e.g., are infrequent with a representation of less than 10% in the proteome). In one embodiment, the RAP variant is not specific for the LRP2 protein.

The RAP variant molecule may constitute a portion of full-length human RAP. In one embodiment the RAP variant is missing at least 200 and up to 243 amino acids from the N-terminus. In a related embodiment, the RAP variant of further is missing up to 11 amino acids from the C-terminus, and may further be missing at least 4 amino acids from the C-terminus. In another embodiment the RAP variant comprises a continuous portion of mature RAP that is (a) at least 71 amino acids in length and (b) comprises amino acids 256-270. In a related embodiment, the RAP variant comprises a continuous portion of RAP d3 that is (a) at least 71 amino acids in length and (b) comprises amino acids 256-270.

In one embodiment, the RAP variant exhibits binding selectivity (i.e. binds with higher affinity to a particular protein compared to other CR-containing proteins) for a protein selected from the group consisting of LDLR (P01130), LRP1 (P98157), LRP1B (Q9NZR2), LRP2 (P98164), LRP3 (O75074), LRP4 (O75096), LRP5 (O75197), LRP6 (O75581), LRP8 (Q14114), Sortilin (Q92673), LRP10 (Q7Z4F1), LRP11 (Q86VZ4), LRP12 (Q9Y561), FDC-8D6 (CD320), VLDLR (P98155), TADG-15 (ST14, Q8WVC1), TMPS3 (P57727), TNPS4 (Q9NRS4), TMPS6 (Q8IU80), Q6ICC2, Q6PJ72, Q76B61, Q7RTY8, Q7Z7K9, Q86YD5, Q8NAN7, Q8NBJ0, Q8WW88, Q96NT6, Q9BYE1, Q9BYE2, Q9NPF0 and corin (Q8IZR7). In particular, the RAP variant has protein-binding selectivity different from that of RAP. The invention contemplates preparation of RAP variants exhibiting altered affinity to any of these CR-containing proteins or receptors. The uses of the RAP variants that are selective for particular CR-containing proteins or receptors are dictated by the function of the CR-containing proteins or receptors. Receptor-selective RAP variants thus provides a means of modifying and exploiting specific LDLR, or other CR-containing proteins, in vivo.

The RAP variant differs from RAP through one or more mutations in its polypeptide sequence. In one embodiment, the RAP variants have mutations within the third domain (d3) of RAP. RAP d3 comprises amino acids 200-323 of mature RAP (Uniprot P30533) and amino acids 234-357 of precursor RAP (Uniprot P30533). In preferred embodiments, the variant is a receptor-selective variant that comprises a mutation at one, two, three, four, five, or six or more positions within any one of the regions selected from: amino acids 200-319, 300-319, or 247-257 of RAP of the mature form of the sequence set forth in Uniprot Accession No. P30533. In more preferred embodiments, the polypeptide comprising a RAP variant comprises a mutation at one, two, three, four, five, six or more positions selected from the group consisting of 175, 205, 213, 217, 226, 230, 232, 239, 246, 249, 251, 256, 257, 261, 266, 267, 268, 270, 273, 287, 290, 294, 296, 297, 298, 305, 312, 313. of mature P30533. In a still further embodiment, the polypeptide comprises a mutation at three or more of the following positions: 205, 217, 249, 251, 256, 257, 266, 270, 294, 296, 297, 305. In one embodiment, RAP variants contain at least one mutation at positions 251, 256 and 270 of mature RAP.

In one aspect, the RAP variant binds selectively to a matriptase protein. It is contemplated that the matriptase-specific variant contains a mutation at any one of positions 251, 256, 257, 266, 270 or 280 of RAP. It is further contemplated that the matriptase-specific RAP variants contain at least one, two, three, four, five or six mutations at positions 251, 256, 257, 266, 270 and 280 of mature RAP In a related aspect, the RAP variant binds selectively to a VLDLR protein. It is contemplated that the VLDLR-specific variant contains a mutation at any one of positions 251, 256, 270 or 296 of RAP. It is further contemplated that the VLDLR-specific RAP variants contain at least one, two, three, or four mutations at positions 251, 256, 270 and 296 of mature RAP.

In a further aspect, the RAP variant binds selectively to an FDC-8D6 (CD320) protein. It is contemplated that the FDC-8D6-specific variant contains a mutation at any one of positions 251, 256, 270, 279 or 305 of RAP. It is further contemplated that the FDC-8D6-specific RAP variants contain at least one, two, three, four or five mutations at positions 251, 256, 270, 279 and 305 of mature RAP.

Any of the preceding mutations may include replacement of an amino acid from the acidic group (D, E) with an amino acid from the basic group (K, R), or vice versa. Any of the preceding mutations may also include replacement of an amino acid from the group (A, C, D, E, G, I, K, L, M, N, P, Q, R, S, T, V) with an amino acid from the group (F, Y, W, H). In a further embodiment, the polypeptide comprises three, four, five, six or more of the following mutations: V175L, R205S, S213T, E217K, L226M, H249Y, E230V, S232P, E239G, E246G, E251L, E251K, E251T, E251G, E251P, E251N, E251R, K256R, K256V, K256A, K256I, K256P, K256L, I266F, I266T, K257Y, Q261R, A267V, H268R, K270P, K270D, K270N, K270G, K270E, K270W, L271M, H273Y, D279Y, V283M, R287H, I1290Y, H290L, E294V, R296L, T297I, K298R, K305T, K306M, S312F, G313D., compared to the mature form of RAP (P30533).

In another embodiment, it is contemplated that the polypeptide comprises a RAP variant that lacks at least amino acids 1-143 of RAP of mature P30533. In yet another embodiment, the polypeptide lacks up to 4 of the C-terminal amino acids of RAP of mature P30533.

In another aspect, the invention provides preparation of antibodies exhibiting selective binding affinity to a CR domain of these CR-containing proteins or receptors. The CR domain is preferably unique (i.e. found only in that CR-containing protein compared to other members of the family of CR-containing proteins), or is found in less than 10% of CRs derived from all the CRs in the proteome of an animal. A number of such unique or selective CR domains within CR-containing proteins are described herein. The subset of antibodies that bind to one of such CR domains (also referred to as "CR-specific antibodies") are expected to exhibit higher selectivity for particular CR-containing proteins. The uses of the antibodies that are selective for particular CR-containing proteins or receptors are dictated by the function of the CR-containing proteins or receptors. CR-specific antibodies thus provide a means of modifying and exploiting specific LDLR, or other CR-containing proteins, in vivo.

Antibodies of the invention preferably bind one CR-containing protein (or a subset of CR-containing proteins) with substantially greater affinity than another member of the CR-containing protein family, e.g. at least 1.5-fold, 2-fold, 2.5-fold, 3-fold, 4-fold, 5-fold, 7-fold, 10-fold, 20-fold or higher affinity, and preferably bind to a CR-containing protein (or a subset) with substantially greater affinity than at least 1, 2, 3, 4, 5, 6, 7, or 8 other members of the family. In a related aspect, the antibodies may be specific for a CR domain within a CR containing protein described herein. Said CR-specific antibodies of the invention preferably bind a CR domain in a CR-containing protein (or a subset of CR-containing proteins) with substantially greater affinity than another CR domain found in a related member of the CR-containing protein family. In one aspect, antibodies of the invention are specific for at least one of the CR domains set out in SEQ ID NO: 69-91. Antibodies contemplated by the invention include full length antibodies, monoclonal antibodies, polyclonal antibodies, multispecific antibodies (e.g., bispecific antibodies), antibody fragments that can bind antigen (e.g., Fab', F'(ab)2, Fv, single chain antibodies, diabodies, complementarity determining region (CDR) fragments), and recombinant peptides comprising the forgoing as long as they exhibit the desired biological activity.

In addition to RAP variants alone, the invention contemplates oligomeric combinations of RAP domains or variants of RAP domains, or combinations of RAP variants and CR-specific antibodies that comprise novel binding and effector functions. A fusion system has been created for combining RAP d3 sequences with the same or differing receptor selectivities into single proteins. The internally triplicated structure of RAP, and the ability of each of the three related domains to associate independently with CR pairs, is leveraged in this application. Using one native and one engineered restriction site, the RAP coding sequence has been divided into the three, previously defined domains. Each domain comprises approximately 100 amino acids with a molecular mass of approximately 10 kD. Domain 1 (or d1) consists of amino acids 1-94 of the mature sequence of Genbank Accession No. P30533; domain 2 (or d2) consists of amino acids 95-198; and domain 3 (or d3) consists of amino acids 199-319. This configuration allows convenient swapping of domains to create novel homotrimeric and heterotrimeric domain arrays using both wild-type and mutant domain sequences. Wild-type RAP itself is bifunctional, with d1 and d3 likely bridging CR pairs that act as binding sites for, among other ligands, uPA-PAI-1 and alpha-2-macroglobulin, respectively. Mutant d3 fusions are designed to bridge different CR pairs within and between CR pair-containing proteins. In the former case, bridging will result in higher affinity complexes and greater inhibition of the binding of other ligands. In the latter case, bridging will result in cross-linking of receptors and subsequent down-regulation by endocytosis or by denial of access to the ligand binding domains for other ligands. The power of multivalency in the interactions between CR sequences and their ligands is illustrated both by RAP domains d1 and d3, which each bind two, adjacent, CR modules, and by HRV2, which binds to increasingly longer VLDLR CR3 concatamers with increasingly larger affinities. In preferred embodiments, engineered RAP d3 variants are combined so that the resulting oligomeric arrays possess unique binding specificities and biological effects. Thus, the invention contemplates that variants of RAP domains include polypeptides comprising 2 or more variants of RAP d1, comprising 2 or more variants of RAP d2, comprising 2 or more variants of RAP d3, comprising a variant of RAP d1 and variant of RAP d3 but lacking RAP d2, comprising 2 or more variants of RAP d1 together with 2 or more variants of RAP d2 or RAP d3 in various combinations (e.g. d1-d3, d1-d3-d3, d1-d1-d3, d1-d1-d3-d3, d1-d3-d1-d3, d1-d3-d1-d3-d1, d3, d1-d2-d1, d2-d2-d3, d3-d2-d3, d2-d3-d2-d3-d2-d3, etc), including consecutive repeats of the same sequence or alternating sequences, comprising multiple variants of RAP d1 and d2 in various combinations, or comprising multiple variants of RAP d2 and d3 in various combinations. The various combinations may be contiguous or separated by peptide linkers that display the domains in a 3-dimensional configuration that allows the domains to bind different CR pairs within the same CR-containing protein or to bind CR pairs of different CR-containing proteins.

In addition to RAP variants, CR-specific antibodies and combinations of RAP variants, the invention contemplates a conjugate comprising the polypeptide receptor-associated protein (RAP) variant, or combination of variants, conjugated to a diagnostic or therapeutic agent. In one embodiment, the polypeptide and diagnostic or therapeutic agent are linked through a linker. In a further embodiment, said linker is a peptide linker. In another embodiment, the conjugate comprising the polypeptide of the invention is transcytosed in vivo. In exemplary embodiments, the therapeutic agent linked to the polypeptide of the invention is selected from the group consisting of a glial cell-derived neuronal growth factor (GDNF), brain-derived neuronal growth factor (BDNF), neuronal growth factor (NGF), or other neural growth factors known in the art, a disintegrin and metalloproteinase domain 10 [*Homo sapiens*] ADAM10, or other proteases acting on APP or Abeta, MESD (a chaperone protein for LRP5/6 that is required for transport of the receptors to cell surfaces), cancer chemotherapeutic agents, protease inhibitors, pro-apoptotic molecules, autoimmune antigens or lysosomal enzymes.

In a second aspect, the invention contemplates a method of delivering the diagnostic or therapeutic agent to a particular tissue of a subject comprising administering a RAP variant or CR-specific antibody conjugated to a diagnostic or therapeutic agent to said subject in need thereof. In one embodiment, the diagnostic or therapeutic agent conjugated to a RAP variant or CR-specific antibody is delivered to a specific tissue by transcytosis across epithelial or endothelial barriers. In a related embodiment, the agent is delivered across the blood-brain barrier. In a further embodiment, the subject is a hunan suffering from a neurological disease including but not limited to Alzheimer's disease, Parkinson's disease, Multiple Sclerosis, Amylotrophic Lateral Sclerosis, other demyelination related disorders, a central nervous system cancer, traumatic brain injury, spinal cord injury, stroke or cerebral ischemia, plaque sclerosis, cerebral vasculitis, epilepsy, Huntington's disease, Tourette's syndrome, Guillain Barre syndrome, Wilson disease, Pick's disease, neuroinflammatory disorders, encephalitis, encephalomyelitis or meningitis of viral, fungal or bacterial origin, or other central nervous system infections, prion diseases, cerebellar ataxias, cerebellar degeneration, spinocerebellar degeneration syndromes, Friedreichs ataxia, ataxia telangiectasia, spinal damyotrophy, progressive supranuclear palsy, dystonia, muscle spasticity, tremor, retinitis pigmentosa, senile dementia, subcortical dementia, arteriosclerotic dementia, AIDS-associated dementia, or other dementias, striatonigral degeneration, mitochondrial encephalo-myopathies, neuronal ceroid lipofuscinosis, lysosomal storage disorders with central nervous system involvement, leukodystrophies, urea cycle defect disorders, hepatic encephalopathies, renal encephalopathies, metabolic encephalopathies, porphyria, poisonings with neurotoxic compounds, radiation-induced brain damage, or psychiatric disorders such as psychosis, anxiety, depression, attention deficits, memory disorders, cognitive disorders, appetite disorders, obesity, addiction, appetence, or drug dependence. The invention further provides a method of delivering a therapeutic protein to a lysosomal compartment in a cell within a particular tissue of a subject, comprising contacting said cell with an effective amount of a composition comprising said therapeutic enzyme conjugated to the polypeptide of the invention. In one embodiment, the subject is suffering from a lysosomal storage disease (LSD).

In a related embodiment, the invention contemplates a method of reducing CR-containing protein-associated tumorigenic or metastatic effects comprising administering a RAP, RAP variant or CR-specific antibody that selectively binds to the tumorigenic CR-containing protein. Such tumorigenic CR-containing proteins include, but are not limited to, LRP5, LRP6, the matriptases and FDC-8D6 antigen. Such CR-selective RAP or RAP variants or CR-specific antibodies diminish the tumorigenic effects associated with the target CR-containing protein by interfering with the CR functions directly, for example by blocking binding or active sites, or by targeting tissues that overexpress these CR-containing proteins with anti-tumor drugs attached to RAP of RAP variants. For example, tissues that overexpress matriptase include carcinomas, for example ovarian, cervical, prostate, breast, lung, colon or gastric carcinomas. In yet another embodiment, the invention contemplates a method of treating osteoporosis or other diseases associated with reduced osteoblast and/or increased osteoclast activity, comprising administering RAP, RAP variants or CR-specific antibodies that selectively bind LRP5 and thereby inhibit factors that antagonize osteoblast differentiation and bone deposition as well as promote osteoclast activity.

In a related aspect, the invention provides a pharmaceutical composition comprising a RAP variant conjugated to a diagnostic or therapeutic agent in a pharmaceutically acceptable carrier, diluent or excipient.

In a third aspect, the present invention features a method to produce RAP variants and conjugates in amounts which enable using compositions comprising such RAP variants or CR-specific antibodies and RAP conjugates therapeutically. The invention also provides a nucleic acid that encodes any of the foregoing polypeptides comprising RAP variants of the invention. Vectors comprising such nucleic acids, host cells containing such nucleic acids or vectors, and methods of producing such polypeptides comprising the steps of culturing the host cells in suitable culture medium and isolating the polypeptide from said host cells or culture medium are also provided.

In a fourth aspect, the invention provides a method of screening for a RAP variant or CR-specific antibody that has relatively higher binding affinity for a receptor or protein selected from the group consisting of LDLR (P01130), LRP1 (P98157), LRP1B (Q9NZR2), LRP2 (P98164), LRP3 (O75074), LRP4 (O75096), LRP5 (O75197), LRP6 (O75581), LRP8 (Q14114), Sortilin (Q92673), LRP10 (Q7Z4F1), LRP11 (Q86VZ4), LRP12 (Q9Y561), FDC-8D6 (CD320), VLDLR (P98155), TADG-15 (ST14, Q8WVC1), TMPS3 (P57727), TMPS4 (Q9NRS4), TMPS6 (Q8IU80), Q6ICC2, Q6PJ72, Q76B61, Q7RTY8, Q7Z7K9, Q86YD5, Q8NAN7, Q8NBJ0, Q8WW88, Q96NT6, Q9BYE1, Q9BYE2, Q9NPF0 and corin (Q8IZR7). In any particular complement-type repeat (CR), there is a characteristic position A and position C within the AxcBxCxD motif of the calcium-binding loop. In a CR pair, the second CR of the pair also has a characteristic position A and position C that are denoted as A' and C'. FIGS. 1-2 show the relative location of positions A and C in exemplary CR pairs. It is contemplated that any of the CR pairs described in FIGS. 1-2 may be utilized in this screening method. In one embodiment, the invention contemplates a method of screening for RAP variants or CR-specific antibody with a relatively higher affinity for a particular receptor or protein of interest in comparison with any other protein, comprising the steps of: (a) generating a candidate RAP variant or CR-specific antibody, (b) measuring binding of the candidate RAP variant or CR-specific antibody to at least two CR pairs from a CR-containing protein, wherein the CR pairs are identified by a combination of amino acids at position A, C A' and C' of the AxcBxCxD motif within each CR pair that does not exist in any other CR pair of another CR-containing protein. In one embodiment, the CR pairs contain a combination of amino acids at positions A, C, A', C' that are found in less than 10% of CR pairs derived from all the CR pairs in the proteome of an animal.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE FIGURES

FIG. 2 shows an alignment of CR sequences selected for binding analysis and RAP mutant or CR-antibody selection. The specific pairs and triplets used are indicated by brackets on the left. The panning substrate (LRP2 CR89) is indicated by the red (lighter colored) bracket. The AxcBxCxD motif within the alignment is indicated, with positions A and C for each CR sequence underlined. The text string concatenation of amino acids at A, C, A', and C' for each CR pair are indicated on the right. Amino acids in shading are identical to the predominant amino acid at the aligned position; amino acids in bold are homologous to the predominant amino acid at the aligned position. Sequences were aligned with Clustal W (44) and formatted with BOXSHADE.

FIG. 3 shows an SDS-PAGE analysis of CR proteins. Purified, refolded proteins were denatured in SDS loading buffer in the presence or absence of 2 mM DTT. Treated samples were resolved in 12% NuPAGE Bis-Tris gels as described in Methods. Gels were stained with Coomassie Brilliant Blue. Each pair of lanes is labeled at the bottom with the associated CR protein tested. Molecular weight marker sizes are indicated. Typical results are shown. Abbreviations: L1 is LRP1; L2 is LRP2; L6 is LRP6; M is MAT (matriptase, ST14); V is VLDLR; YVWR=LRP2 CR89; YVWD=LRP2 CR89R1088D; YDWR=LRP2 CR89V1047D; YDWD=LRP2 CR89V1047D R1088D; WvwR=LRP2 CR89Y1042W; WDWR=LRP2 CR89Y1042W V1047D; WVWD=LRP2 CR89Y1042W R1088D; WDWD=LRP2 CR89Y1042W V1047D R1088D.

FIG. 5A-B depict binding of RAP d3, MegaRAP1 d3 (RAPv2A d3) and intermediate sequence variants to LRP2 CR89 and LRP1 CR3-5. FIG. 5A illustrates binding of RAP d3 mutants and RAPv2A d3 revertants to LRP2 CR89.

FIG. 5B illustrates binding of RAP d3 mutants and RAPv2A d3 revertants to LRP1 CR3-5. Data were plotted and fitted by non-linear regression with the assumption of a single binding site (GraphPad Prism). $K_d$ values with standard deviations were derived from the regression analysis.

FIG. 16 shows data for binding of RAP d3 and RAP v2 (RAP v2A) variants to LRP1 CR3-5 and LRP2 CR89. NF indicates that binding could not be measured or that data could not be reliably fit using non-linear regression with the assumption of a single binding site. Percent of maximum binding is the ratio of the OD at the highest concentration tested for each ligand and the highest OD measured for all such ligands at that concentration.

FIG. 17 shows data for binding of RAP d3 and RAPv2A d3 to LRP2 CR89 variants. NF indicates that binding could not be measured or that data could not be reliably fit using non-linear regression with the assumption of a single binding site. Percent of maximum binding is the ratio of the OD at the highest concentration tested for each ligand and the highest OD measured for all such ligands at that concentration.

FIG. 18 shows RAP d3 variant sequences isolated by panning mutant phage libraries on different CR pairs. Only variable positions are shown. Amino acid numbering corresponds with mature RAP. Variant name (d3), CR pair used for affinity-selection (CR), apparent dissociation constant (Kd) for complex between variant and target CR pair (when determined), and amino acid identities at variable positions are shown.

FIG. 8 shows the complete amino acid sequences of RAP d3 variants isolated herein.

FIG. 9 shows the positive effect that truncation of the MatRAP1 variant at both the N-terminus and C-terminus has on binding affinity. Truncated variants were produced as described for full-length variants.

FIG. 10 shows the binding of 320RAP1 and the corresponding truncated variant to the target CR pair from FDC-8D6 antigen.

FIG. 11 shows the reducing (left) and non-reducing (right) Western blots of RAP-GDNF (higher band) and GDNF (lower band) demonstrating that the fusion is a disulfide-linked homodimer.

FIG. 12 shows the binding of RAP-GDNF to GFRα by solid phase assay.

FIG. 13 shows the immunoprecipitation of Ret following treatment of SK-N-SH cells with RAP-GDNF and GFRα, followed by detection with anti-phosphotyrosine antibodies.

FIG. 14 shows the immunoprecipitation of a RAP-GDNF/GFRα/phospho-Ret complex using anti-RAP-agarose beads. Immunoprecipitates were eluted in SDS-PAGE loading buffer, resolved by electrophoresis, blotted to PVDF and probed with the listed antibodies.

FIG. 15A shows that both GDNF and RAP-GDNF induce neurite outgrowth in PC12 cells.

FIG. 15B shows the dose-response of PC12 neurite outgrowth with GDNF and RAP-GDNF concentration.

Figure 1:
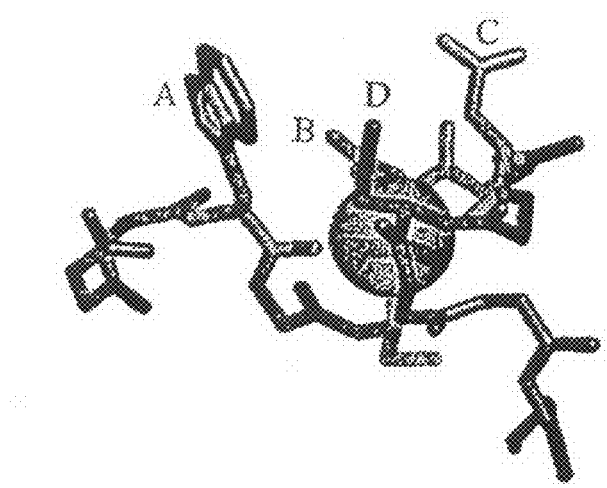
FIG. 1 is a representative illustration of a complement-type repeat, and is based on the sequence of the seventh complement-type repeat of the low-density lipoprotein receptor-related protein 1 (LRP1 CR7, PDB 1J8E), as determined by Simonovic et al. (43), showing the surface of the calcium-binding loop formed by residues at positions marked A, B, C, D. Calcium is represented as a sphere.

Supplemental Material sets out polynucleotide and polypeptide sequences for proteins and other sequences such as primers useful for the invention.

DETAILED DESCRIPTION

The invention relates to compositions comprising mutational variants of the alpha-2-macroglobulin/low density lipoprotein receptor (LDLR)-related protein-associated protein 1 (receptor-associated protein, RAP, Uniprot accession P30533, Pfam accession numbers PF06400 and PF06401) that selectively bind to members of the LDLR and transmembrane serine protease families, and other proteins. The invention further contemplates a system for isolating such variants or antibodies based on screening RAP mutant libraries against unique sequence determinants from the protein of interest. RAP variants have potential pharmaceutical applications based on two general properties of the target receptors: First, a number of the receptors have roles in the establishment and progression of disease states. Reagents that selectively bind to such receptors, therefore, may be used to alter the behavior of the receptors and the pathophysiological effects, which they support. Second, a number of the receptors have unique tissue distributions. Reagents that selectively bind to such receptors, therefore, may be used to selectively carry other drug substances to those tissues in which a targeted receptor is predominantly expressed. The invention also contemplates the use of such compositions in the prevention, management and treatment of disease, including but not limited to cellular-proliferative diseases, such as neoplastic diseases, autoimmune diseases, cardiovascular diseases, hormonal abnormality diseases, degenerative diseases, diseases of aging, diseases of the central nervous system (e.g., Alzheimer's disease, epilepsy, hyperlipidemias), psychiatric diseases and conditions (e.g., schizophrenia, mood disorders such as depression and anxiety), infectious diseases, autoimmune diseases, enzyme deficiency diseases, lysosomal storage diseases such as those described above, and the like.

A. Definitions

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

As used herein, the following terms have the meanings ascribed to them unless specified otherwise.

"Brain tumors and other neoplasia in or around the brain" as used herein includes both primary tumors and/or metastases that develop in or around the brain. It may also mean metastases of brain tumors that migrate elsewhere in the body, but remain responsive to RAP, CR-specific antibodies or RAP variant polypeptide conjugates with chemotherapeutic agents. Many types of such tumors and neoplasia are known. Primary brain tumors include glioma, meningioma, neurinoma, pituitary adenoma, medulloblastoma, craniopharyngioma, hemangioma, epidermoid, sarcoma and others. Fifty percent of all intracranial tumors are intracranial metastasis. As used herein, tumors and neoplasia may be associated with the brain and neural tissue, or they may be associated with the meninges, skull, vasculature or any other tissue of the head or neck. Such tumors are generally solid tumors, or they are diffuse tumors with accumulations localized to the head. Tumors or neoplasia for treatment according to the invention may be malignant or benign, and may have been treated previously with chemotherapy, radiation and/or other treatments.

The term "effective amount" means a dosage sufficient to produce a desired result on a health condition, pathology, and disease of a subject or for a diagnostic purpose. The desired result may comprise a subjective or objective improvement in the recipient of the dosage. "Therapeutically effective amount" refers to that amount of an agent effective to produce the intended beneficial effect on health.

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5,000 Da, up to about 2,000 Da, or up to about 1,000 Da.

A "subject" of diagnosis or treatment is a human or non-human animal, including a mammal or a primate.

"Treatment" refers to prophylactic treatment or therapeutic treatment or diagnostic treatment.

A "prophylactic" treatment is a treatment administered to a subject who does not exhibit signs of a disease or exhibits only early signs for the purpose of decreasing the risk of developing pathology. The conjugate compounds of the invention may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective. The conjugate compounds of the invention may be given as a therapeutic treatment or for diagnosis.

"Diagnostic" means identifying the presence or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in subject animal, including humans and mammals. A pharmaceutical composition comprises a pharmacologically effective amount of a RAP variant polypeptide conjugated to an active agent or a CR-specific antibody, optionally conjugated to an active agent, and also comprises a pharmaceutically acceptable carrier. A pharmaceutical composition encompasses a composition comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a conjugate compound of the present invention and a pharmaceutically acceptable carrier.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic amines.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular conjugate employed and the effect to be achieved, and the pharmacodynamics associated with each compound in the host.

"Modulate," as used herein, refers to the ability to alter, by increase or decrease (e.g., to act as an antagonist or agonist).

"Increasing relative delivery" as used herein refers to the effect whereby the accumulation at the intended delivery site (e.g., brain, lysosome) of a RAP variant-conjugated active agent or CR-specific antibody is increased relative to the accumulation of the inconjugated active agent.

"Therapeutic index" refers to the dose range (amount and/or timing) above the minimum therapeutic amount and below an unacceptably toxic amount.

"Equivalent dose" refers to a dose, which contains the same amount of active agent.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"cDNA" refers to a DNA that is complementary or identical to an mRNA, in either single stranded or double stranded form.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

A "Complement-repeat" or "CR", also known as a low-density lipoprotein receptor class A domain (LDL-A, Pfam), is a member of a family of protein domains defined by six cysteines and a cluster of acidic amino acids, among other features. A number of complement-repeats have been found to fold into a defined structure termed the LDL receptor-like module (Structural Classification of Proteins, SCOP). CR domains constitute the ligand-binding determinant of many receptors, including receptors belonging to the LDLR. A linear sequence of amino acids within each CR, with the motif AxcBxCxD, where c is a conserved cysteine, x is any amino acid, and B and D are either aspartate, glutamate or asparagine, has been demonstrated to participate in calcium binding and in the binding of ligands. Immediately adjacent pairs of particular CR domains have been demonstrated to bind to RAP. Amino acids at positions A and C in both of the two CR domains of a RAP-binding CR pair (A, C, A' and C') have been demonstrated to participate in RAP binding.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode, the same amino acid sequence. Nucleotide sequences that encode proteins and RNA may include introns.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is expressed in the recombinant host cell to produce, e.g., a "recombinant polypeptide." A recombinant polynucleotide may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Amplification" refers to any means by which a polynucleotide sequence is copied and thus expanded into a larger number of polynucleotide molecules, e.g., by reverse transcription, polymerase chain reaction, and ligase chain reaction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

A first sequence is an "antisense sequence" with respect to a second sequence if a polynucleotide whose sequence is the first sequence specifically hybridizes with a polynucleotide whose sequence is the second sequence.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays", Elsevier, New York. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variants" also refer to cDNAs derived from mRNA transcripts of genetic allelic variants, as well as the proteins encoded by them.

"RAP variant" refers to any of two or more polymorphic forms of alpha-2-macroglobulin/low density lipoprotein receptor-related protein-associated protein 1 (RAP), Uniprot accession P30533, Pfam accession numbers PF06400 and PF06401). Variants differ in the composition of their amino acid sequences based on one or more mutations involving substitution of one or more amino acids for other amino acids. Substitutions can be conservative or non-conservative based on the physico-chemical or functional relatedness of the amino acid that is being replaced and the amino acid replacing it.

"Selectivity," "binding selectivity" or "binds selectively", refers to differences in the affinity of a ligand for different receptors. A ligand is selective for a particular receptor if it binds that receptor with an affinity that is at least 3-fold greater than other receptors. For example, RAP binds to LRP1, LRP1B, LRP2, Sortilin, apoER2 and VLDLR with almost identical affinities. Therefore, RAP is not selective for one of these receptors over another. However, while RAP binds strongly to LRP1, LRP1B, LRP2, Sortilin, apoER2 and VLDLR, with dissociation constants of less than 5 nM, it binds only weakly to LDLR, LRP5 and LRP6, with affinities that are at least 10-fold lower than for LRP1. Therefore, RAP is selective for LRP1, LRP1B, LRP2, Sortilin, apoER2 and VLDLR relative to LDLR, LRP5 and LRP6. HRV2 coat protein binds strongly to VLDLR but does not bind to other LDLR. Therefore, HRV2 coat protein shows selectivity in its binding, with a preference for VLDLR over other LDLR. Reelin binds to apoER2 and VLDLR but not to other LDLR. Therefore, reelin is selective for apoER2 and VLDLR over other LDLR.

The terms "identical" or "percent identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially homologous" or "substantially identical" in the context of two nucleic acids or polypeptides, generally refers to two or more sequences or subsequences that have at least 40%, 60%, 80%, 90%, 95%, 98% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of either or both comparison biopolymers.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm calculates the percent sequence identity for the test sequence(s) relative to the reference sequence, based on the designated program parameters.

Optimal alignment of sequences for comparison can be conducted, e.g., by the local homology algorithm of Smith and Waterman, Adv. Appl. Math. 2:482 (1981), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle, J. Mol. Evol. 35:351-360 (1987). The method used is similar to the method described by Higgins and Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. Another algorithm that is useful for generating multiple alignments of sequences is Clustal W (Thompson et al. Nucleic Acids Research 22: 4673-4680, 1994).

Another example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, Proc. Natl. Acad. Sci. USA 89:10915, 1989).

In addition to calculating percent sequence identity, the BLAST algorithm also performs a statistical analysis of the similarity between two sequences (see, e.g., Karlin and Altschul, Proc. Nat'l. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described herein.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In some embodiments, the conjugates of the invention are substantially pure or isolated. In some embodiments, the conjugates of the invention or a CR-specific antibody of the invention are substantially pure or isolated with respect to the macromolecular starting materials used in their synthesis. In some embodiments, the pharmaceutical composition of the invention comprises a substantially purified or isolated conjugate of a RAP variant polypeptide and the active agent or a substantially purified or isolated CR-specific antibody admixed with one or more pharmaceutically acceptable excipient.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

"Detecting" refers to determining the presence, absence, or amount of an analyte in a sample, and can include quantifying the amount of the analyte in a sample or per cell in a sample.

"Detectable moiety" or a "label" refers to a composition detectable by spectroscopic, photochemical, biochemical, immunochemical, or chemical means. For example, useful labels include $^{32}$P, $^{35}$S, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., P D. Fahrlander and A. Klausner, Bio/Technology (1988) 6:1165.) Quantitation of the signal is achieved by, e.g., scintillation counting, densitometry, or flow cytometry.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

B. LDLR

"LDLR" refers to members of the low-density lipoprotein receptor family including the low-density lipoprotein receptor-related protein 1 (LRP1). LRP1 is a large protein of 4525 amino acids (600 kDa), which is cleaved by furin to produce two subunits of 515-(alpha) kD and 85-(B) kDa that remain non-covalently bound. LRP is expressed on most tissue types, but is primarily found in the liver. Other members of the low-density lipoprotein (LDL) receptor family include LDL-R (132 kDa); LRP2 (megalin, gp330); LRP/LRP1 and LRP1B (600 kDa); VLDL-R (130 kDa); LRP5; LRP6; apoER-2 (LRP-8, 130 kDa); Mosaic LDL-R (LR11, 250 KDa); and other members such as LRP3, LRP6, and LRP-7. Characteristic features of the family include cell-surface expression; extracellular ligand binding domain repeats (Dx-SDE); a requirement of Ca++ for ligand binding; binding of RAP and apoE; EGF precursor homology domain repeats (YWTD); a single membrane spanning region; internalization signals in the cytoplasmic domain (FDNPXY); and receptor mediated endocytosis of various ligands. Some members of the family, including LRP1, LRP5, LRP6, apoER2 and VLDLR, participate in signal transduction pathways.

LDLR ligands refer to a number of molecules that are known to bind LDLR. These molecules include, for instance, lactoferrin, RAP, lipoprotein lipase, apoE, Factor VIII, beta-amyloid precursor, alpha-2-macroglobulin, thrombospondin 2 MMP-2 (matrix metalloproteinase-2), MPP-9-TIMP-1 (tissue inhibitor of matrix metalloproteinase-1); uPA (urokinase plasminogen activator):PAI-I (plasminogen activator inhibitor-1):uPAR (uPA receptor); and tPA (tissue plasminogen activator):PAI-1:uPAR.

LRP1 is believed to be a multifunctional receptor. A binding repeat, resembling those found in the LDL receptor, is the molecular principle for the ability to bind a variety of ligands that were previously thought to be unrelated. These include the ligands described in the previous paragraph in addition to: *Pseudomonas* exotoxin A, human rhinovirus, lactoferrin and the receptor associated protein (RAP). See, Meilinger et al., FEBS Lett, 360:70-74 (1995). LRP1 is has the GenBank Accession No.: X 13916 and SwissProt Primary Accession No.: Q07954. Alternative names for the LRP1 gene/protein include: Low-density lipoprotein receptor-related protein 1 [precursor], LRP, Alpha-2-macroglobulin receptor, A2MR, Apolipoprotein E receptor, ApoER, CD91, LRP1 or A2MR.

LDLR bind to a wide variety of extracellular ligands through conserved protein domains within the N-terminal extracellular domain, or ectodomain, of each receptor. These domains include the complement-type repeat (CR, or low-density lipoprotein receptor domain class A, ldl-a), the EGF-like repeat and the YWTD, or beta-propeller, domain. The representation and arrangement of each domain varies with each particular LDLR. The CR domains are responsible for association with most of the ligands that have been identified. The CR sequence specifies a conserved fold, termed the LDL receptor-like module (SCOP terminology). Each approximately 36 amino acid CR contains six cysteines that form three intramolecular cystines in a 1-3, 2-5, 4-6 configuration, and a calcium ion bound within one lobe of a bilobate loop FIG. 1). As demonstrated by structural studies on the LDLR (with seven CR domains), LRP1 (CR3, 7 and 8), VLDLR (CR3, bound to human rhinovirus 2) and the quail TVA receptor (single CR), the CR fold represents a well-defined, compact structure. Apart from the cystines, other amino acids within the CR serving important structural roles include four acidic residues that participate in calcium chelation and a pair of conserved hydrophobic residues (usually F and I) that pack under and behind one lobe of the calcium-binding loop. The consensus calcium-binding loop sequence is AxcBxCxD (FIG. 1), with the side chains contributed by positions A, B, C and D forming one surface of the loop, and c representing one of the cystine-forming cysteines (number 4). As demonstrated in crystal structures, aspartate (carboxylate), asparagine (carboxamide) or glutamate (carboxylate) at positions B and D directly participate in calcium chelation through their side chains (the other two acidic side chains that participate directly in calcium chelation are contributed by positions approximately 6 residues C-terminal to position D). Main chain carbonyls for positions A and C also participate in calcium chelation, while the side chains for these residues project away from the loop surface into the solvent (FIG. 1). Importantly, the previously mentioned structural data show that the CR fold structure is tolerant of amino acid substitution at a number of positions, including A and C (FIGS. 1 and 2).

Members of the LDLR family are well expressed on capillary endothelium and on CNS cell types including neurons and astrocytes (e.g., LDL receptor, Megalin, LRP1). The LDL receptor family endocytose bound ligand and have been demonstrated to transcytose ligands across polarized epithelial cells in the kidney, thyroid and across capillary endothelial cells in the brain. LDLR therefore comprises a pool of compositionally and functionally related receptors expressed at different levels in different tissues. In some embodiments, this invention uses RAP variants or CR-specific antibodies which preferentially bind and thereby target members of this and other protein families (and particularly cells, tissues, and organs expressing a member of these families). Examples include the VLDLR on muscle tissue, LRP1B on neuronal tissue, Megalin on both kidney and neuronal tissue and LRP1 on vascular smooth muscle tissue.

C. Receptor-Associated Protein (RAP)

An endoplasmic reticular chaperone protein, the receptor-associated protein (RAP), binds to CR sequences within most LDLR. RAP assists in the folding of LDLR within the secretory pathway and antagonizes binding of all other known ligands to LDLR (Bu, (2001) Int Rev Cytol 209, 79-116). Despite the lack of detailed structural information on RAP, the association of RAP with the CR fold has been extensively characterized by a combination of receptor binding assays, calorimetry, and mutagenesis (Andersen, et al., (2001) Biochemistry 40, 15408-15417; Andersen, et al., (2000) J Biol Chem 275, 21017-21024; Migliorini, et al., (2003) J Biol Chem 278, 17986-17992; Neels, et al., (1999) J Biol Chem 274, 31305-31311; Horn, et al., (1997) J Biol Chem 272, 13608-13613)). The polynucleotide and polypeptide sequences of RAP are set out in the Supplemental Material section submitted with the Figures.

RAP is comprised of an array of three weakly homologous domains (Obermoeller, et al., (1997) J Biol Chem 272, 10761-10768). Each of these domains (d1, d2 and d3) has been shown to bind with varying affinity to pairs of immediately adjacent CR sequences within the LDLR ectodomains. Each of the effects of full-length RAP on LDLR, including facilitation of folding and inhibition of the binding of most other ligands (except α-2-macroglobulin), are recapitulated by RAPd3 alone. RAP d3 comprises amino acids 200-323 of mature Uniprot P30533 and amino acids 234-357 of precursor Uniprot P30533. RAPd3, which also has the highest affinity for CR pairs, and RAPd1, with lower affinity, both show a strong preference for those CR sequences in which aromatic and acidic residues occupy positions A and C, respectively, in the calcium-binding loop. More specifically, both RAP domains prefer tryptophan and aspartate at these sites. This shared preference exists despite significant differences in the binding thermodynamics of d1 and d3, suggesting, in turn, significant differences in the formation of complexes between CR pairs and each domain (Andersen, et al., (2001) Biochemistry 40, 15408-15417). Substitution of serine for tryptophan in position A of the second CR sequence of a particular CR pair (LRP1 CR5 and CR6, or LRP1 CR56) reduces the affinity for RAPd3 by at least three orders of magnitude; RAPd1 binding to the same CR is undetectable after this substitution. In contrast, substitution of one unconserved position that does not contribute to the surface of the calcium-binding loop has been shown to have no effect on binding of RAP or RAP subdomains.

The second ligand-binding domain of human LRP1 is composed, of eight consecutive CR units. Each of the seven possible adjacent CR pairs have been individually expressed and assayed for binding to RAPd3 (Andersen, et al., (2000) J Biol Chem 275, 21017-21024). Except for the last pair (CR9 and CR10), which contains non-preferred residues at A and C in the second CR, all pairs bind with similar affinity (1-5 nM) to RAP. A comparison of the sequences of these pairs can be used to identify those positions to which RAP is indifferent. The power of the comparison can be increased by including CR pairs from the VLDLR that have also been shown to bind to RAP with high affinity (Mikhailenko, et al., (1999) J Cell Sci 112 (Pt 19), 3269-3281). Subtracting from consideration all previously described conserved structural residues, as well as positions A and C, only one additional position shows strong, though not strict, conservation. This site separates positions B and C in the calcium-binding loop and represents the point of maximum loop curvature. A preference for glycine here is not unexpected based on the high representation of this amino acid at peptide bends, a result of the unique main-chain flexibility of this residue. This analysis suggests that, apart from conserved positions required for the structural integrity of the CR fold, unconserved positions A and C play the largest role in complex formation with RAP.

Crystal structures of the LDLR CR array complexed to its own beta-propeller at low pH, as well as of the VLDLR CR3 complexed to the capsid of human rhinovirus 2 (HRV2), provide some information on the nature of the association between key positions in the CR pair, and complementary positions within RAP (11, 47). It appears as though the tryptophan at position A and the acidic amino acid at position C act in concert to bind a single lysine within the ligand sequence (beta-propeller or HRV2 capsid protein). The tryptophan packs hydrophobically against the aliphatic portion of the lysine side-chain, while the carboxylate forms a saltbridge with the protonated amine of the same. The existence of two A/C pairs within each CR pair and two critical lysines within each RAP d3 indicates that two such interactions might define the CR-RAP complex. Additional stabilization of the complex may come from association of the two basic "patches" within d3 and the negatively charged calciumbinding sites of each CR. This model has recently been confirmed (48). Substitution of other types of interactions for the primary interaction may permit secondary interactions to remain the same, or only slightly altered. Such a substitution would allow for production of RAP mutants that bind to CR pairs in which A and C have amino acids other than tryptophan and aspartate/glutamate, respectively. Since a number of such unique CR pairs are found in all LDLR and other CR-containing proteins, RAP mutants with unusual A/C preferences are likely to bind to particular receptors selectively.

A comparison of all CR pairs within the Pfam database (maintained by Washington University, St. Louis, Mo.) reveals that there is a wide diversity of substitutions at both key positions A and C and that CR pairs with unique combinations of amino acids at these positions (A, C, A', C') can be found in all human LDLR, including LDLR (P01130), LRP1 (P98157), LRP1B (Q9NZR2), LRP2 (P98164), LRP3 (O75074), LRP4 (O75096), LRP5 (O75197), LRP6 (O75581), LRP8 (O14114), Sortilin (Q92673), LRP10 (Q7Z4F1), LRP11 (Q86VZ4), LRP12 (Q9Y561), and VLDLR (P98155). Other CR-containing proteins include the family of transmembrane serine proteases, such as: TADG-15 (ST14/Matriptase/MT-SP1), Q6ICC2 (Uniprot accession number), Q6PJ72, Q76B61, Q7RTY8, Q7Z7K9, Q86YD5, Q8NAN7, Q8NBJ0, Q8WW88, Q96NT6, Q9BYE1, Q9BYE2, Q9NPF0 and corin. The protein designations reflect the receptors Uniprot database designation.

Previous studies have suggested that wild-type RAP will not have physiologically relevant affinity for these non-canonical CR pairs.

D. Antibodies

The invention contemplates antibodies specific for the CR containing proteins described herein. Antibodies of the invention that are "specific" for, "specifically bind" or are "selective" for an antigen preferably bind one CR-containing protein (or a subset of CR-containing proteins) with substantially greater affinity than another member of the CR-containing protein family, e.g. at least 1.5-fold, 2-fold, 2.5-fold, 3-fold, 4-fold, 5-fold, 7-fold, 10-fold, 20-fold or higher affinity, and preferably bind to one CR-containing protein (or a subset) with substantially greater affinity than all other members of the family. Antibodies of the invention may be characterized by an affinity (Kd) for the target CR-containing protein of at least $10^{-4}$ M, $10^{-5}$ M, $10^{-6}$ M, $10^{-7}$ M, $10^{-8}$ M, $10^{-9}$ M, $10^{-10}$ M, or $10^{-11}$ M or higher affinity. Such affinities may be readily determined using conventional techniques, such as by using a BIAcore instrument or by radioimmunoassay using radiolabeled target antigen. Affinity data may be analyzed, for example, by the method of Scatchard et al., Ann N.Y. Acad. Sci., 51:660 (1949).

The term "antibody" is used in the broadest sense and includes fully assembled antibodies, monoclonal antibodies, polyclonal antibodies, multispecific antibodies (e.g., bispecific antibodies), antibody fragments that can bind antigen (e.g., Fab', F'(ab)2, Fv, single chain antibodies, diabodies), and recombinant peptides comprising the forgoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, are contemplated. Different isotypes have different effector functions; for example, IgG1 and IgG3 isotypes have antibody-dependent cellular cytotoxicity (ADCC) activity. An "immunoglobulin" or "native antibody" is a tetrameric glycoprotein composed of two identical pairs of polypeptide chains (two "light" and two "heavy" chains). The amino-terminal portion of each chain includes a "variable" ("V") region of about 100 to 110 or more amino acids primarily responsible for antigen recognition. Within this variable region, the "hypervariable" region or "complementarity determining region" (CDR) consists of residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)] and/or those residues from a hypervariable loop (i.e., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., J. Mol. Biol. 196: 901-917 (1987)]. The carboxy-terminal portion of each chain defines a constant region primarily responsible for effector function.

The term "monoclonal antibody" as used herein refers to an antibody obtained from a population of substantially homogeneous antibodies, i.e., the individual antibodies comprising the population are identical except for possible naturally occurring mutations or alternative post-translational modifications that may be present in minor amounts, whether produced from hybridomas or recombinant DNA techniques. Nonlimiting examples of monoclonal antibodies include murine, chimeric, humanized, or human antibodies, or variants or derivatives thereof. Humanizing or modifying antibody sequence to be more human-like is described in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991); Co, M. S., et al. (1994), J. Immunol. 152, 2968-2976); Studnicka et al. Protein Engineering 7: 805-814 (1994); each of which is incorporated herein by reference. One method for isolating human monoclonal antibodies is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. Another method for isolating human monoclonal antibodies uses transgenic animals that have no endogenous immunoglobulin production and are engineered to contain human immunoglobulin loci. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); WO 91/10741, WO 96/34096, WO 98/24893, or U.S. patent application publication nos. 20030194404, 20030031667 or 20020199213; each incorporated herein by reference.

Antibody fragments may be produced by recombinant DNA techniques or by enzymatic or chemical cleavage of intact antibodies. "Antibody fragments" comprise a portion of an intact full length antibody, preferably the antigen binding or variable region of the intact antibody, and include multispecific (bispecific, trispecific, etc.) antibodies formed from antibody fragments. Nonlimiting examples of antibody fragments include Fab, Fab', F(ab')2, Fv [variable region], domain antibody (dAb) [Ward et al., Nature 341:544-546, 1989], complementarity determining region (CDR) fragments, single-chain antibodies (scFv) [Bird et al., Science 242:423-426, 1988, and Huston et al., Proc. Natl. Acad. Sci. USA 85:5879-5883, 1988, optionally including a polypeptide linker; and optionally multispecific, Gruber et al., J. Immunol. 152: 5368 (1994)], single chain antibody fragments, diabodies [EP 404,097; WO. 93/11161; and Hollinger et al., Proc. Natl. Acad. Sci. USA, 90:6444-6448 (1993)], triabodies, tetrabodies, minibodies [Olafsen, et al., Protein Eng Des Sel. 2004 April; 17(4):315-23], linear antibodies [Zapata et al., Protein Eng., 8(10):1057-1062 (1995)]; chelating recombinant antibodies [Neri et al., J Mol. Biol. 246:367-73, 1995], tribodies or bibodies [Schoonjans et al., J Immunol. 165:7050-57, 2000; Willems et al., J Chromatogr B Analyt Technol Biomed Life Sci. 786:161-76, 2003], intrabodies [Biocca, et al., EMBO J. 9:101-108, 1990; Colby et al., Proc Natl Acad Sci USA. 101:17616-21, 2004], nanobodies [Cortez-Retamozo et al., Cancer Research 64:2853-57, 2004], small modular immunopharmaceuticals (SMIPs) [WO03/041600, U.S. Patent publication 20030133939 and US Patent Publication 20030118592], an antigen-binding-domain immunoglobulin fusion protein, a camelized antibody [Desmyter et al., J. Biol. Chem. 276:26285-90, 2001; Ewert et al., Biochemistry 41:3628-36, 2002; U.S. Patent Publication Nos. 20050136049 and 20050037421], a VHH containing antibody, or variants or derivatives thereof, and polypeptides that contain at least a portion of an immunoglobulin that is sufficient to confer specific antigen binding to the polypeptide, such as a CDR sequence, as long as the antibody retains the desired biological activity.

The term "variant" when used in connection with antibodies refers to polypeptide sequence of an antibody that contains at least one amino acid substitution, deletion, or insertion in the variable region or the portion equivalent to the variable region, provided that the variant retains the desired binding affinity or biological activity. In addition, the antibodies of the invention may have amino acid modifications in the constant region to modify effector function of the antibody, including half-life or clearance, ADCC and/or CDC activity. Such modifications can enhance pharmacokinetics or enhance the effectiveness' of the antibody in treating cancer, for example. See Shields et al., J. Biol. Chem., 276(9): 6591-6604 (2001), incorporated by reference herein in its entirety. In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

The term "derivative" when used in connection with antibodies refers to antibodies covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. Derivatives of the invention will retain the binding properties of underivatized molecules of the invention. Conjugation of cancer-targeting antibodies to cytotoxic agent, for example, radioactive isotopes (e.g., I131, I125, Y90 and Re186), chemotherapeutic agents, or toxins, may enhance destruction of cancerous cells

E. RAP Variants

The invention contemplates RAP variants having differential binding affinity for LDL family receptors, transmembrane serine protease receptors and other proteins. Random and site-directed mutagenesis of RAP indicates that there may be a few residues that contribute disproportionately to the affinity of the ligand complex with the CR pair (Migliorini, et al., (2003) J Biol Chem 278, 17986-17992). In particular, lysines at positions 256 and 270 in RAPd3 have been found to be important for binding of this domain to LRP1. Also important are two, discrete, ten amino acid basic regions centered on positions 205 and 285, respectively (Melman, et al., (2001) J Biol Chem 276, 29338-29346). These observations are consistent with there being a limited set of residues, a "hot-spot", that contribute the majority of binding energy between RAP and CR pairs, a phenomenon observed in other protein-protein interfaces (Li, et al, (2005) Structure (Camb) 13, 297-307; Halperin, et al., (2004) Structure (Camb) 12, 1027-1038; Gao, et al., (2004) J Mol Model (Online) 10, 44-54; Dwyer, et al., (2001) Biochemistry 40, 13491-13500; DeLano, (2002) Curr Opin Struct Biol 12, 14-20; Bogan, et al., (1998) J Mol Biol 280, 1-9; Clackson, et al., (1995) Science 267, 383-386).

i. LRP2-Selective RAP Variants

LRP2 has been shown to be expressed on brain capillary endothelium and to mediate transport of apoJ into the parenchyma of the brain (Lundgren, et al., (1997) J Histochem Cytochem 45, 383-392; Zlokovic, et al., (1996) Proc Natl Acad Sci USA 93, 4229-4234; Shayo, et al., (1997) Life Sci 60, PL115-118). RAP variants and anti-CR antibodies that selectively bind to LRP2 with greater affinity than other LDLR are expected to have enhanced distribution to the brain. For these reasons, RAP variants or CR-specific antibodies that selectively bind to LRP2 and fusions containing drugs conjugated to such RAP variants or CR-specific antibodies are expected to have enhanced distribution to the brain. For example, GDNF has been demonstrated to promote survival and growth of nigrostriatal neurons in subjects with Parkinson's disease (Lin, et al., (1993) Science 260, 1130-1132). GDNF does not cross into the brain from the vasculature. Fusions of LRP2-selective RAP variants to GDNF would be expected to increase the distribution of GDNF to the brain.

ii. VLDLR-Selective RAP Variants

Similarly, VLDLR has been shown to be expressed on brain capillary endothelium and to mediate transport of lipoprotein lipase across the endothelium of the aorta (Wyne, et al., (1996) Arterioscler Thromb Vasc Biol 16, 407-415; Obunike, et al., (2001) J Biol Chem 276, 8934-8941). RAP variants or CR-specific antibodies that selectively bind to VLDLR and fusions containing drugs conjugated to such RAP variants or CR-specific antibodies are expected to have enhanced distribution to the brain. VLDLR has also been implicated in foam cell formation by mediating uptake of excess free fatty acids (FFA) into vascular macrophages (Hiltunen, et al., (1998) Circulation 97, 1079-1086; Qu, et al., (2004) J Huazhong Univ Sci Technolog Med Sci 24, 1-4, 8). RAP variants and CR-specific antibodies that selectively bind to VLDLR would be expected to block association of lipoprotein particles with macrophages and inhibit foam cell formation. Such variants and antibodies would also be expected to limit transfer of FFA from circulating lipoprotein into adipocytes, slowing the progression toward obesity in susceptible subjects (Goudriaan, et al., (2001) Arterioscler Thromb Vasc Biol 21, 1488-1493; Goudriaan, et al. (2004) J Lipid Res 45, 1475-1481; Tacken, et al., (2001) Curr Opin Lipidol 12, 275-279; Yagyu, et al., (2002) J Biol Chem 277, 10037-10043). The high level of expression of VLDLR on the luminal surface of muscle endothelium, along with the low level of expression of VLDLR in liver, would be expected to drive distribution of VLDLR-selective RAP variants and CR-specific antibodies to muscle tissue after intravenous administration. Molecules with therapeutic effects on muscle tissue could be attached to VLDLR-selective RAP variants or CR-specific antibodies to improve distribution of such molecules to muscle.

iii. RAP Variants Selective for Other Receptors

Overexpression of at least three CR-containing proteins, LRP5, LRP6 and ST14 (TADG-15), has been independently associated with increased tumorigenicity or carcinogenesis (Li, et al., (2004) Oncogene 23, 9129-9135; Hoang, et al., (2004) Int J Cancer 109, 106-111; Tanimoto, et al., (2005) Br J Cancer 92, 278-283; Santin, et al., (2004) Int J Cancer 112, 14-25; Santin, et al., (2003) Cancer 98, 1898-1904; Tanimoto, et al., (2001) Tumour Biol 22, 104-114). RAP variants or anti-CR-specific antibodies, that bind to these proteins would be expected to provide a means of diminishing their tumorigenic effects, either by interfering with their functions directly or by targeting tissues that overexpress these proteins with drugs attached to the RAP variant or anti-CR-specific antibodies. For example, the protease domain adjacent to the CR array in the ectodomain of matriptase (ST14) has been implicated in the enhanced invasiveness and tumorigenicity of cells that overexpress matriptase (ST14). A matriptase-selective RAP variant alone, anti-CR-specific antibody, or fusions between a matriptase-selective RAP variant and a protease inhibitor would be expected to specifically block those effects of matriptase related to its proteolytic activity. LRP6-selective RAP variants, anti-CR-specific antibodies, or variant fusions could be designed to down-regulate LRP6 on tumor cells, either by inducing endocytosis of LRP6 or by interfering with the Wnt signal transduction events mediated by LRP6. Similarly, LRP6-selective RAP variants or anti-CR-specific antibodies conjugated to drugs (e.g. cancer chemotherapeutic drugs) or diagnostic agents can be used to target tissues that overexpress LRP6.

Enhanced Wnt signaling through LRP5 has been demonstrated to increase osteoblast differentiation, inhibit osteoclast activity and enhance bone deposition (Westendorf, et al., (2004) Gene 341, 19-39; Zhang, et al., (2004) Mol Cell Biol 24, 4677-4684). This mechanism has been validated with osteoblast-specific APC (adenomatous polyposis coli) knockout mice and with LRP5 mutants that are insensitive to DKK (Dickkopf)-1 and sclerostin-mediated inhibition (Zhang, et al., (2004) Mol Cell Biol 24, 4677-4684; Holmen, et al., (2005) J Biol Chem). LRP5-specific RAP variants or anti-CR-specific antibodies that interfere with inhibitor binding, or which enhance Wnt signaling through other means (e.g. stabilizing LRP5 without blocking Wnt binding), would be expected to have similar effects. For example, fusions between RAP variants or anti-CR-specific antibodies specific for either of the two LRP5 CR pairs and the beta-propeller chaperone protein Mesd would be expected to interfere with DKK-1-mediated antagonism of Wnt signaling through LRP5 (Hsieh, et al., (2003) Cell 112, 355-367; Herz, et al., (2003) Cell 112, 289-292). These variants or antibodies are further expected to have therapeutic effects in the treatment of osteoporosis or other diseases associated with reduced osteoblast activity and/or increased osteoclast activity.

In more general embodiments, receptor-selective RAP variants or anti-CR-specific antibodies, alone or in combination, constitute a means by which receptors might be specifically controlled. There are least four mechanisms by which control could be effected: Competitive blockade of ligand binding by direct association of RAP variants or anti-CR-specific antibodies with ligand binding sites, non-competitive blockade of ligand binding by RAP variant-induced allosteric modification of ligand binding sites, clearance of receptors from the cell surface following variant or variant fusion-induced cross-linking between the same or different receptors, modification of the targeted receptor or the cell on which the receptor is expressed, or the tissue in which the cell resides, by agents that are attached to receptor-selective RAP variants (e.g. proteases, protease inhibitors, glycosidases, radioisotopes, pro-apoptotic agents, toxins, therapeutic molecules (drugs), other receptor binding moieties, etc).

It is contemplated that RAP variants or anti-CR-specific antibodies may be fused or linked to therapeutic proteins such as glial cell-derived neuronal growth factor (GDNF), brain-derived neuronal growth factor (BDNF), neuronal growth factor (NGF), other neurotrophic factors known to the art, ADAM10, other protease acting on APP or Abeta, MESD, cancer chemotherapeutic agents, protease inhibitors, autoimmune antigens, pro-apoptotic molecules, lysosomal enzymes, DNA or siRNA. It is contemplated that fusion of these agents to RAP variants or anti-CR-specific antibodies with improved affinity for LDLR receptors will facilitate increased transport across the blood-brain barrier and other tissue sites. In one aspect, it is contemplated that fusion to RAP variants or anti-CR-specific antibodies results in altered tissue distribution of the RAP-therapeutic agent fusion after intravenous, subcutaneous, intramuscular, intraventricular, intrathecal or intraparenchymal administration of the fusion agent.

It is further provided that fusion to RAP or RAP domain variants or anti-CR-specific antibodies results in alterations in the pharmacological activity of the fusion partner caused by one or more of the following effects: Increased potency, diminished binding to receptors or tissues that are different from the intended target receptor or tissue, increased binding to receptors or tissues that are the intended target receptor or tissue, increased access to receptors or tissues that are the intended target receptor or tissue, altered rates of clearance from the body, and, altered characteristics of the immune response to the protein.

It is further provided that RAP variants or anti-CR-specific antibodies may be conjugated to therapeutic nucleic acids, such as DNA or siRNA, in order to improve the tissue-selective distribution of said nucleic acids and facilitate endocytosis of said nucleic acids into cells (Kim et al., (2004) Bioconjugate Chemistry 15, 326-332).

F. Conjugates of RAP Variant and Active Agent

A "RAP conjugate", "ligand-polypeptide conjugate" "chimeric molecule comprising a RAP variant conjugated to an active agent" each refers to a compound comprising a RAP variant attached to an active agent. As used herein, the term "conjugated" means that the therapeutic agent(s) and RAP variant polypeptide or anti-CR-specific antibody are physically linked by, for example, by covalent chemical bonds, physical forces such van der Waals or hydrophobic interactions, encapsulation, embedding, or combinations thereof. In preferred embodiments, the therapeutic agent(s) and the RAP variant polypeptide or anti-CR-specific antibody are physically linked by covalent chemical bonds. As such, preferred chemotherapeutic agents contain a functional group such as an alcohol, acid, carbonyl, thiol or amine group to be used in the conjugation to RAP variant or fragment thereof. Adriamycin is in the amine class and there is also the possibility to link through the carbonyl as well. Paclitaxel is in the alcohol class. Chemotherapeutic agents without suitable conjugation groups may be further modified to add such a group. All these compounds are contemplated in this invention. In the case of multiple therapeutic agents, a combination of various conjugations can be used.

In some embodiments, a covalent chemical bond that may be either direct (no intervening atoms) or indirect (through a linker e.g., a chain of covalently linked atoms) joins the RAP variant or anti-CR-specific antibody and the active agent. In preferred embodiments, the RAP variant or anti-CR-specific antibody and the active agent moiety of the conjugate are directly linked by covalent bonds between an atom of the RAP variant or anti-CR-specific-antibody and an atom of the active agent. In some preferred embodiments, the megalin binding moiety is connected to the active agent moiety of the compound according to the invention by a linker that comprises a covalent bond or a peptide of virtually any amino acid sequence or any molecule or atoms capable of connecting the RAP variant or anti-CR-specific antibody to the active agent.

In some embodiments, the linker comprises a chain of atoms from 1 to about 60, or 1 to 30 atoms or longer, 2 to 5 atoms, 2 to 10 atoms, 5 to 10 atoms, or 10 to 20 atoms long In some embodiments, the chain atoms are all carbon atoms. In some embodiments, the chain atoms are selected from the group consisting of C, O, N, and S. Chain atoms and linkers may be selected according to their expected solubility (hydrophilicity) so as to provide a more soluble conjugate. In some embodiments, the linker provides a functional group that is subject to enzymatic attack in a lysosome. In some embodiments, the linker provides a functional group which is subject to attack by an enzyme found in the target tissue or organ and which upon attack or hydrolysis severs the link between the active agent and the RAP variant or anti-CR-specific antibody. In some embodiments, the linker provides a functional group that is subject to hydrolysis under the conditions found at the target site (e.g., low pH of a lysosome). A linker may contain one or more such functional groups. In some embodiments, the length of the linker is long enough to reduce the potential for steric hindrance (when an active agent is large) between one or both of the RAP variant binding site and the active agent active binding site.

If the linker is a covalent bond or a peptide and the active agent is a polypeptide, the entire conjugate can be a fusion protein. Such peptidyl linkers may be any length. Exemplary linkers are from about 1 to 50 amino acids in length, 5 to 50, or 10 to 30 amino acids in length. Such fusion proteins may be produced by recombinant genetic engineering methods known to one of ordinary skill in the art. In some embodiments, the RAP variant portion of the conjugate is formulated to rapidly degrade to release the active compound. In other embodiments, the linker is subject to cleavage under intracellular, or more preferably, lysosomal environmental conditions to release or separate the active agent portion from the RAP variant or CR-specific antibody polypeptide portion.

The conjugate can comprise one or more active agents linked to the same RAP variant or CR-specific antibody. For example, conjugation reactions may conjugate from 1 to 5, about 5, about 1 to 10, about 5 to 10, about 10 to 20, about 20 to 30, or 30 or more molecules of an active agent to the RAP variant polypeptide. These formulations can be employed as mixtures, or they may be purified into specific stoichiometric formulations. Those skilled in the art are able to determine which format and which stoichiometric ratio is preferred. Further, more than one type of active agent may be linked to the RAP variant or CR-specific antibody polypeptide where delivery of more than one type of an agent to a target site or compartment is desired. A plurality of active agent species may be attached to the same RAP variant polypeptide e.g., adriamycin-cisplatinum RAP variant polypeptide (or other RAP variant) conjugates. Thus, the conjugates may consist of a range of stoichiometric ratios and incorporate more than one type of active agent. These, too, may be separated into purified mixtures or they may be employed in aggregate.

The RAP variant or fragments thereof or CR-specific antibody, conjugate according to the invention may be modified as desired to enhance its stability or pharmacokinetic properties (e.g., PEGylation). Suitable linkers and their functional groups for conjugating RAP variant polypeptides and an active agent, and the synthetic chemical methods readily adaptable for preparing such, are described in U.S. Patent Application No. 60/395,762 which is assigned to the same assignee as the present application and herein incorporated by reference in its entirety.

The synthesis of these conjugates is efficient and convenient, producing high yields and drugs with enhanced aqueous solubility.

G. Active Agents

Active agents according to the invention include agents that can affect a biological process. Particularly preferred active agents for use in the compounds compositions and methods of the invention are therapeutic agents, including drugs and diagnostic agents. The term "drug" or "therapeutic agent" refers to an active agent that has a pharmacological activity or benefits health when administered in a therapeutically effective amount. Particularly preferred agents are naturally occurring biological agents (e.g., enzymes, proteins, polynucleotides, antibodies, polypeptides, nanoparticles, glycoconjugates). In some embodiments, the active agent conjugated to a RAP variant or CR-specific antibody is a molecule, as well as any binding portion or fragment thereof, that is capable of modulating a biological process in a living host. Examples of drugs or therapeutic agents include substances that are used in the prevention, diagnosis, alleviation, treatment or cure of a disease or condition. It is particularly contemplated that the agent is not an agent that causes a disease. Specifically, the agent is not amyloid β protein.

i. Protein Active Agents

The active agent can be a non-protein or a protein. The active agent can be a protein or enzyme or any fragment of such that still retains some, substantially all, or all of the therapeutic or biological activity of the protein or enzyme. In some embodiments, the protein or enzyme is one that, if not expressed or produced or if substantially reduced in expression or production, would give rise to a disease, including but not limited to, lysosomal storage diseases. Preferably, the protein or enzyme is derived or obtained from a human or mouse.

In preferred embodiments of the invention, when the active agent conjugated to RAP or RAP variant polypeptide or CR-specific antibody is a protein or enzyme, or fragment thereof possessing a biological activity of the protein or enzyme, the active agent has an amino acid sequence identical to the amino acid sequence to the corresponding portion of the human or mammalian protein or enzyme. In other embodiments, the active agent moiety of the conjugate is a protein or enzyme native to the species of the human or mammal. In other embodiments, the protein or enzyme, or fragment thereof, is substantially homologous (i.e., at least 80%, 85%, 90%, 95%, more preferably 98%, or most preferably 99% identical in amino acid sequence over a length of at least 10, 25, 50, 100, 150, or 200 amino acids, or the entire length of the active agent) to a native sequence of the corresponding human or mammal protein or enzyme.

If the compound is a protein, the compound can be an enzyme, or any fragment of an enzyme that still retains some, substantially all, or all of the activity of the enzyme. Preferably, in the treatment of lysosomal storage diseases, the enzyme is an enzyme that is found in a cell that if not expressed or produced or is substantially reduced in expression or production would give rise to a lysosomal storage disease. Preferably, the enzyme is derived or obtained from a human or mouse. Preferably, the enzyme is a lysosomal storage enzyme, such as α-L-iduronidase, iduronate-2-sulfatase, heparan N-sulfatase, α-N-acetylglucosaminidase, arylsulfatase A, galactosylceramidase, acid-alpha-glucosidase, tripeptidyl peptidase, hexosaminidase alpha, acid sphingomyelinase, β-galactosidase, or any other lysosomal storage enzyme.

In some embodiments, therefore, in the treatment of human Lysosomal Storage Diseases (LSDs), the RAP variant (or CR-specific antibody-)-active agent conjugate comprises an active agent protein or enzyme that is deficient in the lysosomes of a subject or patient to be treated. Such enzymes, include for example, alpha-L-iduronidase, iduronate-2-sulfatase, heparan N-sulfatase, alpha-N-acetylglucosaminidase, Arylsulfatase A, Galactosylceramidase, acid-alpha-glucosidase, thioesterase, hexosaminidase A, Acid Spingomyelinase, alpha-galactosidase, or any other lysosomal storage enzyme. A table of lysosomal storage diseases and the proteins deficient therein, which are useful as active agents, follows:

| Lysosomal Storage Disease | Protein deficiency |
|---|---|
| Mucopolysaccharidosis type I | L-Iduronidase |
| Mucopolysaccharidosis type II Hunter syndrome | Iduronate-2-sulfatase |
| Mucopolysaccharidosis type IIIA Sanfilippo syndrome | Heparan-N-sulfatase |
| Mucopolysaccharidosis type IIIB Sanfilippo syndrome | α-N-Acetylglucosaminidase |
| Mucopolysaccharidosis type IIIC Sanfilippo syndrome | AcetylCoA:N-acetyltransferase |
| Mucopolysaccharidosis type IIID Sanfilippo syndrome | N-Acetylglucosamine 6-sulfatase |
| Mucopolysaccharidosis type IVA Morquio syndrome | Galactose 6-sulfatase |
| Mucopolysaccharidosis type IVB Morquio syndrome | β-Galactosidase |
| Mucopolysaccharidosis type VI | N-Acetylgalactosamine 4-sulfatase |
| Mucopolysaccharidosis type VII Sly syndrome | β-Glucuronidase |
| Mucopolysaccharidosis type IX | hyaluronoglucosaminidase |
| Aspartylglucosaminuria | Aspartylglucosaminidase |
| Cholesterol ester storage disease/Wolman disease | Acid lipase |
| Cystinosis | Cystine transporter |
| Danon disease | Lamp-2 |
| Fabry disease | α-Galactosidase A |
| Farber Lipogranulomatosis/Farber disease | Acid ceramidase |
| Fucosidosis | α-L-Fucosidase |
| Galactosialidosis types I/II | Protective protein |
| Gaucher disease types I/II/III Gaucher disease | Glucocerebrosidase (β-glucosidase) |
| Globoid cell leukodystrophy/Krabbe disease | Galactocerebrosidase |
| Glycogen storage disease II/Pompe disease | α-Glucosidase |
| GM1-Gangliosidosis types I/II/III | β-Galactosidase |
| GM2-Gangliosidosis type I/Tay Sachs disease | β-Hexosaminidase A |
| GM2-Gangliosidosis type II Sandhoff disease | β-Hexosaminidase A |
| GM2-Gangliosidosis | GM2-activator deficiency |
| α-Mannosidosis types I/II | α-D-Mannosidase |
| β-Mannosidosis | β-D-Mannosidase |
| Metachromatic leukodystrophy | Arylsulfatase A |
| Metachromatic leukodystrophy | Saposin B |

-continued

| Lysosomal Storage Disease | Protein deficiency |
|---|---|
| Mucolipidosis type I/Sialidosis types I/II | Neuraminidase |
| Mucolipidosis types II/III I-cell disease | Phosphotransferase |
| Mucolipidosis type IIIC pseudo-Hurler polydystrophy | Phosphotransferase γ-subunit |
| Multiple sulfatase deficiency | Multiple sulfatases |
| Neuronal Ceroid Lipofuscinosis, CLN1 Batten disease | Palmitoyl protein thioesterase |
| Neuronal Ceroid Lipofuscinosis, CLN2 Batten disease | Tripeptidyl peptidase I |
| Niemann-Pick disease types A/B Niemann-Pick disease | Acid sphingomyelinase |
| Niemann-Pick disease type C1 Niemann-Pick disease | Cholesterol trafficking |
| Niemann-Pick disease type C2 Niemann-Pick disease | Cholesterol trafficking |
| Pycnodysostosis | Cathepsin K |
| Schindler disease types I/II Schindler disease | α-Galactosidase B |
| Sialic acid storage disease | sialic acid transporter |

Thus, the lysosomal storage diseases that can be treated or prevented using the methods of the present invention include, but are not limited to, Mucopolysaccharidosis I (MPS I), MPS II, MPS IIIA, MPS IIIB, Metachromatic Leukodystrophy (MLD), Krabbe, Pompe, Ceroid Lipofuscinosis, Tay-Sachs, Niemann-Pick A and B, and other lysosomal diseases.

Thus, per the above table, for each disease the conjugated agent would preferably comprise a specific active agent enzyme deficient in the disease. For instance, for methods involving MPS I, the preferred compound or enzyme is α-L-iduronidase. For methods involving MPS II, the preferred compound or enzyme is iduronate-2-sulfatase. For methods involving MPS IIIA, the preferred compound or enzyme is heparan N-sulfatase. For methods involving MPS IIIB, the preferred compound or enzyme is α-N-acetylglucosaminidase. For methods involving Metachromatic Leukodystropy (MLD), the preferred compound or enzyme is arylsulfatase A. For methods involving Krabbe, the preferred compound or enzyme is galactosylceramidase. For methods involving Pompe, the preferred compound or enzyme is acid α-glucosidase. For methods involving CLN, the preferred compound or enzyme is tripeptidyl peptidase. For methods involving Tay-Sachs, the preferred compound or enzyme is hexosaminidase alpha. For methods involving Niemann-Pick A and B the preferred compound or enzyme is acid sphingomyelinase.

The RAP variant (or CR-specific antibody-)-active agent conjugate can comprise one or more active agent moieties (e.g., 1 to 10 or 1 to 4 or 2 to 3 moieties) linked to the RAP variant or megalin-binding fragment thereof or CR-specific antibody. For example, conjugation reactions may conjugate from 1 to 4 or more molecules of alpha-L-iduronidase to a single RAP variant or CR-specific antibody, such as a RAP variant polypeptide molecule. These formulations can be employed as mixtures, or they may be purified into specific RAP variant or CR-specific antibody polypeptide-agent stoichiometric formulations. Those skilled in the art are able to determine which format and which stoichiometric ratio is preferred. Further, one or more different active agents may be linked to any given molecule of a RAP variant or CR-specific antibody to facilitate a more complete degradation of the stored substrates. These RAP variant or CR-specific antibody conjugated agents may consist of a range of stoichiometric ratios. These, too, may be separated into purified mixtures or they may be employed in aggregate. It may be the order of RAP variant or CR-specific antibody and the LSD in the fusion is important for the ability of megalin binding moiety to bind to megalin. Therefore, in preferred embodiments, the RAP variant or CR-specific antibody is located N-terminally to the LSD enzyme coding sequence. In specific embodiments, it is contemplated that the conjugates of the invention comprise a RAP encoding sequence or CR-specific antibody located N-terminally to the LSD enzyme coding sequence.

The RAP variant- (or or CR-specific antibody-)conjugated active agents can enter or be transported into or end up residing in the lysosomes of a cell within or without the CNS. The rate of passage of the conjugated agent can be modulated by any compound or protein that can modulate megalin binding activity. In preferred embodiments, the non-LRP1 receptor binding affinity of the conjugate is higher than the LRP1 binding affinity. The cell can be from any tissue or organ system affected by the lysosomal storage disease. The cell can be, for instance, an endothelial, epithelial, muscle, heart, bone, lung, fat, kidney, or liver cell. In some embodiments, the cell is preferably a cell found within the BBB. In some embodiments, the cell is a neuron or a brain cell. In other embodiments, the cell is a cell of the periphery or one that is not isolated from the general circulation by an endothelium such as that of the BBB.

ii. Drug Active Agents

Generally, the drug active agent may be of any size. Preferred drugs are small organic molecules that are capable of binding to the target of interest. A drug moiety of the conjugate, when a small molecule, generally has a molecular weight of at least about 50 D, usually at least about 100 D, where the molecular weight may be as high as 500 D or higher, but will usually not exceed about 2000 D.

The drug moiety is capable of interacting with a target in the host into which the conjugate is administered during practice of the subject methods. The target may be a number of different types of naturally occurring structures, where targets of interest include both intracellular and extracellular targets, where such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZi domains, structural proteins, e.g., actin, tubulin, etc., membrane receptors, immunoglobulins, e.g., IgE, cell adhesion receptors, such as integrins, etc., ion channels, transmembrane pumps, transcription factors, signaling proteins, and the like.

In some embodiments, the active agent or drug has a hydroxyl or an amino group for reacting with the isocyanate reagent or the active agent is chemically modified to introduce a hydroxyl or an amino group for reacting with the isocyanate reagent.

In some embodiments, the active agent or drug comprises a region that may be modified and/or participate in covalent linkage, preferably, without loss of the desired biological activity of the active agent. The drug moieties often comprise cyclical carbon or heterocyclic structures and/or aromatic or polyaromatic structures substituted with one or more of the above functional groups. Also of interest as drug moieties are structures found among biomolecules, proteins, enzymes, polysaccharides, and polynucleic acids, including peptides, saccharides, fatty acids, steroids, purines, pyrimidines, derivatives, structural analogs or combinations thereof.

Suitable active agents include, but are not limited to, psychopharmacological agents, such as (1) central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g., central antitussives (opium alkaloids and their derivatives); pharmiacodynamic agents, such as (1) peripheral nervous system drugs, e.g., local anesthetics (ester derivatives, amide derivatives), (2) drugs acting at synaptic or neuroeffector junctional sites, e.g., cholinergic agents, cholinergic blocking agents, neuromuscular blocking agents, adrenergic agents, antiadrenergic agents, (3) smooth muscle active drugs, e.g., spasmolytics (anticholinergics, musculotropic spasmolytics), vasodilators, smooth muscle stimulants, (4) histamines and antihistamines, e.g., histamine and derivative thereof (betazole), antihistamines (H1-antagonists, H2-antagonists), histamine metabolism drugs, (5) cardiovascular drugs, e.g., cardiotonics (plant extracts, butenolides, pentadienolids, alkaloids from erythrophleum species, ionophores, adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g., antianemia drugs, blood coagulation drugs (hemostatics, anticoagulants, antithrombotics, thrombolytics, blood proteins and their fractions), (7) gastrointestinal tract drugs, e.g., digestants (stomachics, choleretics), antiulcer drugs, antidiarrheal agents, (8) locally acting drugs; chemotherapeutic agents, such as (1) anti-infective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e., antineoplastic agents or cytotoxic drugs, such as alkylating agents, e.g., Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g., Vincristine (Oncovin), Vinblastine (Velban, Velbe), Paclitaxel (Taxol), and the like; antimetabolites, e.g., Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g., Dactinomycin (Actinomycin D, Cosinegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g., Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like. Preferred chemotherapeutic agents are those, which in the free form, demonstrate unacceptable systemic toxicity at desired doses. The general systemic toxicity associated with therapeutic levels of such agents may be reduced by their linkage to the RAP variant polypeptide or CR-specific antibody. Particularly preferred are cardiotoxic compounds that are useful therapeutics but are dose limited by cardiotoxicity. A classic example is adriamycin (also known as doxorubicin) and its analogs, such as daunorubicin. Linking RAP or a RAP variant polypeptide or CR-specific antibody to such drugs may prevent accumulation of the active agent at the heart and associated cardiotoxicity.

Suitable active agents include, but are not limited to: Antibiotics, such as: aminoglycosides, e.g., amikacin, apramycin, arbekacin, bambermycins, butirosin, dibekacin, dihydrostreptomycin, fortirnicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; beta.-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin, etc.; polypeptides, e.g., amphomycin, bacitracin, capreomycin, etc.; tetracyclines, e.g., apicycline, chlortetracycline, clomocycline, etc.; synthetic antibacterial agents, such as 2,4-diaminopyrimidines, nitrofurans, quinolones and analogs thereof, sulfonamides, sulfones;

Suitable active agents include, but are not limited to: Antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, etc., thiocarbamates, e.g., tolciclate, triazoles, e.g., fluconazole, itraconazole, terconazole;

Suitable active agents include, but are not limited to: Antihelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

Suitable active agents include, but are not limited to: Antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

Suitable active agents include, but are not limited to: Antiprotozoan agents, such as: acranil, tinidazole, ipronidazole, ethylstibamine, pentamidine, acetarsone, aminitrozole, anisomycin, nifuratel, timidazole, benzidazole, suramin, and the like.

Suitable drugs for use as active agents are also listed in: Goodman and Gilman's, The Pharmacological Basis of Therapeutics (9th Ed) (Goodman et al. eds) (McGraw-Hill) (1996); and 1999 Physician's Desk Reference (1998).

Suitable active agents include, but are not limited to: antineoplastic agents, as disclosed in U.S. Pat. Nos. 5,880,161, 5,877,206, 5,786,344, 5,760,041, 5,753,668, 5,698,529, 5,684,004, 5,665,715, 5,654,484, 5,624,924, 5,618,813, 5,610,292, 5,597,831, 5,530,026, 5,525,633, 5,525,606, 5,512,678, 5,508,277, 5,463,181, 5,409,893, 5,358,952, 5,318,965, 5,223,503, 5,214,068, 5,196,424, 5,109,024, 5,106,996, 5,101,072, 5,077,404, 5,071,848, 5,066,493, 5,019,390, 4,996,229, 4,996,206, 4,970,318, 4,968,800, 4,962,114, 4,927,828, 4,892,887, 4,889,859, 4,886,790, 4,882,334, 4,882,333, 4,871,746, 4,863,955, 4,849,563, 4,845,216, 4,833,145, 4,824,955, 4,785,085, 4,684,747, 4,618,685, 4,611,066, 4,550,187, 4,550,186, 4,544,501, 4,541,956, 4,532,327, 4,490,540, 4,399,283, 4,391,982, 4,383,994, 4,294,763, 4,283,394, 4,246,411, 4,214,089, 4,150,231, 4,147,798, 4,056,673, 4,029,661, 4,012,448;

psychopharmacological/psychotropic agents, as disclosed in U.S. Pat. Nos. 5,192,799, 5,036,070, 4,778,800, 4,753,951, 4,590,180, 4,690,930, 4,645,773, 4,427,694, 4,424,202, 4,440,781, 5,686,482, 5,478,828, 5,461,062, 5,387,593, 5,387,586, 5,256,664, 5,192,799, 5,120,733, 5,036,070, 4,977,167, 4,904,663, 4,788,188, 4,778,800, 4,753,951, 4,690,930, 4,645,773, 4,631,285, 4,617,314, 4,613,600, 4,590,180, 4,560,684, 4,548,938, 4,529,727, 4,459,306, 4,443,451, 4,440,781, 4,427,694, 4,424,202, 4,397,853, 4,358,451, 4,324,787, 4,314,081, 4,313,896, 4,294,828, 4,277,476, 4,267,328, 4,264,499, 4,231,930, 4,194,009, 4,188,388, 4,148,796, 4,128,717, 4,062,858, 4,031,226, 4,020,072, 4,018,895, 4,018,779, 4,013,672, 3,994,898, 3,968,125, 3,939,152, 3,928,356, 3,880,834, 3,668,210;

cardiovascular agents, as disclosed in U.S. Pat. Nos. 4,966,967, 5,661,129, 5,552,411, 5,332,737, 5,389,675, 5,198,449, 5,079,247, 4,966,967, 4,874,760, 4,954,526, 5,051,423, 4,888,335, 4,853,391, 4,906,634, 4,775,757, 4,727,072, 4,542,160, 4,522,949, 4,524,151, 4,525,479, 4,474,804, 4,520,026, 4,520,026, 5,869,478, 5,859,239, 5,837,702, 5,807,889, 5,731,322, 5,726,171, 5,723,457, 5,705,523, 5,696,111, 5,691,332, 5,679,672, 5,661,129, 5,654,294, 5,646,276, 5,637,586, 5,631,251, 5,612,370, 5,612,323, 5,574,037, 5,563,170, 5,552,411, 5,552,397, 5,547,966, 5,482,925, 5,457,118, 5,414,017, 5,414,013, 5,401,758, 5,393,771, 5,362,902, 5,332,737, 5,310,731, 5,260,444, 5,223,516, 5,217,958, 5,208,245, 5,202,330, 5,198,449, 5,189,036, 5,185,362, 5,140,031, 5,128,349, 5,116,861, 5,079,247, 5,070,099, 5,061,813, 5,055,466, 5,051,423, 5,036,065, 5,026,712, 5,011,931, 5,006,542, 4,981,843, 4,977,144, 4,971,984, 4,966,967, 4,959,383, 4,954,526, 4,952,692, 4,939,137, 4,906,634, 4,889,866, 4,888,335, 4,883,872, 4,883,811, 4,847,379, 4,835,157, 4,824,831, 4,780,538, 4,775,757, 4,774,239, 4,771,047, 4,769,371, 4,767,756, 4,762,837, 4,753,946, 4,752,616, 4,749,715, 4,738,978, 4,735,962, 4,734,426, 4,734,425, 4,734,424, 4,730,052, 4,727,072, 4,721,796, 4,707,550, 4,704,382, 4,703,120, 4,681,970, 4,681,882, 4,670,560, 4,670,453, 4,668,787, 4,663,337, 4,663,336, 4,661,506, 4,656,267, 4,656,185, 4,654,357, 4,654,356, 4,654,355, 4,654,335, 4,652,578, 4,652,576, 4,650,874, 4,650,797, 4,649,139, 4,647,585, 4,647,573, 4,647,565, 4,647,561, 4,645,836, 4,639,461, 4,638,012, 4,638,011, 4,632,931, 4,631,283, 4,628,095, 4,626,548, 4,614,825, 4,611,007, 4,611,006, 4,611,005, 4,609,671, 4,608,386, 4,607,049, 4,607,048, 4,595,692, 4,593,042, 4,593,029, 4,591,603, 4,588,743, 4,588,742, 4,588,741, 4,582,854, 4,575,512, 4,568,762, 4,560,698, 4,556,739, 4,556,675, 4,555,571, 4,555,570, 4,555,523, 4,550,120, 4,542,160, 4,542,157, 4,542,156, 4,542,155, 4,542,151, 4,537,981, 4,537,904, 4,536,514, 4,536,513, 4,533,673, 4,526,901, 4,526,900, 4,525,479, 4,524,151, 4,522,949, 4,521,539, 4,520,026, 4,517,188, 4,482,562, 4,474,804, 4,474,803, 4,472,411, 4,466,979, 4,463,015, 4,456,617, 4,456,616, 4,456,615, 4,418,076, 4,416,896, 4,252,815, 4,220,594, 4,190,587, 4,177,280, 4,164,586, 4,151,297, 4,145,443, 4,143,054, 4,123,550, 4,083,968, 4,076,834, 4,064,259, 4,064,258, 4,064,257, 4,058,620, 4,001,421, 3,993,639, 3,991,057, 3,982,010, 3,980,652, 3,968,117, 3,959,296, 3,951,950, 3,933,834, 3,925,369, 3,923,818, 3,898,210, 3,897,442, 3,897,441, 3,886,157, 3,883,540, 3,873,715, 3,867,383, 3,873,715, 3,867,383, 3,691,216, 3,624,126;

antimicrobial agents as disclosed in U.S. Pat. Nos. 5,902,594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,746,504, 4,686,221, 4,599,228, 4,552,882, 4,492,700, 4,489,098, 4,489,085, 4,487,776, 4,479,953, 4,477,448, 4,474,807, 4,470,994, 4,370,484, 4,337,199, 4,311,709, 4,308,283, 4,304,910, 4,260,634, 4,233,311, 4,215,131, 4,166,122, 4,141,981, 4,130,664, 4,089,977, 4,089,900, 4,069,341, 4,055,655, 4,049,665, 4,044,139, 4,002,775, 3,991,201, 3,966,968, 3,954,868, 3,936,393, 3,917,476, 3,915,889, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,620, 5,665,752, 5,656,661, 5,635,516, 5,631,283, 5,622,948, 5,618,835, 5,607,959, 5,593,980, 5,593,960, 5,580,888, 5,552,424, 5,552,422, 5,516,764, 5,510,361, 5,508,026, 5,500,417, 5,498,405, 5,494,927, 5,476,876, 5,472,973, 5,470,885, 5,470,842, 5,464,856, 5,464,849, 5,462,952, 5,459,151, 5,451,686, 5,444,043, 5,436,265, 5,432,181, RE034918, 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,937, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 5,006,542, 4,992,448, 4,992,447, 4,988,733, 4,988,728, 4,981,865, 4,962,119, 4,959,378, 4,954,519, 4,945,099, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598; 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 4,558,067, 4,556,672, 4,556,669, 4,539,326, 4,537,903, 4,536,503, 4,518,608, 4,514,415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,693,648, 5,693,645, 5,691,346, 5,686,469, 5,686,424, 5,679,705, 5,679,640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 5,262,533, 5,260,300, 5,252,732, 5,250,678, 5,247,076, 5,244,896, 5,238,689, 5,219,884, 5,208,241, 5,208,228, 5,202,332, 5,192,773, 5,189,042, 5,169,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

immunomodulatory agents, as disclosed in U.S. Pat. Nos. 4,446,128, 4,524,147, 4,720,484, 4,722,899, 4,748,018, 4,877,619, 4,998,931, 5,049,387, 5,118,509, 5,152,980, 5,256,416, 5,468,729, 5,583,139, 5,604,234, 5,612,060, 5,612,350, 5,658,564, 5,672,605, 5,681,571, 5,708,002, 5,723,718, 5,736,143, 5,744,495, 5,753,687, 5,770,201, 5,869,057, 5,891,653, 5,939,455, 5,948,407, 6,006,752, 6,024,957, 6,030,624, 6,037,372, 6,037,373, 6,043,247, 6,060,049, 6,087,096, 6,096,315, 6,099,838, 6,103,235, 6,124,495, 6,153,203, 6,169,087, 6,255,278, 6,262,044, 6,290,950, 6,306,651, 6,322,796, 6,329,153, 6,344,476, 6,352,698, 6,365,163, 6,379,668, 6,391,303, 6,395,767, 6,403,555, 6,410,556, 6,412,492, 6,468,537, 6,489,330, 6,521,232, 6,525,035, 6,525,242, 6,558,663, 6,572,860;

analgesic agents, as disclosed in U.S. Pat. Nos. 5,292,736, 5,688,825, 5,554,789, 5,455,230, 5,292,736, 5,298,522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514, 4,147,872, 4,133,819, 4,124,713, 4,117,012, 4,064,272, 4,022,836, 3,966,944;

cholinergic agents, as disclosed in U.S. Pat. Nos. 5,219,872, 5,219,873, 5,073,560, 5,073,560, 5,346,911, 5,424,301, 5,073,560, 5,219,872, 4,900,748, 4,786,648, 4,798,841, 4,782,071, 4,710,508, 5,482,938, 5,464,842, 5,378,723, 5,346,911, 5,318,978, 5,219,873, 5,219,872, 5,084,281, 5,073,560, 5,002,955, 4,988,710, 4,900,748, 4,798,841, 4,786,648, 4,782,071, 4,745,123, 4,710,508;

adrenergic agents, as disclosed in U.S. Pat. Nos. 5,091,528, 5,091,528, 4,835,157, 5,708,015, 5,594,027, 5,580,892, 5,576,332, 5,510,376, 5,482,961, 5,334,601, 5,202,347, 5,135,926, 5,116,876, 5,091,528, 5,017,618, 4,835,157, 4,829,086, 4,579,867, 4,568,679, 4,469,690, 4,395,559, 4,381,309, 4,363,808, 4,343,800, 4,329,289, 4,314,943, 4,311,708, 4,304,721, 4,296,117, 4,285,873, 4,281,189, 4,278,608, 4,247,710, 4,145,550, 4,145,425, 4,139,535, 4,082,843, 4,011,321, 4,001,421, 3,982,010, 3,940,407, 3,852,468, 3,832,470;

antihistamine agents, as disclosed in U.S. Pat. Nos. 5,874,479, 5,863,938, 5,856,364, 5,770,612, 5,702,688, 5,674,912, 5,663,208, 5,658,957, 5,652,274, 5,648,380, 5,646,190, 5,641,814, 5,633,285, 5,614,561, 5,602,183, 4,923,892, 4,782,058, 4,393,210, 4,180,583, 3,965,257, 3,946,022, 3,931,197;

steroidal agents, as disclosed in U.S. Pat. Nos. 5,863,538, 5,855,907, 5,855,866, 5,780,592, 5,776,427, 5,651,987, 5,346,887, 5,256,408, 5,252,319, 5,209,926, 4,996,335, 4,927,807, 4,910,192, 4,710,495, 4,049,805, 4,004,005, 3,670,079, 3,608,076, 5,892,028, 5,888,995, 5,883,087, 5,880,115, 5,869,475, 5,866,558, 5,861,390, 5,861,388, 5,854,235, 5,837,698, 5,834,452, 5,830,886, 5,792,758, 5,792,757, 5,763,361, 5,744,462, 5,741,787, 5,741,786, 5,733,899, 5,731,345, 5,723,638, 5,721,226, 5,712,264, 5,712,263, 5,710,144, 5,707,984, 5,705,494, 5,700,793, 5,698,720, 5,698,545, 5,696,106, 5,677,293, 5,674,861, 5,661,141, 5,656,621, 5,646,136, 5,637,691, 5,616,574, 5,614,514, 5,604,215, 5,604,213, 5,599,807, 5,585,482, 5,565,588, 5,563,259, 5,563,131, 5,561,124, 5,556,845, 5,547,949, 5,536,714, 5,527,806, 5,506,354, 5,506,221, 5,494,907, 5,491,136, 5,478,956, 5,426,179, 5,422,262, 5,391,776, 5,382,661, 5,380,841, 5,380,840, 5,380,839, 5,373,095, 5,371,078, 5,352,809, 5,344,827, 5,344,826, 5,338,837, 5,336,686, 5,292,906, 5,292,878, 5,281,587, 5,272,140, 5,244,886, 5,236,912, 5,232,915, 5,219,879, 5,218,109, 5,215,972, 5,212,166, 5,206,415, 5,194,602, 5,166,201, 5,166,055, 5,126,488, 5,116,829, 5,108,996, 5,099,037, 5,096,892, 5,093,502, 5,086,047, 5,084,450, 5,082,835, 5,081,114, 5,053,404, 5,041,433, 5,041,432, 5,034,548, 5,032,586, 5,026,882, 4,996,335, 4,975,537, 4,970,205, 4,954,446, 4,950,428, 4,946,834, 4,937,237, 4,921,846, 4,920,099, 4,910,226, 4,900,725, 4,892,867, 4,888,336, 4,885,280, 4,882,322, 4,882,319, 4,882,315, 4,874,855, 4,868,167, 4,865,767, 4,861,875, 4,861,765, 4,861,763, 4,847,014, 4,774,236, 4,753,932, 4,711,856, 4,710,495, 4,701,450, 4,701,449, 4,689,410, 4,680,290, 4,670,551, 4,664,850, 4,659,516, 4,647,410, 4,634,695, 4,634,693, 4,588,530, 4,567,000, 4,560,557, 4,558,041, 4,552,871, 4,552,868, 4,541,956, 4,519,946, 4,515,787, 4,512,986, 4,502,989, 4,495,102; the disclosures of all the above of which are herein incorporated by reference.

The drug moiety of the conjugate may be the whole drug or a binding fragment or portion thereof that retains its affinity and specificity for the target of interest while having a linkage site for covalent bonding to the vector protein ligand or linker. The conjugates of such drugs may be used for the same disorders, diseases, and indications as the drugs themselves.

iii. Preferred Cancer Chemotherapeutic Active Agents

Preferred cancer chemotherapeutic agents for use in the RAP variant or CR-specific antibody based conjugates of the invention include all drugs which may be useful for treating brain tumors or other neoplasia in or around the brain, either in the free form, or, if not so useful for such tumors in the free form, useful when linked to the RAP variant or megalin binding fragment thereof or CR-specific antibody. Such chemotherapeutic agents are preferably cytotoxic chemotherapeutic agents including but not limited to adriarnycin (also known as doxorubicin), cisplatin, paclitaxel, analogs thereof, and other chemotherapeutic agents demonstrate activity against tumours ex vivo and in vivo. Such chemotherapeutic agents also include alkylating agents, antimetabolites, natural products (such as vinca alkaloids, epidophyllotoxins, antibiotics, enzymes and biological response modifiers), topoisomerase inhibitors, microtubule inhibitors, spindle poisons, hormones and antagonists, and miscellaneous agents such as platinum coordination complexes, anthracendiones, substituted ureas, etc. Those of skill in the art will know of other chemotherapeutic agents.

Preferred chemotherapeutic agents are those, which in the free form, demonstrate unacceptable systemic toxicity at desired doses. The general systemic toxicity associated with therapeutic levels of such agents is reduced by their linkage to a RAP variant or CR-specific antibody. Particularly preferred are cardiotoxic compounds that are useful therapeutics but are dose limited by cardiotoxicity. A classic example is adriamycin (also known as doxorubicin) and its analogs, such as daunorubicin. Linking a RAP variant or CR-specific antibody to such drugs decreases accumulation and associated cardiotoxicity at the heart.

iv. Glycoconjugates

Glycoconjugates are any molecule which includes a carbohydrate portion. Examples include, but are not limited to, glycoproteins, oligosaccharides, glycolipids and proteoglycans. Such molecules have beneficial functions such as enhancement of bioavailability of therapeutic agents or ability to block pathogenic mechanisms. For example, alpha-L-iduronidase is a glycoconjugate (glycoprotein) that is efficiently distributed throughout the body because of the oligomannose 7-bispbosphate determinant attached to the enzyme. Heparin sulfate is a carbohydrate portion of a proteoglycan that is useful for blocking coagulation pathways in humans. Attachment of suitable RAP variants or CR-specific antibody to glycoconjugates with therapeutic activities may provide a means of increasing the potency of the glycoconjugate by affecting biodistribution. Alternatively, RAP variant- (or CR-specific antibody-)glycoconjugate fusions may be engineered to act as bis-specific receptor-binding molecules with the ability to directly affect the functions of one or more receptors in specific tissues.

v. Nanoparticles

Nanoparticles are macromolecular assemblies constructed from biodegradable and non-biodegradable polymers or from other materials such as lipids. Such assemblies may be engineered to contain therapeutic molecules in cavities within the particle. Through this means, nanoparticles provide a means of altering the biodistribution, pharmacokinetics, immunogenicity and potency of drugs. Attachment of suitable RAP variants or CR-specific antibodies would, in turn, provide a means of increasing the specificity of tissue distribution of these-molecules.

H. Methods of Producing RAP Conjugates i. Host Cells

Host cells used to produce chimeric proteins are bacterial, yeast, insect, non-mammalian vertebrate, or mammalian cells; the mammalian cells include, but are not limited to, hamster, monkey, chimpanzee, dog, cat, bovine, porcine, mouse, rat, rabbit, sheep and human cells. The host cells can be inunnortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types. Host cells can include mutants of CHO cells that do not express LRP such as CHO13-5-1 (FitzGerald et al., J. Biol. Chem., 129(6):1533-41, 1995).

Cells that contain and express DNA or RNA encoding the chimeric protein are referred to herein as genetically modified cells. Mammalian cells that contain and express DNA or RNA encoding the chimeric protein are referred to as genetically modified mammalian cells. Introduction of the DNA or RNA into cells is by a known transfection method, such as electroporation, microinjection, microprojectile bombardment, calcium phosphate precipitation, modified calcium phosphate precipitation, cationic lipid treatment, photoporation, fusion methodologies, receptor mediated transfer, or polybrene precipitation. Alternatively, the DNA or RNA can be introduced by infection with a viral vector. Methods of producing cells, including mammalian cells, which express DNA or RNA encoding a chimeric protein are described in U.S. Pat. Nos. 6,048,729, 5,994,129, and 6,063,630. The teachings of each of these applications are expressly incorporated herein by reference in their entirety.

ii. Nucleic Acid Constructs

A nucleic acid construct used to express the chimeric protein can be one which is expressed extrachromosomally (episomally) in the transfected mammalian cell or one which integrates, either randomly or at a pre-selected targeted site through homologous recombination, into the recipient cell's genome. A construct which is expressed extrachromosomally comprises, in addition to chimeric protein-encoding sequences, sequences sufficient for expression of the protein in the cells and, optionally, for replication of the construct. It typically includes a promoter, chimeric protein-encoding DNA and a polyadenylation site. The DNA encoding the chimeric protein is positioned in the construct in such a manner that its expression is under the control of the promoter. Optionally, the construct may contain additional components such as one or more of the following: a splice site, an enhancer sequence, a selectable marker gene under the control of an appropriate promoter, and an amplifiable marker gene under the control of an appropriate promoter.

In those embodiments in which the DNA construct integrates into the cell's genome, it need include only the chimeric protein-encoding nucleic acid sequences. Optionally, it can include a promoter and an enhancer sequence, a polyadenylation site or sites, a splice site or sites, nucleic acid sequences which encode a selectable marker or markers, nucleic acid sequences which encode an amplifiable marker and/or DNA homologous to genomic DNA in the recipient cell to target integration of the DNA to a selected site in the genome (targeting DNA or DNA sequences).

iii. Cell Culture Methods

Mammalian cells containing the chimeric protein-encoding DNA or RNA are cultured under conditions appropriate for growth of the cells and expression of the DNA or RNA. Those cells which express the chimeric protein can be identified, using known methods and methods described herein, and the chimeric protein isolated and purified, using known methods and methods also described herein; either with or without amplification of chimeric protein production. Identification can be carried out, for example, through screening genetically modified mammalian cells displaying a phenotype indicative of the presence of DNA or RNA encoding the chimeric protein, such as PCR screening, screening by Southern blot analysis, or screening for the expression of the chimeric protein. Selection of cells having incorporated chimeric protein-encoding DNA may be accomplished by including a selectable marker in the DNA construct and culturing transfected or infected cells containing a selectable marker gene under conditions appropriate for survival of only those cells that express the selectable marker gene. Further amplification of the introduced DNA construct can be affected by culturing genetically modified mammalian cells under conditions appropriate for amplification (e.g., culturing genetically modified mammalian cells containing an amplifiable marker gene in the presence of a concentration of a drug at which only cells containing multiple copies of the amplifiable marker gene can survive).

Genetically modified mammalian cells expressing the chimeric protein can be identified, as described herein, by detection of the expression product. For example, mammalian cells expressing chimeric protein in which the carrier is a RAP variant can be identified by a sandwich enzyme immunoassay. The antibodies can be directed toward the megalin-binding portion or the active agent portion of the conjugate.

iv. Production of RAP Variant Polypeptides

RAP variant polypeptides for use according to the invention include those disclosed in U.S. Pat. No. 5,474,766 that is enclosed herein by reference in its entirety for the purposes of disclosing such peptides and their production for use in the compounds and compositions of the present invention. RAP variant polypeptides is produced using any of protein preparation and purification methods known to those of skill in the art.

The ligand is purified from a naturally occurring source of the protein, can be isolated from a recombinant host expressing the ligand, or synthesized using well known techniques in protein synthesis. A skilled artisan readily adapts a variety of such techniques in order to obtain a RAP variant that contain the receptor-binding site. (Melman et al., J. Biol. Chem. 276 (31): 29338-29346 (2001); Savonen et al., J Biol. Chem. 274(36): 25877-25882 (1999); Nielsen et al. Proc. Natl. Acad. Sci. USA 94:7521-7525 (1997); Medved et al., J. Biol. Chem. 274(2): 717-727 (1999); Rall et al., J. Biol. Chem. 273(37): 24152-24157 (1998); Orlando et al., Proc. Natl. Acad. Sci. USA 3161-3163 (1994)).

The isolation of native RAP proteins has been previously described (Ashcom et al., J. Cell. Biol. 110:1041-1048 (1990) and Jensen et al., FEBS Lett. 255:275-280 (1989)). RAP variant fragments are generated from isolated native protein which are converted by enzymatic and/or chemical cleavage to generate fragments of the whole protein. U.S. Pat. No. 6,447,775 is herein incorporated by reference with particular reference to such methods for obtaining RAP variant polypeptides. In addition, the RAP variant are expressed in a recombinant bacteria (Williams et al., J. Biol. Chem. 267: 9035-9040 (1992); Wurshawsky et al., J. Biol. Chem. 269: 3325-3330 (1994)). Procedures for purifying the 39 kDa RAP protein from a recombinant E. coli strain have been previously described (Herz et al., J. Biol. Chem. 266, 21232-21238 (1991); U.S. Pat. No. 5,474,766).

Cultures of E. coli strain DH5alpha carrying the expression plasmid pGEX-39 kDa are grown to mid-log phase in LB medium with 100 µg/ml ampicillin at 37° C. Cultures are cooled to 30° C. and supplemented with 0.01% isopropylthio-beta-D-galactoside to induce expression of the glutathione-S-transferase-39 kDa fusion protein. Following a 4-6 hour induction at 30° C., cultures are cooled with ice and recovered by centrifugation. Further steps are conducted at 4° C. Cell pellets are lysed in PBS with 1% Triton X-100, 1 µM pepstatin, 2.5 µg/ml leupeptin, 0.2 mM phenylmethylsulfonyl fluoride (PMSF), and 1 µM ethylenediaminetetraacetate (EDTA). The lysate is sonicated with a Branson Model 450 Sonifier and the resulting membranes and other cellular debris are separated by centrifugation at 15,000 g for 15 minutes. The recovered supernatant is incubated overnight with agarose immobilized glutathione beads (Sigma Chemical Co.) in PBS and 0.1% sodium azide. The beads are washed, and the fusion protein eluted by competition with 5 mM reduced glutathione (Sigma Chemical Co.). Following dialysis, the fusion protein is cleaved by an overnight incubation with 100 ng of activated human thrombin per 50 µg of fusion protein. The glutathione-S-transferase epitope is subsequently be removed by further incubation with agarose immobilized glutathione beads.

While the above method is described for the production and purification of RAP, as indicated above, other RAP variants also may be produced using similar techniques. A review of such ligands may be found in Christensen and Bim, (Am. J. Physiol. Renal Physiol., 280:F562-F573, 2001, see particularly Table 1 and references cited therein) Techniques for making and purifying such ligands are well known to those of skill in the art.

I. Characterization of RAP Conjugates i. Labels

In some embodiments, the RAP variant-based active agent conjugate or CR-specific antibody or antibody conjugate is labeled to facilitate its detection. A "label" or a "detectable moiety" is a composition detectable by spectroscopic, photochemical, biochemical, immunochemical, chemical, or other physical means. For example, labels suitable for use in the present invention include, for example, radioactive labels (e.g., 32P), fluorophores (e.g., fluorescein), electron dense reagents, enzymes (e.g., as commonly used in an ELISA), biotin, digoxigenin, or haptens and proteins which can be made detectable, e.g., by incorporating a radiolabel into the hapten or peptide, or used to detect antibodies specifically reactive with the hapten or peptide.

As noted above, depending on the screening assay employed, the active agent, the linker or the RAP variant polypeptide portion of a conjugate or CR-specific antibody may be labeled. The particular label or detectable group used is not a critical aspect of the invention, as long as it does not significantly interfere with the biological activity of the conjugate. The detectable group can be any material having a detectable physical or chemical property. Thus, a label is any composition detectable by spectroscopic, photochemical, biochemical, immunochemical, electrical, optical or chemical means.

Examples of labels suitable for use in the present invention include, but are not limited to, fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. Preferably, the label in one embodiment is covalently bound to the biopolymer using an isocyanate reagent for conjugating an active agent according to the invention. In one aspect of the invention, the bifunctional isocyanate reagents of the invention can be used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand binds to another molecules (e.g., streptavidin) molecule, which is either inherently detectable or covalently bound to a signal system, such as a detectable enzyme, a fluorescent compound, or a chemiluminescent compound.

The conjugates can also be conjugated directly to signal generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands may be used in the diagnosis of a disease or health condition.

ii. Screening Assays for RAP Variant-Active Agent Conjugates, CR-Specific Antibodies, and Modulators of their Delivery The present invention provides a screening assay for RAP variant polypeptide- (or CR-specific antibody-)active agent conjugates, wherein the conjugates are tested for their ability to influence a measurable activity of a specific receptor which can be situated in a whole cell, a cell extract, semi-purified, purified or any other format that allows for measurement of its activity. The activity can be any activity in the expression, function or degradation of megalin including, for example, the amount or timing of such activities. Such activities include, for example, transcription, transcript processing, translation or transcript stability of the receptor gene sequence or mRNA transcript. Such activities include, for example, the synthesis of new receptor, the sub-cellular localization of the receptor and activation of receptor biological activity. Such activities include, for example, the ability of the receptor to bind substances, adopt conformations, catalyze reactions, bind known ligands and the like. Such activities include, for example, the amount or stability of the receptor, the processing and removal or degradation of the receptor and the like. In preferred embodiments, the RAP variant used is one which has been modified or naturally has a higher binding affinity for the targeted receptor than for any other receptor.

The invention contemplates a variety of different screening formats. Some designs are considered low throughput and test only one or a few compounds in series or in parallel. High throughput screening assays are suitable for screening tens of thousands or hundreds of thousands of compounds in a matter of weeks or months. "In silico" screening formats employ computer-aided rational design techniques to identify potential modulators of megalin biological activity.

J. Methods of Using, Pharmaceutical Compositions, and Their Administration

The conjugates and modulators may be administered by a variety of routes. For oral preparations, the conjugates can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The conjugates and modulators can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The conjugates, modulators, and LDLR ligands can be utilized in aerosol formulation to be administered via inhalation. The compounds of the present invention can be formulated into pressurized acceptable propellants such as dichlorodifluoromethane, propane, nitrogen and the like.

Furthermore, the conjugates and modulators can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms of the conjugate, modulator, and LDLR ligand for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the conjugate in a composition as a solution in sterile water, normal saline or another pharmaceutically acceptable carrier.

In practical use, the conjugate, modulator, and LDLR ligand according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

With respect to transdermal routes of administration, methods for transdermal administration of drugs are disclosed in Remington's Pharmaceutical Sciences, 17th Edition, (Gennaro et al. Eds. Mack Publishing Co., 1985). Dermal or skin patches are a preferred means for transdermal delivery of the conjugates, modulators, and LRP ligands of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

In specific embodiments, it is contemplated that the therapeutic administering of the conjugates described herein will be administered intrathecally into the CSF. The intrathecal administration of the present invention may comprise introducing the pharmaceutical composition into a cerebral ventricle. Alternatively, the intrathecal administration may comprise introducing the pharmaceutical composition into the lumbar area. In yet another alternative, the intrathecal administration comprises introducing the pharmaceutical composition into the cisterna magna. Any such administration is preferably via a bolus injection. Depending on the severity of the symptoms and the responsiveness of the subject to the therapy, such a bolus injection may be administered once per week, once per month, once every 6 months or annually. In other embodiments, the intrathecal administration is achieved by use of an infusion pump. The pharmaceutical could of course be intrathecally administered continually over a period of at least several days or alternatively, the intrathecal administration is continually over a period of at least four weeks. Of course, where the administration is via continuous infusion, the rate of dose administration of the enzyme replacement therapy may be greatly reduced as compared to the bolus injection administration. In preferred embodiments, the active agent of the conjugate is iduronidase and it is delivered in an amount that comprises about 1 mg iduronidase/20 kg of body weight of the mammal being treated for MPS. In particular embodiments, the above dose is delivered to 15 cc CSF. At such a concentration it is contemplated that the enzyme concentration will be 18,000 units per ml of CSF. It should be understood that the aforementioned dosage is merely an exemplary dosage and those of skill in the art will understand that this dosage may be varied.

The methods and compositions of the invention may be combined with methods and compositions of inducing antigen specific tolerance prior to the enzyme replacement therapy. Such methods include inducing antigen specific tolerance comprises administration of an immunosuppressive agent, such as e.g., cyclosporine A and may further comprise administration of an antiproliferative agent, including but not limited to a nucleotide analog or an anti-metabolite. The antiproliferative agent may be azathioprine. Further methods are described in e.g., U.S. patent application Ser. No. 10/141, 668, published as U.S. Publication No. 20030211113; and U.S. patent application Ser. No. 10/429,314 published as U.S. Publication No. 20040009906, each incorporated herein by reference.

Pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available.

Those of skill will readily appreciate that dose levels can vary as a function of the specific compound, the severity of the symptoms and the susceptibility of the subject to side effects. Preferred dosages for a given compound are readily determinable by those of skill in the art by a variety of means, including, but not limited to dose response and pharmacokinetic assessments conducted in patients, test animals, and in vitro.

In each of these aspects, the compositions include, but are not limited to, compositions suitable for oral, rectal, topical, parenteral (including subcutaneous, intramuscular, and intravenous), pulmonary (nasal or buccal inhalation), or nasal administration, although the most suitable route in any given case will depend in part on the nature and severity of the conditions being treated and on the nature of the active ingredient. Exemplary routes of administration are the oral and intravenous routes. The compositions may be conveniently presented in unit dosage form and prepared by any of the methods well-known in the art of pharmacy.

In practical use, the modulators or according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. The percentage of an active compound in these compositions may, of course, be varied and may conveniently be between about 2 percent to about 60 percent of the weight of the unit.

The conjugates, modulators, and ligands of the invention are useful for therapeutic, prophylactic and diagnostic intervention in animals, and in particular in humans. As described herein, the conjugates show preferential accumulation and/or release of the active agent in any target organ, compartment, or site depending upon the biopolymer used.

Compositions of the present invention may be administered encapsulated in or attached to viral envelopes or vesicles, or incorporated into cells. Vesicles are micellular particles which are usually spherical and which are frequently lipidic. Liposomes are vesicles formed from a bilayer membrane. Suitable vesicles include, but are not limited to, unilamellar vesicles and multilamellar lipid vesicles or liposomes. Such vesicles and liposomes may be made from a wide range of lipid or phospholipid compounds, such as phosphatidylcholine, phosphatidic acid, phosphatidylserine, phosphatidylethanolamine, sphingomyelin, glycolipids, gangliosides, etc. using standard techniques, such as those described in, e.g., U.S. Pat. No. 4,394,448. Such vesicles or liposomes may be used to administer compounds intracellularly and to deliver compounds to the target organs. Controlled release of a p97-composition of interest may also be achieved using encapsulation (see, e.g., U.S. Pat. No. 5,186,941).

Any route of administration that delivers the RAP variant, CR-specific antibody, RAP variant-based active agent conjugate or modulator composition into the blood stream, or preferably at least outside of the blood-brain barrier, may be used. Preferably, the composition is administered peripherally, most preferably intravenously or by cardiac catheter. Intrajugular and intracarotid injections are also useful. Compositions may be administered locally or regionally, such as intraperitoneally or subcutaneously on intramuscularly. In one aspect, compositions are administered with a suitable pharmaceutical diluent or carrier.

Dosages to be administered will depend on individual needs, on the desired effect, the active agent used, the biopolymer and on the chosen route of administration. Preferred dosages of a conjugate range from about 0.2 pmol/kg to about 25 nmol/kg, and particularly preferred dosages range from 2-250 pmol/kg; alternatively, preferred doses of the conjugate may be in the range of 0.02 to 2000 mg/kg. These dosages will be influenced by the number of active agent or drug moieties associated with the biopolymer. Alternatively, dosages may be calculated based on the active agent administered.

In preferred embodiments the conjugate comprises a RAP variant. For instance, doses of RAP variant-adriamycin comprising from 0.005 to 100 mg/kg of adriamycin are also useful in vivo. Particularly preferred is a dosage of RAP variant-adriamycin comprising from 0.05 mg/kg to 20 mg/kg of adriamycin. Those skilled in the art can determine suitable doses for compounds linked to a RAP variant based in part on the recommended dosage used for the free form of the compound. Conjugation of the active agent to a RAP variant generally reduces the amount of drug needed to obtain the same effect.

The conjugates and modulators of the invention are useful for therapeutic, prophylactic and diagnostic intervention in animals, and in particular in humans. RAP variant compounds may show preferential accumulation in particular tissues. Preferred medical indications for diagnostic uses include, for example, any condition associated with a target organ of interest (e.g., lung, liver, kidney, spleen). In particularly preferred embodiments, the target organ of interest in the brain.

The subject methods find use in the treatment of a variety of different disease conditions. In certain embodiments, of particular interest is the use of the subject methods in disease conditions where an active agent or drug having desired activity has been previously identified, but in which the active agent or drug is not adequately delivered to the target site, area or compartment to produce a fully satisfactory therapeutic result. With such active agents or drugs, the subject methods of conjugating the active agent to a RAP variant or CR-specific antibody can be used to enhance the therapeutic efficacy and therapeutic index of active agent or drug.

The specific disease conditions treatable by with the subject conjugates are as varied as the types of drug moieties that can be present in the conjugate. Thus, disease conditions include cellular proliferative diseases, such as neoplastic diseases, autoimmune diseases, cardiovascular diseases, hormonal abnormality diseases, degenerative diseases, diseases of aging, diseases of the central nervous system (e.g., Alzheimer's disease, epilepsy, hyperlipidemias), psychiatric diseases and conditions (e.g., schizophrenia, mood disorders such as depression and anxiety), infectious diseases, enzyme deficiency diseases, lysosomal storage diseases such as those described above, and the like.

Treatment is meant to encompass any beneficial outcome to a subject associated with administration of a conjugate including a reduced likelihood of acquiring a disease, prevention of a disease, slowing, stopping or reversing, the progression of a disease or an amelioration of the symptoms associated with the disease condition afflicting the host, where amelioration or benefit is used in a broad sense to refer to at least a reduction in the magnitude of a parameter, e.g., symptom, associated with the pathological condition being treated, such as inflammation and pain associated therewith. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

In specific embodiments, the disorder being treated is a lysosomal storage disease and the conjugate is administered as a pharmaceutical composition in an amount effective to decrease the amount of storage granules present in the brain tissue of said mammal. Typically, the symptoms of such a disorder are monitored through routine assessment of history, physical examination, echocardiography, electrocardiography, magnetic resonance imaging, polysomnography, skeletal survey, range of motion measurements, corneal photographs, and skin biopsy. Administration of a RAP variant conjugated to a therapeutic agent, CR-specific antibody or antibody-conjugate in such a disorder results in normalization of developmental delay and regression in said subject, reduction in high pressure hydrocephalus, reduction in spinal cord compression in said subject, and reduction in number and/or size of perivascular cysts around the brain vessels of said subject. Methods of monitoring and assessing such sequelae are known to those of skill in the art. Those of skill in the art are referred to U.S. Pat. No. 6,585,971; U.S. Pat. No. 6,569,661 and U.S. Pat. No. 6,426,208 and U.S. Patent Publication No. 20040009906 for additional descriptions of such sequelae.

In some aspects, it may be useful to increase the tolerance of the animal to the therapy being delivered. Such methods are described in U.S. patent application Ser. No. 10/429,314 filed May 5, 2003 and published as U.S. Patent Publication No. 20040009906 (incorporated herein by reference in its entirety).

In preferred embodiments, the animal is suffering from mucopolysaccharidosis I and has about 50% or less of a normal α-L-iduronidase activity. In such embodiments, it would be desirable to administered an effective dose of between about 0.001 mg/kg body weight and 0.5 mg/kg body weight of human α-L-iduronidase as part of the conjugate e.g., weekly to a subject suffering from a deficiency thereof. In other embodiments, the subject is given a dose of between about 0.01 mg/15 cc of CSF to about 5.0 mg/15 cc of CSF in the mammal of said human α-L-iduronidase weekly. The therapies contemplated herein promote the breakdown of glycosaminoglycan (GAG) in a brain cell of a subject having lysosomal storage disease. The brain cell may be a neuron, a neuroglial cell, an ependymal cell. Typically, the brain cells in which granule accumulation occurs and should be ameliorated by administering a conjugate of the invention include neurons, glial cells, microglial cells, astrocytes, oligodendroglial cells, perivascular cells, perithelial cells, meningeal cells, ependymal cells, arachnoid granulation cells, arachnoid membranes, dura mater, pia mater and choroid plexus cells. The therapy in preferred embodiments reduces storage granules in meningeal cells as compared to the number of lysosomal storage granules present in a similar cell in the absence of administration of said conjugate. This produces the therapeutic effects of relieving the symptoms of high pressure hydrocephalus in some subjects and said administering reduces the amount of CSF fluid in the meningeal tissue of said subject.

iv. Neurological Disorders

In specific embodiments, the disorder being treated is a neurological disease and the conjugate is administered as a pharmaceutical composition in an amount effective to prevent, manage or treat such neurological disorder. A neurological disorder includes but is not limited to Alzheimer's disease, Parkinson's disease, Multiple Sclerosis, Amylotrophic Lateral Sclerosis, other demyelination related disorders, a central nervous system cancer, traumatic brain injury, spinal cord injury, stroke or cerebral ischemia, plaque sclerosis, cerebral vasculitis, epilepsy, Huntington's disease, Tourette's syndrome, Guillain Barre syndrome, Wilson disease, Pick's disease, neuroinflammatory disorders, encephalitis, encephalomyelitis or meningitis of viral, fungal or bacterial origin, or other central nervous system infections, prion diseases, cerebellar ataxias, cerebellar degeneration, spinocerebellar degeneration syndromes, Friedreichs ataxia, ataxia telangiectasia, spinal damyotrophy, progressive supranuclear palsy, dystonia, muscle spasticity, tremor, retinitis pigmentosa, senile dementia, subcortical dementia, arteriosclerotic dementia, AIDS-associated dementia, or other dementias, striatonigral degeneration, mitochondrial encephalo-myopathies, neuronal ceroid lipofuscinosis, lysosomal storage disorders with central nervous system involvement, leukodystrophies, urea cycle defect disorders, hepatic encephalopathies, renal encephalopathies, metabolic encephalopathies, porphyria, poisonings with neurotoxic compounds, radiation-induced brain damage, or psychiatric disorders such as psychosis, anxiety, depression, attention deficits, memory disorders, cognitive disorders, appetite disorders, obesity, addiction, appetence, or drug dependence.

Alzheimer's Disease

In a preferred embodiment, the disorder being treated is Alzheimer's disease, which is linked to elevated levels of a 40-42 amino acid peptide, amyloid beta (Aβ), within the brains of affected patients (Selkoe, et al. (1996) *J Biol Chem* 271, 18295-18298). Following its generation by a series of sequential proteolytic events, Aβ oligomerizes and ultimately accumulates in insoluble plaques within the neuronal interstitium. Both soluble and insoluble forms of Aβ have been demonstrated to be neurotoxic in vitro and in vivo (Zerbinatti, et al., (2004) *Proc Natl Acad Sci USA* 101, 1075-1080; Tsai, et al., (2004) *Nat Neurosci*; Schmitz, et al. (2004) *Am J Pathol* 164, 1495-1502; Gong, et al. (2003) *Proc Natl Acad Sci USA* 100, 10417-10422; Bard, et al. (2000) *Nat Med* 6, 916-919; Schenk, et al. (1999) *Nature* 400, 173-177; Hsia, et al. (1999) *Proc Natl Acad Sci USA* 96, 3228-3233). Soluble Aβ monomers and oligomers have also been demonstrated to reversibly induce memory deficits by inhibiting long-term potentiation (Gong, et al. (2003) *Proc Natl Acad Sci USA* 100, 10417-10422).

Aβ is a proteolytic fragment of the amyloid precursor protein or APP, a cell surface membrane protein of undetermined function. Aβ formation is initiated within, the neuronal secretory pathway or through endocytosis of APP by LPP1, a member of the LDLR family of receptors (Cam, et al., (2004) *J Biol Chem* 279, 29639-29646). Upon reaching the endosomal system, APP is cleaved by the beta-site APP-cleaving enzyme, or BACE, a membrane protease. BACE cuts APP at position 671, just N-terminal to the transmembrane domain. The remaining portion of APP is then cut a second time by a complex of three proteins, presenilin-1, presenilin-2 and nicastrin, which constitute the gamma-secretase complex (Xia, et al. (2003) *J Cell Sci* 116, 2839-2844). Presenilins cleave their substrates within the inner leaflet of the lipid bilayer. The gamma-secretase cleavage step occurs between positions 711 and 713, within the transmembrane domain of APP. Gamma-secretase cleavage releases Aβ, which is either retained within the neuron or secreted into the extracellular space. In either location, Aβ is toxic to neurons (Casas, et al. (2004) *Am J Pathol* 165, 1289-1300).

The sequential cleavage of APP by beta and gamma-secretases is termed the amyloidogenic pathway. An alternate pathway predominates in the normal brain: The entire ectodomain of APP is released through receptor shedding, a proteolytic process catalyzed by alpha-secretase. The released ectodomain is termed sAPPα and has been demonstrated to have neuroprotective and memory-enhancing effects (Furukawa, et al. (1996) *J Neurochem* 67, 1882-1896; Meziane, et al. (1998) *Proc Natl Acad Sci USA* 95, 12683-12688). APP ectodomain release is the key event in the nonamyloidogenic pathway. Proteolysis in this case occurs at position 688, within the region of APP that becomes Aβ during amyloidogenesis (Allinson, et al. (2003) *J Neurosci Res* 74, 342-352). Therefore, the amyloidogenic and nonamyloidogenic pathways are mutually exclusive. Release of sAPPα is catalyzed by an alpha-secretase, ADAM10, also a membrane-bound protease (Fahrenholz, et al. (2000) *Ann NY Acad Sci* 920, 215-222). ADAM10 is a disintegrin and metalloproteinase, part of a family of "sheddase" enzymes including the Notch cleaving enzyme (Kuzbanian) and the TNF-alpha precursor-cleaving enzyme (TACE, ADAM17). ADAM10 has been found to be responsible for shedding the ectodomain of BACE (Hussain, et al. (2003) *J Biol Chem* 278, 36264-36268).

Like the other members of the ADAM family, ADAM10 has an N-terminal prodomain, a catalytic protease domain, a disintegrin domain, a transmembrane domain and a cytoplasmic tail. The prodomain associates tightly with the catalytic domain, a requirement for proper folding of the enzyme. This association also allows a cysteine in the prodomain to reversibly bind to a zinc atom in the active site, masking the proteolytic activity of the enzyme while it is transiting the secretory pathway. Upon reaching the trans-Golgi, the proprotein convertase furin in the constitutive secretory pathway recognizes residues 211-214 (RKKR) of ADAM10, cleaving off the prodomain and rendering the enzyme proteolytically active.

An increase in Aβ release by beta and gamma-secretases, at the expense of sAPPα release by ADAM10, is believed to be the basis for Alzheimer's disease. A number of programs are underway to develop pharmacological inhibitors of BACE or the gamma-secretase complex, in order to shift APP processing away from amyloidogenic pathway. A complementary approach is to increase sAPPα production at the expense of Aβ by increasing levels of alpha-secretase in the brain interstitium. The imbalance in the proteolytic processing of APP has been corrected in animal models by modestly supplementing the endogenous levels of a particular neuronal protease, ADAM10. The benefits of increased ADAM10 levels in brain have been validated in mouse models of Alzheimer's disease (Postina, et al. (2004) *J Clin Invest* 113, 1456-1464; Lichtenthaler, et al. (2004) *J Clin Invest* 113, 1384-1387). Slight increases in brain ADAM10 levels have been found to prevent the disease phenotype.

The invention contemplates treating Alzheimer's diseases based on intravenous administration of a fusion between RAP, RAP variants or CR-specific antibodies or combinations thereof and ADAM10. A preferred embodiment is a method of treating Alzheimer's Disease comprising administering an ADAM10-RAP or RAP variant fusion or CR-specific antibody and increasing brain alpha-secretase activity, wherein said administering is via intravenous, intracarotid, or intrathecal administration. Increases in alpha-secretase levels, in turn, are expected to divert APP processing away from the amyloidogenic pathway. The enhanced production of sAPPα and its corollary, the diminished production of Aβ, are predicted to have a therapeutic effect on patients suffering from Alzheimer's disease. Alternatively, the invention contemplates treatments for Alzheimer's disease comprising administration of fusions between RAP variants or CR-specific antibodies and other proteases that act on APP or Abeta, or with inhibitors of beta-secretase or with inhibitors of gamma-secretase.

In a related aspect, the invention contemplates minimizing the peripheral effects of an intravenously injected active sheddase enzyme by using ADAM10-RAP fusions or CR-specific antibodies with the prodomain attached. Intact pro-ADAM10-RAP can isolated from standard production lines by co-expression with the furin inhibitor, α1-antitrypsin Portland (Srour, et al. (2003) *FEBS Lett* 554, 275-283; Benjannet, et al. (1997) *J Biol Chem* 272, 26210-26218). Activation of the fusion will then occur by removal of the prodomain after clearance into tissue, either during transcytosis or upon reaching the brain interstitium. During transcytosis, the fusion becomes membrane associated due to association with LRP. The fusion-receptor complex then transits the cell within an endosome. Previous studies in vivo and in vitro have demonstrated partial proteolysis of some proteins in transit during transcytosis (Lisi, et al. (2003) *J Endocrinol Invest* 26, 1105-1110): Endocytosis of ADAM10-RAP or CR-specific antibody either upon initial endocytosis into endothelial cells or on final endocytosis into neurons will expose the fusion to furin in the early endosome (Mayer, et al. (2004) *J Histochem Cytochem* 52, 567-579; Bosshart, et al. (1994) *J Cell Biol* 126, 1157-1172; Rohn, et al. (2000) *J Cell Sci* 113 (Pt 12), 2093-2101). An alternative approach to delayed activation of ADAM10 is replacement of the furin-sensitive peptide linker connecting the prodomain and catalytic domain with an ADAM-sensitive peptide linker. To the extent that the modified prodomain is cleaved in production lines, this reaction can be inhibited by culture in the presence of hydroxamate inhibitors or by co-expression with TIM1 or TIM3 (Amour, et al. (2000) *FEBS Lett* 473, 275-279). While the half-life of RAP fusions in the periphery is short, accumulation of an ADAM-sensitive pro-ADAM10-RAP fusion will result in exposure of the fusion to endogenous, active ADAM10 at the neuron surface within the interstitial space. A proteolytic chain-reaction might then be predicted, with each activated ADAM10-RAP fusion subsequently activating more ADAM10-RAP. Intracarotid co-administration with mannitol, as well as intrathecal administration, may not require inactive ADAM10.

Additional neurological disorders contemplated by the invention are described below. For example, Parkinson's Disease is characterized by tremors and reduced motor neuron function, rigidity, and akinesia. These neurologic signs are due to malfunction of the major efferent projection of the substantia nigra, i.e., the nigrostriatal tract. The cell bodies of neurons in the dopaminergic system are the primary cells involved in PD progression. Examples of primary parkinsonian syndromes include Parkinson's disease (PD), progressive supranuclear palsy (PSP), and striatonigral degeneration (SND), which is included with olivopontocerebellear degeneration (OPCD) and Shy Drager syndrome (SDS) in a syndrome known as multiple system atrophy (MSA).

Amyotrophic lateral sclerosis (ALS), often referred to as "Lou Gehrig's disease," is a progressive neurodegenerative disease that attacks motor neurons in the brain and spinal cord. The progressive degeneration of the motor neurons in ALS eventually leads to their death, reducing the ability of the brain to initiate and control muscle movement.

Huntington's disease (HD), although a genetically heritable disease, results in the degeneration of neurons in the striatal medium spiny GABAergic neurons (Hickey et al., *Prog Neuropsychophamacol Biol Psychiatry.* 27:255-65, 2003). This degeneration causes uncontrolled movements, loss of intellectual faculties, and emotional disturbance.

Multiple Sclerosis (MS) is a frequent and invalidating disease of the young adult. This disease is characterized by an inflammatory reaction, probably of an autoimmune type, and a demyelination frequently associated with a loss of oligodendrocytes, the myelin forming cell in the central nervous system. Current available treatments address the inflammatory factor of MS, but have little, if any, efficacy on remyelination.

The compositions of the invention are useful to treat cancers of the brain. The most common brain tumors are gliomas, which begin in the glial tissue. Astrocytomas, which arise from small, star-shaped cells called astrocytes, most often arise in the adult cerebrum. A grade III astrocytoma is sometimes called anaplastic astrocytoma. A grade IV astrocytoma is usually called glioblastoma multiforme. Brain stem gliomas occur in the lowest, stem-like part of the brain. The brain stem controls many vital functions. Most brain stem gliomas are high-grade astrocytomas. Ependymomas usually develop in the lining of the ventricles. They may also occur in the spinal cord. Oligodendrogliomas arise in the cells that produce myelin, the fatty covering that protects nerves. These tumors usually arise in the cerebrum. They grow slowly and usually do not spread into surrounding brain tissue. Medulloblastomas develop from primitive nerve cells that usually do not remain in the body after birth. For this reason, medulloblastomas are sometimes called primitive neuroectodermal tumors (PNET). Most medulloblastomas arise in the cerebellum; however, they may occur in other areas as well. Meningiomas grow from the meninges. They are usually benign. Because these tumors grow very slowly, the brain may be able to adjust to their presence; meningiomas often grow quite large before they cause symptoms. Schwannomas are benign tumors that begin in Schwann cells, which produce the myelin that protects the acoustic nerve. Acoustic neuromas are a type of schwannoma. Craniopharyngiomas develop in the region of the pituitary gland near the hypothalamus. They are usually benign; however, they are sometimes considered malignant because they can press on or damage the hypothalamus and affect vital functions. Germ cell tumors arise from primitive (developing) sex cells, or germ cells. The most frequent type of germ cell tumor in the brain is the germinoma. Pineal region tumors occur in or around the pineal gland. The tumor can be slow growing pineocytoma or fast growing (pineoblastoma). The pineal region is very difficult to reach, and these tumors often cannot be removed.

Treatment for a brain tumor depends on a number of factors. Among these are the type, location, and size of the tumor, as well as the patient's age and general health. Normally brain tumors are treated with surgery, radiation therapy, and chemotherapy. In one aspect, the invention provides a method of inhibiting growth and progression of neuroblastoma and neural tumors comprising administering to a subject having a neuroblastoma or neuronal tumor a composition comprising a RAP variant or CR-specific antibody of the invention. In additional aspect the RAP variant or CR-specific antibody may be conjugated to an agent useful to treat neural tumors.
GDNF In another preferred embodiment, the invention contemplates a method of treating neurodegenerative disease by administering RAP or RAP variants conjugated to a neuronal growth factor such as glial cell line-derived neurotrophic factor (GDNF). Such neurodegenerative diseases include but are not limited to Parkinson Disease. GDNF was originally purified from a rat glioma cell-line supernatant as a trophic factor for embryonic midbrain dopamine neurons. In vivo, GDNF homodimer binds to its receptor GFRα-1 (probably also a dimer), then the GDNF-GFRα-1 complex binds to the Ret protein, which dimerizes. The dimerization of Ret causes the autophosphorylation of tyrosine 1062. Studies showed that GDNF has pronounced effects on other neuronal subpopulations. Because GDNF protects dopamine neurons in animal models of Parkinson's disease, and rescues motoneurons in vivo, hopes have been raised that GDNF could be used as a therapeutic agent to treat several neurodegenerative diseases. However, GDNF doeg not cross the blood brain barrier. The present invention provides a method of transporting GDNF across the blood brain barrier comprising administering RAP or receptor specific RAP variants conjugated to GDNF.

v. Liver Disorders

LRP1, an LDLR member that binds strongly to RAP, is highly expressed on hepatocytes. One aspect of the invention contemplates conjugation of chemotherapeutic drugs or other agents to RAP or RAP fragments to deliver therapeutic compounds to the liver for the treatment of liver disease. Administration of a RAP conjugate to treat liver disease would solve several problems associated with treatment of liver diseases, such as clearance of the agent by the liver, since a majority of the drug would be delivered directly to hepatocytes almost immediately after injection. Additionally, because the RAP conjugate would be endocytosed via LRP1, drug resistance mechanisms in the plasma membrane (MDR, P-glycoprotein) would be bypassed.

Liver disease contemplated by the invention include, but are not limited to, those disocrders discussed below. Hepatocellular carcinoma, or hepatoma, is the fifth most common cancer in the world and incidence rates have been climbing steadily. Hepatocellular carcinoma is a disease of hepatocytes. Tumorigenic hepatocytes retain high levels of LRPL expression. Hepatocellular carcinoma does not respond well to chemotherapy because the tumor cells show high rates of drug resistance and because the chemotherapies used have serious toxicities, especially in the heart and kidney, due to systemic (intravenous) administration.

Hepatits is a generic term for inflmmatino of the liver. Hepatitis can be acute or chronic and includes acute or chronic liver failure, e.g., due to virus (e.g., hepatitis A, B, C, D or E or non-ABCDE, CMV, Epstein-Barr), fungal, rickettsial or parasitic infections, alcohol, chemical toxins, drugs (e.g. acetaminophen, amiodarone, isoniazid, halothane, chlorpromazine, erythromycin), metabolic liver disease (e.g., Wilson's disease, alpha1-antitrypsin deficiency), cancer, idiopathic autoimmune liver disease, cirrhosis (e.g. primary biliary cirrhosis), biliary obstruction. Infection of the liver by Hepatitis A, B and/or C virus can lead to slowly progressing liver disease leading to liver failure. Acute hepatitis infection is most commonly caused by hepatitis A. Both hepatitis B and hepatitis C infection can persist in the body and become longstanding infections (chronic). Hepatitis C can cause critical conditions including cirrhosis and cancer.

Additional liver disorders or conditions contemplated that are treatable using compositions conjugated to RAP variants or CR-specific antibodies include hepatic steatis (U.S. Pat. No. 6,596,762), cholestasis (U.S. Pat. No. 6,069,167), liver cirrhosis, toxic liver damage, post-hepatectomy conditions, biliary obstruction, Candidate drugs for conjugation to Rap variants or CR-specific antibodies for the treatment of liver disease include, but are not limited to: 5-fluorouracil, doxorubicin (adriamycin), mitomycin C, cisplatin, epirubicin, daunorubicin, etoposide, and other chemotherapeutic agents set out in Table 1, adefovir, lamivudine, entecavir, ribavirin, interferon alpha, pegylated interferon alpha-2a, interferon alpha-2b and other antivirals, Vitamin E, ursodeoxycholic acid, and other agents used to treat liver disorders.

TABLE 1

Alkylating agents
Nitrogen mustards mechlorethamine
cyclophosphamide
ifosfamide
melphalan
chlorambucil
Nitrosoureas carmustine (BCNU)
lomustine (CCNU)
semustine (methyl-CCNU)
Ethylenimine/Methyl-melamine thriethylenemelamine (TEM)
triethylene thiophosphoramide (thiotepa)
hexamethylmelamine (HMM, altretamine)
Alkyl sulfonates busulfan
Triazines dacarbazine (DTIC)
Antimetabolites
Folic Acid analogs methotrexate
Trimetrexate
Pemetrexed (Multi-targeted antifolate)
Pyrimidine analogs 5-fluorouracil
fluorodeoxyuridine
gemcitabine
cytosine arabinoside (AraC, cytarabine)
5-azacytidine
2,2'-difluorodeoxy-cytidine
Purine analogs 6-mercaptopurine
6-thioguanine
azathioprine
2'-deoxycoformycin (pentostatin)
erythrohydroxynonyl-adenine (EHNA)
fludarabine phosphate
2-chlorodeoxyadenosine (cladribine, 2-CdA)
Type I Topoisomerase Inhibitors camptothecin
topotecan
irinotecan
Biological response modifiers G-CSF
GM-CSF
Differentiation Agents retinoic acid derivatives
Hormones and antagonists
Adrenocorticosteroids/antagonists prednisone and equiv-alents
dexamethasone
ainoglutethimide
Progestins hydroxyprogesterone caproate
medroxyprogesterone acetate
megestrol acetate
Estrogens diethylstilbestrol
ethynyl estradiol/equivalents
Antiestrogen tamoxifen

TABLE 1-continued

Androgens testosterone propionate
fluoxymesterone/equivalents
Antiandrogens flutamide
gonadotropin-releasing
hormone analogs
leuprolide
Nonsteroidal antiandrogens flutamide
Natural products
Antimitotic drugs
Taxanes paclitaxel
Vinca alkaloids
vinblastine (VLB)
vincristine
vinorelbine
Taxotere ® (docetaxel)
estramustine
estramustine phosphate
Epipodophylotoxins etoposide
teniposide
Antibiotics actimomycin D
daunomycin (rubido-mycin)
doxorubicin (adria-mycin)
mitoxantroneidarubicin
bleomycin
splicamycin (mithramycin)
mitomycinC
dactinomycin
aphidicolin
Enzymes L-asparaginase
L-arginase
Radiosensitizers metronidazole
misonidazole
desmethylmisonidazole
pimonidazole
etanidazole
nimorazole
RSU 1069
EO9
RB 6145
SR4233
nicotinamide
5-bromodeozyuridine
5-iododeoxyuridine
bromodeoxycytidine
Miscellaneous agents
Platinum coordination complexes cisplatin
Carboplatin
oxaliplatin
Anthracenedione
mitoxantrone
Substituted urea hydroxyurea
Methylhydrazine derivatives N-methylhydrazine (MIH)
procarbazine
Adrenocortical suppressant mitotane (o,p'-DDD)
ainoglutethimide TABLE 1-continued Cytokines interferon (α, β, γ)
interleukin-2
Photosensitizers hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines
zinc phthalocyanines
Radiation X-ray
ultraviolet light
gamma radiation
visible light
infrared radiation
microwave radiation vi. Inhibition by RAP, RAP Domains, RAP Variants, RAP Conjugates CR-Specific Antibodies and Combinations Thereof Tumors In another specific embodiments, the invention contemplates a method of treating diseases comprising administering RAP, RAP domains, RAP variants, RAP conjugates or CR-specific antibodies and combinations thereof with enhanced selectivity for particular CR domains or combinations of CR domains. Overexpression of LRP5, LRP6 and matriptase (MT-ST1, ST14, TADG-15), is associated with increased tumorigenicity of the affected tissue (L1, et al., (2004) Oncogene 23, 9129-9135; Hoang, et al., (2004) Int J Cancer 109, 106-111; Tanimoto, et al., (2005) Br J Cancer 92, 278-283; Santin, et al., (2004) Int J Cancer 112, 14-25; Santin, et al., (2003) Cancer 98, 1898-1904; Tanimoto, et al., (2001) Tumour Biol 22, 104-114). Molecules that bind to these tumorogenic CR-containing proteins may provide a means of diminishing their tumorigenic effects by direct interference with protein functions or by targeting tissues that overexpress these proteins with anti-tumor drugs attached to the selective molecule. Matriptase is anchored in the lateral or basolateral membranes of epithelial cells through an N-terminal type II transmembrane domain (Pfistermueller, et al. (1996) FEBS Lett 396, 14-20). The membrane-embedded sequence is followed by an extracellular SEA domain, two CUB domains, four CR domains and a trypsin domain at the C-terminus of the protein. Mutagenesis of the CR sequences within matriptase results in a failure of the resulting protease mutant to become activated (Qiu, et al. (2003) Neuroscience 122, 291-303). Similarly, an antibody that binds to the third CR domain of matriptase blocks activation of the enzyme (Basu, et al. (2001) Immunity 14, 303-13). A RAP variant or CR-specific antibody with affinity for one of the two CR pairs within matriptase that include the third CR domain would be expected to interfere with proteolytic activation, in a manner similar to the observed inhibition by the antibody to this region. Such a variant would be expected to diminish the metastatic and tumorigenic effects of matriptase overexpression in affected tissues.

Osteoporosis

In a further embodiment, the invention contemplates the treatment of osteoporosis by administering a RAP molecule, RAP variant, RAP conjugate or CR-specific antibody or combination thereof that selectively binds the LDLR associated with maintenance of the bone and inhibits factors that prevent bone growth, development and maintenance. Enhanced Wnt signaling through the LDLR LRP5 is associated with an increase in osteoblast differentiation, inhibition of osteoclast activity and enhancement of bone deposition (Westendorf, et al. (2004) Gene 341, 19-39; Zhang, et al., (2004) Mol Cell Biol 24, 4677-4684; Mizuguchi, et al. (2004) J Hum Genet. 49, 80-86). Such signaling mechanism has been validated with osteoblast-specific APC (adenomatous polyposis coli) knockout mice and with LRP5 mutants that are insensitive to DKK (Dickkopf)-1 and sclerostin-mediated inhibition (Zhang, et al., (2004) Mol Cell Biol 24, 4677-4684; Holmen, et al. (2005) J Biol Chem). The invention contemplates a method of treating osteoporosis or other diseases associated with reduced osteoblast activity and/or increased osteoclast activity by administering molecules that selectively bind LRP5, interfering with inhibitor binding to LRP5, and/or enhancing Wnt signaling through LRP5.

A variety of hosts or subjects are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

EXAMPLES

The following example(s) is included to demonstrate preferred embodiments of the invention. It should be appreciated by those of skill in the art that the techniques disclosed in the example(s) that follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The following examples provide exemplary protocols for generating, isolating and characterizing the interaction of RAP variants with their preferred receptors.

Example 1

Generation and Analysis of RAP Variants

Materials and Methods

Materials—

The M13 phage display vector was from Maxim Biotechnology. Expression vector pET30(+)a and S-tag purification reagents were from EMD Biosciences. Anti-RAP antibodies were produced at BioMarin Pharmaceutical, Inc. Restriction enzymes and T4 DNA ligase were from New England Biolabs. An ABI 3100 Avant automated DNA sequencer was used for sequence data generation and analysis. Hexahistidine tag purification reagents were from Qiagen. The anti-RAP polyclonal antibody was described previously (49).

Expression, Refolding and Purification of CR Proteins—

Others have elegantly demonstrated that CR proteins can be expressed, purified and refolded to their native form in vitro (45, 50-54). For the work described here, the following CR sequences were selected for this process: A CR triplet from LRP6 (CR1-3), the two CR pairs from LRP6 within the triplet (CR1 and 2, termed CR12, CR2 and 3, termed CR23), a CR triplet from human VLDLR (CR6-8), a CR pair from VLDLR (CR78), a CR triplet from LRP2 (CR34-36), two CR pairs from LRP2 (CR89, CR3435), three CR pairs from matriptase/ST14/TADG-15 (CR12, CR23 and CR34), a CR triplet from LRP1 (CR3-5) and the CR pair from FDC-8D6 antigen. DNA fragments encoding each were PCR amplified from human cDNA (BD Biosciences Marathon-Ready™ or from a previously-cloned LRP6 cDNA (9) using HotStart PfuTurbo™ (Stratagene) and the primers:

LRP6CR1F:
(SEQ ID NO: 3)
5'-G C G A T A G G A T C C C C A A C A T G T T C T C C T C A G C A G T T T A C T T G T T T C A C G G G G G A A A T T G A C T G T A T C-3';

LRP6CR2R:
(SEQ ID NO: 4)
5'-G C G A T A A A G C T T T T A T C A A A G C A C T T C A C A G T T C T T C T C A T C T G A T T T G T C C T G G C A G T T T G C A T C T C C A-3';

LRP6CR2F:
(SEQ ID NO: 5)
5'-G C G A T A G G A T C C C C T G T A T G C T C A G A G T C C C A G T T C C A G T G T G C C A G T G G G C A G T G T A T T G A T G G-3';

LPR6CR3R:
(SEQ ID NO: 6)
5'-G C G A T A A A G C T T T T C A C T A A G T C G G A T A A C A A T C C A G T T C A T C T G A C T T G G T C A C T G C A A T C C A C-3';

VLDLRCR6F:
(SEQ ID NO: 7)
5'-G C G A T A G G A T C C C A C A C C A A G T G T C C A G C C A G C G A A A T C C A G T G C G G C T C T G G C G A G T G C-3';

VLDLRCR7F:
(SEQ ID NO: 8)
5'-G C G A T A G G A T C C A C T T G C C G A C C T G A C C A A T T T G A A T G T G A G G A T G G C A G C-3';

VLDLRCR8R:
(SEQ ID NO: 9)
5'-G C G A T A A A G C T T T T A T C A T T C G T T T A T A T G A C A C T C T T T C A G G G G C T C A T C A C T C C A G T C C C T G-3';

LRP2CR8F:
(SEQ ID NO: 10)
5'-G C G A T A G G A T C C C C A C G G A G C A G T G T G G C T T A T T T T C C T T C C C C T G T A A A A A T G G C-3';

LRP2CR9R:
(SEQ ID NO: 11)
5'-G C G A T A A A G C T T T T A T C A T G C G T G G G T G G G G C A G T T G T G C T C A T C A C T G C C A T C C A C A C A G T C G T T G C G T T T G-3';

LRP2CR34F:
(SEQ ID NO: 12)
5'-G C G A T A G G A T C C G A T G G T G C A T A C T G C C A G G C T A C T A T G T T C G A A T G C A A A A C C A T G T T T G T A T C C C G C-3';

LRP2CR35F:
(SEQ ID NO: 13)
5'-G C G A T A G G A T C C G A T G T T C C C T G T A A T T C A C C A A A C C G T T T C C G G T G T G A C A A C A A T C G C T G C-3';

LRP2CR36R:
(SEQ ID NO: 14)
5'-G C G A T A A A G C T T T T A T C A T A T A T T T T C A G C A C A T G T T C T T T C T T T T C C T T T A T T G C A A C C C A G T C A T C G-3';

ST14F1:
(SEQ ID NO: 15)
5'-G C G A T A G G A T C C C C A T G C C C G G G G C A G T T C A C G T G C C G C A C G G G G C G G T G T A T C-3';

ST14F2:
(SEQ ID NO: 16)
5'-G C G A T A G G A T C C T G C G A G G C C G G C C A C C A G T T C A C G T G C A A G A A C A A G T C T G C-3';

ST14F3:
(SEQ ID NO: 17)
5'-G C G A T A G G A T C C A G T T G T C C G G C C C A G A C C T T C A G G T G T T C C A A T G G G A A G T G-3';

ST14R1:
(SEQ ID NO: 18)
5'-G C G A T A A A G C T T T T A T C A A C C C C T G C T C G T C G C T G T T G C T C C G C A G T C G T T C A C A C T G-3';

ST14R2:
(SEQ ID NO: 19)
5'-G C G A T A A A G C T T T T A T C A A C T G C A C C C C T G C T C G T C G C T G T T G-3';

ST14R3:
(SEQ ID NO: 20)
5'-G C G A T A A A G C T T T T A T C A G T C G C A G T C C T T C T C A T C T G A G C C G T C G C T A G A G T C C T C C T T C C C G-3';

-continued

LRP1CR3F:
(SEQ ID NO: 21)
5'-G C G A T A G G A T C C C C C A G T G C C A G C C A G G C G A G T T T G C C-3';

LRP1CR5R:
(SEQ ID NO: 22)
5'-G C G A T A A G C T T T C A A T A G G C A C A C G A A G C A G A C T C A T C A G A G C G G-3'

8D6AF:
(SEQ ID NO: 23)
5'-G C G A T A G G A T C C T C G T G C T G C C A C C C A C C A A G T T C C A G T G C C G C A C C A G T G G C T T A T G-3'

8D6SAR:
(SEQ ID NO: 24)
5'-G C G A T A A A G C T T T T A T C A T C C A C A G C C G A G C T C G T C G C T G G A G T C G G G A C-3'.

Each amplified fragment was sequentially digested with BamHI and HindIII and then ligated into similarly digested pET30(+)a. The resulting plasmids encode proteins consisting of N-terminal hexahistidine and S-peptides fused to the CR fragment. Ligation reactions were transformed into XL-Blue MRF' (Stratagene) by electroporation and plasmids isolated from single colonies. Three mutations, Y1040W, V1047D and R1088D, were introduced into the LRP2 CR89 expression plasmid both singly and in combination using Stratagene QuikChange II XL reagents and the primers:

CR89YWF:
(SEQ ID NO: 25)
5'-G T G C C C A A T T A C T G G C T C T G T G A T G G A G-3';

CR89YWR:
(SEQ ID NO: 26)
5'-C T C C A T C A C A G A G C C A G T A A T T G G G C A C-3';

CR89V1047DF:
(SEQ ID NO: 27)
5'-C T C T G T G A T G G A G A C G A T G A T T G T C A T G A T A-3';

CR89V1047DR:
(SEQ ID NO: 28)
5'-T A T C A T G A C A A T C A T C G T C T C C A T C A C A G A G-3';

CR89R1088DF:
(SEQ ID NO: 29)
5'-C A C A C T G G C G C T G T G A C A A A G A C A A C G A C T G T G T G G A T G G C-3';

CR89R1088DR:
(SEQ ID NO: 30)
5'-G C C A T C C A C A C A G T C G T T G T C T T T G T C A C A G C G C C A G T G T G-3'.

All expression constructs were sequenced to verify insert sequences and the junctions with the expression vector. Each plasmid was then used to transform BL21(DE3) CodonPlus-RIPL™ cells (Stratagene). Expression of the CR proteins was induced in logarithmic growth-phase cells grown in LB supplemented with 34 µg/mL chloramphenicol, 12.5 µg/mL tetracycline and 15 µg/mL kanamycin by addition of 2 mM IPTG, followed by reduction in incubator temperature to 32° C. and incubation for 4 hours with agitation at 250×g. Cells were pelleted and resuspended, at 3.5% of the initial culture volume in 10 mM Tris-HCl pH 8, 100 mM $NaH_2PO_4$, 8M Urea. Resuspended cells were then frozen in liquid nitrogen, rapidly thawed to 37° C. and sonicated for 10 seconds at an amplitude setting of 60 using a Cole-Parmer CP-130 ultrasonic processor connected to a 3 mm probe. This procedure was repeated three times to effect complete lysis of the cells. Lysates were clarified by spinning twice at 10,000×g in a Sorvall RC-5 centrifuge for 20 minutes at 15° C. Ni-NTA columns (Qiagen Superflow™, 1.5 mL packed bed) were used to purify the CR proteins. Briefly, the resin was equilibrated with two column volumes of lysis buffer. The clarified lysate was then supplemented to 20 mM with imidazole and incubated with the equilibrated Ni-NTA resin overnight at 4° C. The flow-through was discarded. Columns were washed once with one column volume of lysis buffer and then three times with one column volume of TBS pH 8 supplemented with 20 mM imidazole. CR-loaded beads were then removed from the column and CR proteins eluted by incubating at room temperature for 30 minutes with one column volume of the same buffer containing 200 mM imidazole. This step was repeated once and the eluates pooled. Eluted CR protein solutions were then supplemented to 2 M urea, 10 mM $CaCl_2$ and 5 mM DTT. Purified, denatured CR protein solutions were transferred to 3,500 MWCO Slide-A-Lyzer™ (Pierce) cassettes and sequentially dialyzed against a 200-fold excess of 50 mM Tris-HCl pH 8.5, 10 mM $CaCl_2$, 1 mM reduced glutathione, 0.5 mM oxidized glutathione at room temperature overnight and then against TBS supplemented with 5 mM $CaCl_2$ at 4° C. overnight. Protein concentrations were determined by Bradford assay and purity confirmed by SDS-PAGE with Coomassie Brilliant Blue staining.

Preparation of a RAP Phage Display Library—

The phage display phagemid pHage 3.2 was modified to remove PflMI and HindIII sites within the pIII leader sequence using QuikChange II™ reagents (Stratagene). In addition, the polylinker of pHage 3.2 was modified by ligation to a double-stranded linker containing BamHI, NotI and AgeI sites. The resulting modified phagemid was called phage 3.6. A previously described vector for expression of a fusion between RAP and human □-L-iduronidase, pc3B-RAPIDU (49), was digested with BamHI and AgeI to obtain a DNA fragment encoding the human RAP sequence. This sequence begins at nucleotide 102 of the RAP cDNA and ends at nucleotide 1059. The encoded RAP protein lacks both the RAP signal peptide at the N-terminus and the HNEL endoplasmic reticulum retention signal at the C-terminus. In addition, there is an in-frame BamHI site at the 5'-end and an in-frame sequence encoding the peptide AEAETG, including an AgeI site, at the 3'-end. The RAP sequence was ligated into similarly digested pHage 3.6, creating a fusion between the M13 pIII leader peptide, the RAP sequence and the pIII sequence. This construct was termed pHage 3.6 RAP. Next, two positions within the third domain of RAP (RAP d3 K256 and K270) that had been previously reported to be important for receptor binding were mutagenized (55). These two positions were saturated by separate PCR amplification of the 5' and 3'-halves of RAP d3 using pairs of normal and mutagenic primers:

RAP2KXF:
(SEQ ID NO: 31)
5'-C C C T C G G A C G T C A G C G A C A T C A A G G G C A G C G T C C T G-3';

RAP2KX2:
(SEQ ID NO: 32)
5'-C T C C A G C T G C T T C T G G T A G T G G T T G T G V N N C T C C T C G A T T T T G G C T T C G A A G T G C T T G A G CT C C T-3';

RAP2KX1:
(SEQ ID NO: 33)
5'-A A G C A G C T G G A G A T T G C G C A C G A G N N B C T G A G G C A C G C A G A G A G C G T G G G C G A A C G G C-3';
and RAPmut1R:
(SEQ ID NO: 34)
5'-G G T G C G G G G C C T C A C C G G T-3').

The fragments were amplified from pc3B-RAPIDU. Each mutagenic primer replaces one of the selected lysine codons with one of 47 other codons or with one of the three possible stop codons. This substitution creates a pool of 2304 possible combinations of nucleotides and 441 possible combinations of amino acids (or termination codons). Both the RAP d3 5' and RAP d3 3'-PCR fragments were digested with PvuII at a common site and then combined in a ligation reaction with T4 DNA ligase. A heterodimeric ligation product consisting of the 5' and 3'-fragments fused at the PvuII site was resolved on FMC NuSieve GTG™ agarose gels and purified using Amersham GFX™ reagents. The heterodimer was quantified by UV spectroscopy and subjected to further rounds of mutagenesis by error-prone PCR using the GeneMorph II EZ Clone™ reagents (Stratagene) and the primers RAPKXF and RAPmut1R (described above). The heterodimer concentration was kept below 400 pg for each 50 µL reaction to maximize the final mutation frequency. Mutagenized DNA was digested with AgeI, purified by GFX, quantified by UV spectroscopy and used for ligase-free cloning into pHage 3.6 RAP using Stratagene EZclone™ reagents. Ligase-free cloning reaction products were purified using Qiagen MinElute™ columns. Aliquots of the purified ligase-free cloning products (3 µL) were used to transform 50 µL aliquots of XL10-Gold™ chemically-competent cells. Aliquots of the transformed cells were serially-diluted and plated on LB plates containing 100 µg/mL carbenicillin to determine the number of primary transformants. The remaining transformed cells were plated on Nunclon 25×25 cm dishes. A total of 119,500 primary transformant colonies were recovered from the dishes with the aid of 350 mL of Qiagen GigaPrep™ P1 buffer. Plasmid DNA was prepared using Qiagen reagents and protocols. The plasmid preparation was quantified and digested with BamHI and AgeI to confirm the presence of appropriately-sized insert.

Preparation of a RAP d3 Mutant Library—

A RAP d3 mutant library was prepared by PCR using PfuUltra enzyme and reagents (Stratagene). The 5' and 3' halves of the d3 coding sequence were separately amplified using HPLC-purified primers MORPHF4:
(SEQ ID NO: 35)
5'-G G C C C A G A T C T A C C G G T T T C T G C C T C G G C-3';

D3HALFR2:
(SEQ ID NO: 36)
5'-G T G C G C A A T C T C G A G C T G C T T C T G G T A G T G G T T G T G V N N C T C G A T T T T G G C V N N G A A G T G C T T G A G C T C C T C C C G G-3';

D3HALFF2:
(SEQ ID NO: 37)
5'-C C A C T A C C A G A A G C A G C T C G A G A T T G C G C A C G A G N N B C T G A G G C A C G C A G A G A G C G T G G G C G A C G G C-3';

MORPHR3:
(SEQ ID NO: 38)
5'-G A G T G C G G C C G C A A G C T T A T C T T C T G C C T C G G C-3'.

The primers replace codons at positions 251, 256 and 270 with NNB, resulting all possible amino acids at these positions. In addition, a PvuII site within the RAP d3 coding sequence was ablated with a single, silent, base substitution. Amplified fragments were purified using Amersham GFX reagents and then assembled by primer-less PCR using PfuUltra. The assembled pool of RAP d3 variants sequences was then quantified and subject to mutagenesis using GeneMorph II reagents (Stratagene). Mutagenized DNA was sequentially digested with BamHI, PvuII and AgeI with purification using GFX reagents after each reaction. The digested RAP d3 variant fragment pool was then ligated into similarly digested pHage 3.6 (see above). A plasmid library was prepared by transformation of XL10-Gold cells (Stratagene) and plating on 25×25 cm dishes of LB supplemented with carbenicillin. Colonies were recovered from the dishes and plasmid DNA prepared as above.

Preparation of Phage—

Plasmid libraries (10 ng) were used to transform XL-Blue MRF' by electroporation. Following incubation for 1 hour at 37° C. in 1 mL of 2×YT supplemented with 2% glucose, cultures of transformed cells were supplemented to 100 µg/mL with carbenicillin and grown an additional 6 hours. Following this interval the 1 mL culture was used to innoculate 10 mL of 2×YT supplemented with 2% glucose, 100 µg/mL carbenicillin and $10^8$ pfu/mL M13K07 helper phage (New England Biolabs) in a 50 mL Erlenmeyer flask. This culture was shaken at 250×g for 2 hours at 37° C., and then centrifuged in a Sorvall RC-5 centrifuge at 2,000×g for 10 minutes to pellet the cells. Cells were resuspended in 10 ml 2×YT with 100 µg/ml carbenicillin and 100 µg/ml kanamycin and shaken overnight at 37° C. Cultures were clarified by centrifugation twice at 10,000×g and supernatants collected. Phage were precipitated by combining the supernatant with one volume of cold TBS and 0.2 volumes of 2% PEG 8000 (Sigma), 2.5 M NaCl, collected by centrifugation at 10,000×g and resuspended in TBS. Phage titer was determined by serially-diluting phage samples, incubating with logarithmic phase XL-Blue MRF' and plating on 2×YT agar supplemented with 100 µg/mL carbenicillin.

Phage Panning—

Purified, folded CR proteins were used to coat Nunc MaxiSorp™ 96-well plates at 1 μg/well overnight at 4° C. in TBS supplemented with 5 mM CaCl$_2$. Wells were rinsed and blocked with TBS Superblock™ (Pierce) supplemented with 5 mM CaCl$_2$ prior to addition of phage. Purified phage libraries of 10$^9$ cfu (10$^{10}$ cfu/mL) in TBS Superblock™ supplemented with 5 mM CaCl$_2$ and 0.05% Tween-20 were added to coated wells and incubated for 2 hours at room temperature. Wells were then washed fifteen times with TBSTC (20 mM Tris-HCl pH 7.4, 150 mM NaCl supplemented with 5 mM CaCl$_2$ and 0.05% Tween-20). Bound phage were eluted in 0.2 M glycine-HCl pH 2.2 with 1 mg/ml BSA and transferred to tubes containing 0.2 volumes of 1M Tris-HCl pH 9.1 to bring the pH to neutrality. Eluted phage were recovered by mixing eluate with log-phase XL-Blue MRF' cells. Rescued phage were amplified by growing cells in liquid culture at 30° C. overnight (16 hours). In addition, aliquots of transformed cells were titered by serially diluting the samples and plating on 2×YT agar containing 100 μg/mL carbenicillin. Phage were purified and concentrated from media supernatants by PEG precipitation.

Expression of RAP d3 Proteins—

RAP d3 sequences were PCR amplified using d3RescueF: 5'-GCGATAGGATCCCTGGACCGCCTGCGCAG GGT-CAGCCACC-3' (SEQ ID NO: 39) and d3Rescue R: 5'-GC-GATAA AGCTTTTATCAAGATCTACCGGTTTCT-GCCTCGGC-3' (SEQ ID NO: 40), digested with BamHI and HindIII and ligated into similarly digested pET30(+)a. RAP d3 proteins were expressed in BL21(DE3) CodonPlus-RIPL™ and purified by Ni-NTA chromatography as described above. Protein concentrations were measured by Bradford assay and purity was assessed by SDS-PAGE.

Sequential Reversion of Mutant RAP d3 and Forward Mutation of Wild-Type RAP d3—

Each mutation within the affinity-selected RAP d3 variant was individually reverted to wild-type using Stratagene QuickChange II XL™ reagents and primers V2AR1:
(SEQ ID NO: 41)
5'-A G G G T C A G C C A C C A G G G C T A C A G C A C T G A G G C T A A G T T C G A G G A G C C C A G G G TG A T-3';

V2AR2:
(SEQ ID NO: 42)
5'-C A G C C A C C A G G G C T A C A C C A C T G A G G C T G A G T T C G A G G A G C C C A G G G T G A T T G A C C-3';

V2AR3:
(SEQ ID NO: 43)
5'-G G A G G C G T T C C G G G A G G A G C T C A A G C A C T T C A A A G C C A A A A T T G A G G C C C A C A A C C-3';

V2AR4:
(SEQ ID NO: 44)
5'-C G T T C C G G G A G G A G C T C A A G T A C T T C G A A G C C A A A A T T G A G G C C C A C A A C C A C T A C-3';

V2AR5:
(SEQ ID NO: 45)
5'-G C T C A A G T A C T T C A A A G C C A A A A T T G A G A A G C A C A A C C A C T A C C A G A A G C A G C T G G A G-3';

V2AR6:
(SEQ ID NO: 46)
5'-A G A A G C A G C T G G A G A T T G C G C A C G A G A A G C T G A G G C A C G C A G A G A G C G T G G G C G A C G G-3';

V2ARR1:
(SEQ ID NO: 47)
5'-A T C A C C C T G G G C T C C T C G A A C T T A G C C T C A G T G C T G T A G C C C T G G T G G C T G C C C T-3';

V2ARR2:
(SEQ ID NO: 48)
5'-G G T C A A T C A C C C T G G G C T C C T C G A A C T C A G C C T C A G T G G T G T A G C C C T G G T G G C T G-3';

V2ARR3:
(SEQ ID NO: 49)
5'-G G T T G T G G G C C T C A A T T T T G G C T T T G A A G T G C T T G A G C T C C T C C C G G A A C G C C T C C-3';

V2ARR4:
(SEQ ID NO: 50)
5'-G T A G T G G T T G T G G G C C T C A A T T T T G G C T T C G A A G T A C T T G A G C T C C T C C G G A A C G-3';

V2ARR5:
(SEQ ID NO: 51)
5'-C T C C A G C T G C T T C T G G T A G T G G T T G T G C T T C T C A A T T T T G G C T T T G A A G T A C T T G A G C-3';

V2ARR6:
(SEQ ID NO: 52)
5'-C C G T C G C C C A C G C T C T C T G C G T G C C T C A G C T T C T C G T G C G C A A T C T C C A G C T G C T T C T-3'.

Wild-type RAP d3 was mutagenized using the same method and the following primers:

K256AF:
(SEQ ID NO: 53)
5'-C T T C G A A G C C A A A A T C G A G G C G C A C A A C C A C T A C C A G A A G C-3';

K256AR:
(SEQ ID NO: 54)
5'-G C T T C T G G T A G T G G T T G T G C G C C T C G A T T T T G G C T T C G A A G-3';

-continued

K270EF:
(SEQ ID NO: 55)
5'-G C T G G A G A T T G C G C A C G A G G A G C T G A G G C A C G C A G A G A G-3';

K270ER:
(SEQ ID NO: 56)
5'-C T C T C T G C G T G C C T C A G C T C C T C G T G C G C A A T C T C C A G C-3';

d3E251KF:
(SEQ ID NO: 57)
5'-G A G G A G C T C A A G C A C T T C A A A G C C A A A A T C G A G A A G C A C A A C-3';

d3E251KR:
(SEQ ID NO: 58)
5'-G T T G T G C T T C T C G A T T T T G G C T T T G A A G T G C T T G A G C T C C T C-3';

d3E217KF:
(SEQ ID NO: 59)
5'-C A G G G C T A C A G C A C T G A G G C T A A G T T C G A G G A G C C C A G G G T G-3';

d3E217KR:
(SEQ ID NO: 60)
5'-C A C C C T G G G C T C C T C G A A C T T A G C C T C A G T G C T G T A G C C C T G-3';

d3H249YF:
(SEQ ID NO: 61)
5'-G T T C C G G G A G G A G C T C A A G T A C T T C G A A G C C A A A A T C G A G-3';

d3H249YR:
(SEQ ID NO: 62)
5'-C T C G A T T T T G G C T T C G A A G T A C T T G A G C T C C T C C C G G A A C-3'.

Solid Phase Binding Assays—

Purified, refolded CR protein (1 µg) was bound to Nunc Maxisorp™ 96-well plates in TBS pH 8 supplemented with 5 mM $CaCl_2$ (TBSC) overnight at 4° C. Wells were washed with TBSC and then blocked with TBSC containing 2% bovine serum albumin (BSA). RAP ligands were then incubated with the immobilized receptor at a range of concentrations for 2 hours in the above blocking buffer supplemented with 0.05% Tween-20 at room temperature. Control wells contained no added ligand. As an additional control, to determine whether the absence of calcium affected binding, 10 mM EGTA was included in the incubation medium for some samples. Wells were washed with TBSTC and bound ligands detected with polyclonal anti-RAP (BP41/42, 1:1,000, BioMarin). Excess primary antibody was removed and wells washed before incubation with the secondary antibody, HRP-conjugated goat anti rabbit IgG (Bio-Rad). After washing, TMB substrate solutions (Bio-Rad) were added to detect HRP. Color development was stopped with 1N HCl. Absorption at 450 nm was measured with a microplate spectrophotometer (Molecular Devices). Data were plotted and Kd values derived by non-linear regression with the assumption of single-site binding (GraphPad Prism).

Results

In order to identify tandem CR pairs within the human proteome and to analyze those positions within the pairs that had previously been implicated in binding to RAP, sequences of 190 non-redundant human CR sequences identified in the Pfam database (pfam.wustl.edu) were transferred to a spreadsheet. Tandem pairs of CR sequences were then identified, with the only requirement for assignment as a pair being that the two CR sequences be immediately adjacent to each other within the primary sequence of the protein in which they were found. Imposition of a 75 amino acid limit on the distance between the first amino acids of each CR sequence, as defined in the Pfam database, adequately tested for this condition. The assumption of the requirement for a tandem arrangement was made since the preponderance of historical data on the binding of RAP to defined CR sequences involves such pairs. Overlapping pairs were included such that a linear array of three CR sequences comprised two CR pairs. There were 149 tandem CR pairs identified in this way. Sequence conservation in the area of the calcium-binding loop facilitated the next step in the analysis, extraction of four amino acids tied directly to RAP binding in previous studies (56, 57). These are equivalent to A and C from the AxcBxCxD motif of each CR sequence of a CR pair. The amino acid identities at positions A and C from the first CR sequence of each pair, along with the amino acids at positions A and C from the second CR sequence of each pair (henceforth, A' and C') were then concatamerized into a single, tetrameric text string (ACA'C') for the purposes of comparison. The text strings for each CR pair were compared to those for all other CR pairs and the frequency of each counted. Of the 149 non-redundant human tandem CR pair sequences that were identified in this analysis, the most common combination of amino acids at A, C, A' and C' was WDWD, which was found 16 times. In addition, there were a total of four CR pairs with the WEWD signature, two with WEWE and six with WDWE, for a total of 28 fitting our definition of canonical CR pairs. The canonical CR pair signatures were found only in the LDLR family, specifically in VLDLR, LRP1, LRP1B, LRP2, LRP4, apoER2 and sortilin. All of these receptors have been previously shown to bind RAP with high affinity. In addition to redundant combinations of lower frequency, 101 unique combinations were identified, with all CR pair-containing proteins having at least one. Each tetrameric combination of amino acids at A, C, A' and C' was then generalized by assigning amino acids to one of six groups based on the approximate physico-chemical properties of their side-chains. Hydrophobic aliphatic amino acids were assigned to group 1 (I, L, M, V), small, hydrophilic amino acids to group 2 (A, C, G, P, S, T), basic amino acids to group 3 (H, K, R), acidic amino acids to group 4 (D, E), carboxamide amino acids to group 5 (N, Q) and aromatic amino acids to group 6 (F, W, Y). As before, each generalized combination was then compared to all other such combinations and their frequencies counted. The most common generalized combination was found to be 6464, with aromatic amino acids at A and A' and acidic amino acids at C and C'. This group included all 28 of the specific canonical combinations, and accounted for 44 of the 149 CR pair combinations. Representatives of this class of CR pairs were found in ten proteins, including two outside of the LDLR family, corin and perlecan. A total of 57 of the generalized combinations were unique and, as before, at least one unique combination could be found in each LDLR receptor ectodomain, except for the VLDLR. Other proteins containing CR pairs with unique generalized combinations of amino acids at the selected positions included the transmembrane serine protease matriptases 1, 2 and 3 (MT-SP1, ST14, TADG-15), FDC-8D6 antigen, corin, complement factor I and the heparin sulfate proteoglycan protein, perlecan (25, 58).

From the large number of CR pairs with unique combinations of amino acids at A, C, A' and C' within the calciumbinding loop of each CR, CR pairs or triplets were selected to test their binding to RAP d3 (FIG. 2). An additional pair derived from the FDC-8D6 protein was tested, designated 8D6 CR12, having the sequence (GSSCPPTKFQCRTS-GLCVPLTWRCDRDLDCSDGSDEEE-CRIEPCTQKGQCPP PPGLPCPCTGVSDCSGGTDKKL-RNCSRLACLAGELRCTLSDDCIPLTWRCDGH PDCPDSSDELGCG) (SEQ ID NO: 91). The selected receptor fragments comprise single pairs or two overlapping pairs (triplets) of CR sequences and were meant to reflect the range of amino acid combinations at the selected positions. Taking into account that overlapping pairs might fold less efficiently than isolated pairs, one or both overlapping pairs making up each triplet were also expressed in some cases. Sequences included an LRP6 CR triplet, equivalent to amino acids 1247-1363 of full-length human LRP6 (Uniprot accession O75581), termed LRP6 CR1-3; both overlapping CR pairs comprising the LRP6 triplet, LRP6 CR12 and LRP6 CR23, amino acids 1247-1322 and 1323-1363; a fragment of the VLDLR, amino acids 235-358 (Uniprot accession P98155), termed VLDLR CR6-8; a CR pair within the VLDLR triplet, termed VLDLR CR78, containing amino acids 295-358; three CR pairs from the transmembrane serine protease matriptase, termed MAT CR12 (ST14 CR12), amino acids 452-524, MAT CR23 (ST14 CR23), amino acids 487-566 (Uniprot accession Q8WVC1) and MAT CR34 (ST14 CR34), amino acids 525-602; the CR pair from FDC-8D6 antigen, amino acids 53-168 (Uniprot accession Q9NPF1) and, a triplet from LRP1, termed LRP1 CR3-5, comprising amino acids 852-973 (Uniprot accession P98157). LRP1 CR3-5 consists of two, overlapping canonical CR pairs with the WDWD signature, each of which has previously been demonstrated to bind to RAP d3 with high-affinity (56).

A number of previous studies have demonstrated that CR pairs and triplets can be expressed in bacteria and refolded in vitro into native structures (45, 50-54, 56, 57, 59-62). Each purified, refolded CR protein was expressed and analyzed by SDS-PAGE under both reducing and non-reducing conditions (FIG. 3). CR mobility was consistent with predicted molecular weight under reducing conditions, and each protein was judged to be >90% pure. Under non-reducing conditions, each CR protein migrated through the gel more quickly than expected for the predicted molecular weight. This observation is consistent with a compact folded structure dependent on intramolecular disulfide bond formation. While a number of possible disulfide bond combinations are possible, the studies cited above demonstrate that the native disulfide-bonding pattern is favored during refolding, especially in the presence of calcium. In most cases, and taking into account the relatively low resolution of the electrophoretic analysis, the folded form of the CR protein appeared to be a single band (FIG. 3).

The binding of wild-type RAP d3 to each CR pair or set of overlapping pairs was then measured by solid-phase assay (FIG. 4). The apparent Kd for binding of RAP d3 to LRP1 CR3-5 in this assay was 11 nM, in the same range as values previously reported (56, 57, 63). RAP d3 binding to LRP6 CR12, LRP6 CR23, LRP6 CR1-3, VLDLR CR78, LRP2 CR3536, LRP2 CR34-36 and MAT CR23 was less than 5% of that for LRP1 CR3-5 at the highest ligand concentrations tested. Binding of RAP d3 to MAT CR12 and CR34, measured in a separate set of experiments, was also undetectable. RAP d3 binding to VLDLR CR6-8 and LRP2 CR89 was slightly higher, allowing curves to be reliably fitted to the binding isotherms. Nevertheless, apparent dissociation constants for binding of RAP d3 to these receptor fragments were over 300 nM.

Having established that RAP d3 does not bind to CR pairs containing unique combinations of amino acids within the calcium-binding loop, an affinity-selection system for mutants of RAP d3 that are able to bind such pairs was developed. Fusions of RAP to other proteins have been expressed in both mammalian and bacterial cells and have been demonstrated to retain the receptor-binding behavior of native RAP (49, 64, 65). Therefore, libraries of full-length RAP fused N-terminally to the M13 pIII structural protein were created, as has been previously done with other proteins (66). To create a pool of RAP mutants, two mutagenic procedures were applied to the third domain within the full-length RAP coding sequence. The codons for two positions previously demonstrated to participate directly in receptor binding, K256 and K270, were first subjected to saturation mutagenesis. Additional mutations were then randomly introduced into RAP d3 using-error-prone PCR. Following these procedures, a total of 38 randomly-selected clones were sequenced to determine the mutation frequency. Ten clones (26%) had base insertions, deletions or substitutions that resulted in stop codons within the RAP sequence. Recombinant phage encoding such sequences will be favored during the processes of phage assembly and infection since only wild-type pIII becomes incorporated into the phage capsid. An additional four clones (11%) were found to encode wild-type RAP. The remaining 24 clones (63%) of the RAP phage-pIII fusions encoded RAP proteins with mutations in d3. None of these clones had the same combination of amino acids at positions 256 and 270, indicating that a range of substitutions had occurred as expected at these sites. The average mutation frequency exclusive of positions 256 and 270 was 2.4 amino acid substitutions within the last 110 amino acids of RAP (RAP d3). One of the 38 clones had an in-frame deletion of 7 codons while another had an in-frame insertion of unidentified sequence partly replacing the 3'-end of RAP d3. No mutations were found within d1 or d2 of RAP.

A second phage display library was prepared encoding only RAP d3. This library was generated in a similar fashion to the full-length RAP library, except that an additional position, 251, was subjected to saturation mutagenesis based the apparent importance of this site in a variant from an earlier screen (see below). Apart from positions 251, 256 and 270, the RAP d3 mutant library had an average mutation frequency of 2 amino acid substitutions within the last 110 amino acids of RAP. There was no apparent over-representation of wild-type RAP sequences in this library.

To test whether the phage panning system could be used to isolate RAP sequences based on affinity, a preparation of phage expressing wild-type RAP was diluted one thousand-fold into a preparation of phage expressing a mutant. RAP (K256D, K270D) that was expected to have diminished CR pair-binding ability (55). Panning was performed as described in Methods. Recovered phage were amplified and titered. The RAP d3 sequence from ten recovered colonies was sequenced. After a single round of panning, two of the ten colonies from the panning experiment contained wild-type RAP, an enrichment of 200-fold from the starting pool. As an additional test of the system using a more complex pool of sequences, RAP phage libraries in which positions 256 and 270 had been randomized were panned on LRP1 CR3-5. In the initial phage library, the wild-type RAP sequence was encoded by approximately one of 10 phage (based on sequencing of random clones prior to selection). Following the first round of panning, the wild-type RAP sequence was encoded by 7 of 10 phage. This result demonstrates a 7-fold enrichment for the selected sequence from a complex pool of sequences after one round of panning.

Concluding that RAP sequences could be isolated from phage display libraries by affinity selection, we first chose a CR pair that was not bound by wild-type RAP, LRP2 CR89, and used it as a paining substrate with the doubly-mutagenized full-length RAP phage library. After four rounds of panning, three of eight randomly chosen clones were identical. The common sequence had seven mutations: V175L, S213T, E217K, H249Y, E251K, K256A, K270E. A second group of four clones had identical substitutions at positions 256 and 270 (K256A, K270R), but had variable substitution patterns outside of these two sites. After a fifth round of panning, seven of eight randomly chosen clones had the previously-observed V175L, S213T, E217K, H249Y, E251K, K256A, K270E mutation set. All mutations for this sequence, termed RAPv2A or MegaRAP1 were in the region specifically mutagenized to make the variant library.

To confirm that library resolution had occurred as a result of affinity selection, RAP and MegaRAP1 phage were prepared and assayed for binding to LRP2 CR89. With identical starting titers, 2.6-fold more colony forming units (cfu) were recovered by panning with MegaRAP1 phage than with wild-type RAP phage. Similar results were obtained when bound phage were detected with an anti-pIII antibody, indicating that differences in infectivity between the two phage were not responsible for differences in the titers of recovered phage. By conducting the binding reaction in the presence of 50 mM EDTA, MegaRAP1 binding was determined to be dependent on calcium, consistent with the requirement for an ordered CR fold as the receptor. Since both RAP and MegaRAP1 phage had identical d1 sequences and d2 sequences that differed by a single, conservative substitution (V175L), we hypothesized that differences in d3 were responsible for improvements in binding to LRP2 CR89. Accordingly, RAP d3 and MegaRAP1 d3 were subcloned and expressed for subsequent binding analyses. Since the d3 regions expressed for further study comprised amino acids 201-319 of mature RAP, the effect of the V175L mutation on the binding behavior of RAPv2A was not determined.

Figure 4:
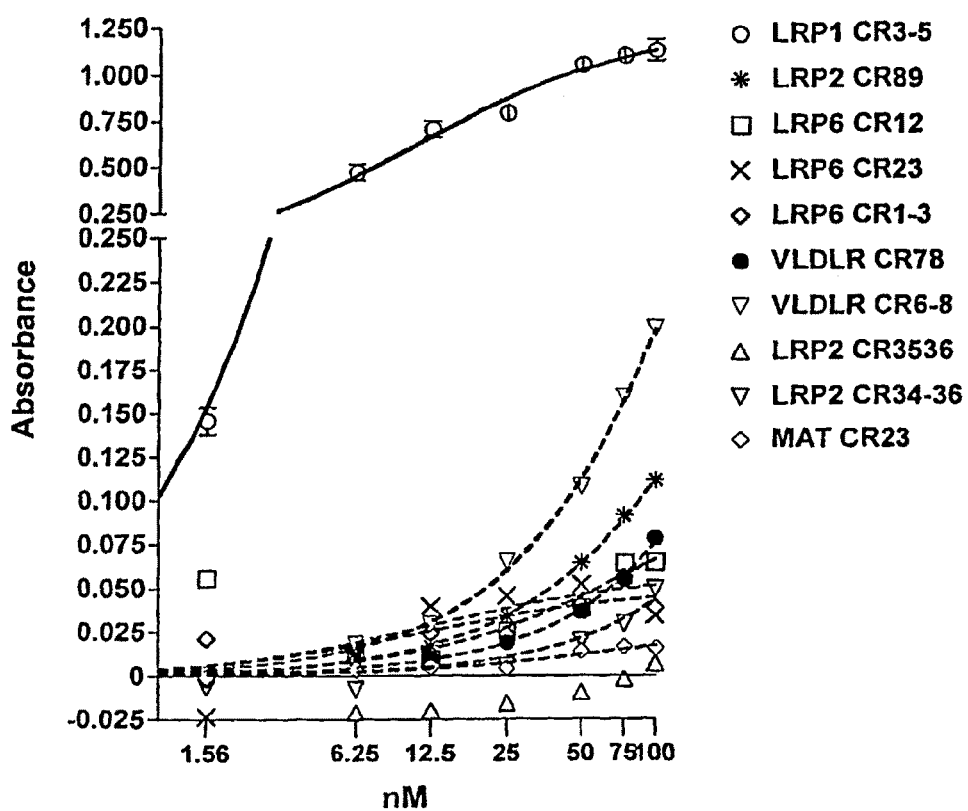
FIG. 4 depicts binding of RAP d3 to selected CR proteins using a dilution series of RAP d3 was prepared from 100-1.25 nM.

Next, the binding of RAP d3 and MegaRAP1 d3 proteins to LRP1 CR3-5 and LRP2 CR89 was assessed. In order to understand the relative contributions of each MegaRAP1 d3 mutation to differences in affinity, we also prepared a number of MegaRAP1 d3 revertants and RAP d3 forward mutants, all comprising sequence variants intermediate between MegaRAP1 d3 and wild-type RAP d3 (FIGS. 5A and 5B, FIG. 16). In all cases, 10 mM EGTA prevented binding of both RAP d3 and MegaRAP1 d3 to CR proteins. Since calcium was the only divalent metal ion present in the binding buffer, this observation is consistent with both RAP d3 and MegaRAP1 d3 binding to calcium-loaded CR pairs. RAP d3 bound LRP1 CR3-5 with a dissociation constant of 16 nM and showed no significant affinity for LRP2 CR89, consistent with the data represented in FIG. 4. Conversely, MegaRAP1 d3 bound LRP2 CR89 with an apparent dissociation constant of 38 nM but with no significant affinity for LRP1 CR3-5. Therefore, wild-type RAP d3 and MegaRAP1 d3 have inverted binding preferences for these two receptor fragments. Two MegaRAP1 d3 revertants, T213S and K217E had slightly improved affinities for LRP2 CR89 and remained unable to detectably bind LRP1 CR3-5. Three MegaRAP1 d3 revertants, Y249H, K251E and A256K, failed to bind either receptor fragment, indicating that the mutations were important for the interaction between MegaRAP1 d3 and LRP2 CR89 and were not individually responsible for disrupting binding to LRP1 CR3-5. Interestingly, the E270K revertant bound both receptor fragments with higher affinity than MegaRAP1 d3, giving apparent dissociation constants of 8 nM for LRP2 CR89 and 142 nM for LRP1 CR3-5. Since the MegaRAP1 d3 mutant was selected based on affinity for LRP2 CR89, this result is consistent with the diversity of the starting library being insufficient to account for all possible sequence variants. Alternatively, the affinity differences between MegaRAP1 d3 and MegaRAP1 d3 E270K may have been insufficient to allow the latter to predominate upon iterative panning. A double revertant, T213S, E270K, had binding behavior that was not distinguishable from MegaRAP1 d3 in our assays. Since the two single-site revertants at these positions appeared to show improved affinity for LRP2 CR89, and in the case of E270K, LRP1 CR3-5 also, this result indicates a lack of additivity for binding effects resulting from these reversions or a lack of accuracy within this affinity range in our assays. The binding behavior of the K251E, E270K double revertant implies a strong dependence of the affinity of MegaRAP1 d3 for LRP2 CR89 on the E251K mutation. The difference in LRP2 CR89 affinity between this revertant and the single-site E270K revertant is almost 20-fold. The A256K, E270K double revertant results in a 2-fold loss of affinity for LRP2 CR89, implying a moderately positive effect that the K256A MegaRAP1 d3 mutation has on affinity for this fragment. However, the most striking difference between this double revertant and the E270K single-site revertant is the nearly 30-fold improvement in affinity for LRP1 CR3-5. Therefore, the K256A mutation in MegaRAP1 d3 is a crucial determinant of the ability of this variant to discriminate between the two receptor fragments, exerting its effect by negatively impacting affinity for LRP1 CR3-5 while at the same time improving affinity for LRP2 CR89.

Of the RAP d3 forward mutants tested, only the combination of E251K, K256A and K270E resulted in measurable affinity for LRP2 CR89. The apparent dissociation constant for binding of this triple mutant to LRP2 CR89 was 114 nM, still relatively high compared to MegaRAP1 d3. This affinity difference would presumably close further with the addition of the H249Y mutation. Single-site RAP d3 mutants at 217, 249 and 251 had minimal effects on-binding LRP1 CR3-5 and did not bring affinity for LRP2 CR89 into the measurable range. The K270E mutation, either alone or in combination with E251K, K256A or both, failed to measurably bind LRP1 CR3-5. The significant negative impact of K256A or K270E on binding of RAP d3 to LRP1 have been previously reported in a study on loss-of-function RAP mutants (55). The results reported here are consistent with this work. Overall, the positive contributions of the mutations at 249, 251 and 256 in MegaRAP1 d3 toward binding of LRP2 CR89 and the negative contributions of mutations at 256 and 270 on binding to LRP1 CR3-5 seem to primarily account for the differences between MegaRAP1 d3 and wild-type RAP d3 in binding to the two receptor fragments.

Figure 6:
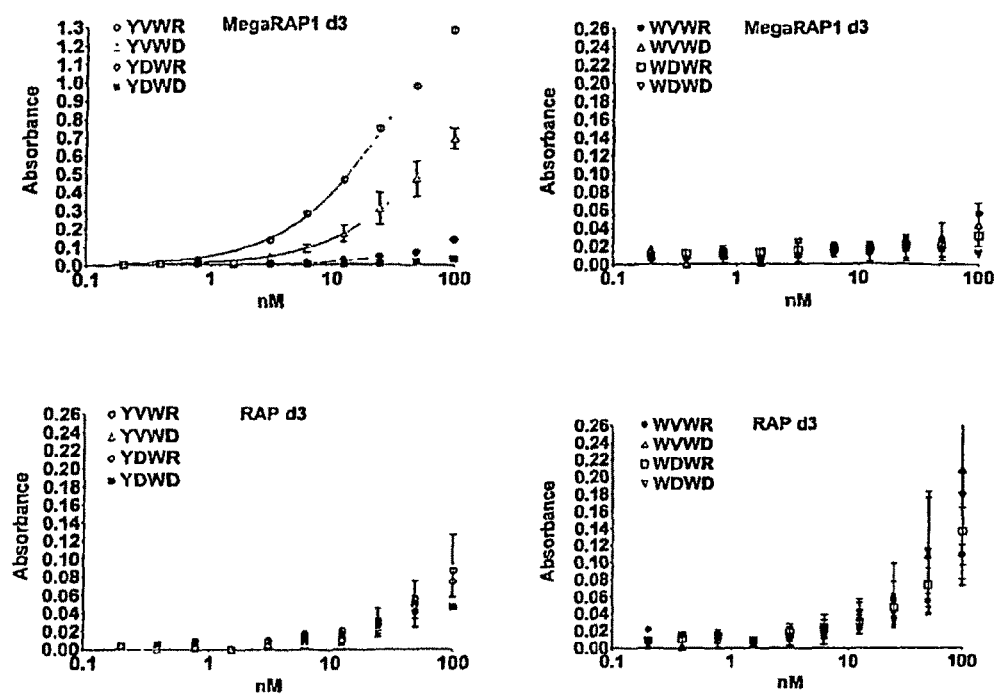
FIG. 6 shows binding of MegaRAP1 d3 and RAP d3 to LRP2 CR89 variants. Abbreviations used in the figure: LRP2 CR89Y1042W (WVWR), LRP2 CR89V1047D (YDWR), LRP2 CR89R1088D (YVWD), LRP2 CR89V1047D R1088D (YDWD), LRP2 CR89Y1042W V1047D R1088D (WDWD), LRP2 CR89 Y1042W V1047D (WDWR), LRP2 CR89Y1042W R1088D (WVWD).
Figure 7:
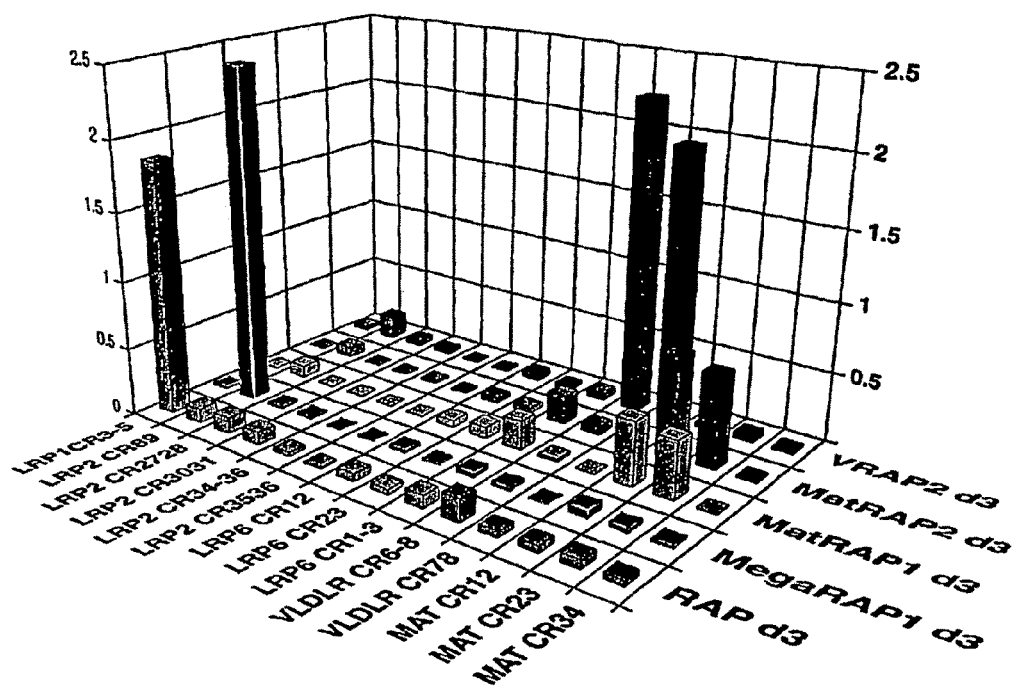
FIG. 7 shows binding of RAP d3 variants to CR pairs. RAP d3, MegaRAP1 d3, VRAP2 d3, MatRAP1d3 and MatRAP2 d3 were each incubated at 80 nM concentrations with LRP1 CR3-5, LRP6 CR12, LRP6 CR23, LRP6 CR1-3, LRP2 CR89, LRP2 CR2728, LRP2 CR3031, LRP2 CR3435, LRP2 CR34-36, VLDLR CR78, VLDLR CR6-8, MAT CR12, MAT CR23 and MAT CR34. Samples were tested twice, in duplicate, and values combined. Means and standard deviations were then calculated. Blank values obtained from wells incubated in the absence of ligand were used to correct absorbance data. Coefficients of variance (CV) did not exceed 20% (mean of 6%) for any condition tested and are not shown.

One premise of this work was that amino acids at A, C, A' and C' within the calcium-binding loops of a CR pair were key determinants of binding affinity for RAP and would be similarly important for binding of RAP variants. To test this idea, mutant LRP2 CR89 were prepared in which the native, non-canonical residues at these positions were sequentially substituted with the non-native, canonical residues. As defined above, the A, C, A', C' string for LRP2 CR89 is YVWR. Mutants included LRP2 CR89Y1042W (WVWR), LRP2 CR89V1047D (YDWR), LRP2 CR89R1088D (YVWD), LRP2 CR89V1047D R1088D (YDWD), LRP2 CR89 Y1042W V1047D R1088D (WDWD), LRP2 CR89Y1042W V1047D (WDWR), LRP2 CR89Y1042W R1088D (WVWD). Binding to both RAP d3 and MegaRAP1 d3 were measured for each LRP2 CR89 mutant by solid-phase assay. Only the YVWD mutant retained significant binding to MegaRAP1 d3, with an approximate 2-fold loss of affinity relative to LRP2 CR89 (FIG. 6 and FIG. 17). The position C mutant, with the tetrameric sequence string of YDWR failed to bind measurably to MegaRAP1 d3 as did all other single mutations or combinations of mutations involving either A or C. Interestingly, the nominally conservative Y1042W mutation alone was sufficient to prevent binding of MegaRAP1 d3. The A' position in LRP2 CR89 is a tryptophan, the canonical residue for wild-type RAP d3 binding, and was not mutated in our studies. While substitution of amino acids at A, C and C' had a strong negative impact on binding of MegaRAP1 d3, these substitutions did not greatly improve affinity for RAP d3, despite substitution with amino acids preferred by RAP d3 in other CR pairs such as LRP1 CR56. We did see a small increase in binding of RAP d3 to the WVWD and WDWD combinations at A, C, A' and C'. These results suggest that while some amino acids in the calcium-binding loop are important for defining RAP and RAPv2A binding behavior, they are not sufficient to do so alone.

As a test of the generality of the screening method phage library panning experiments were performed on additional CR proteins. Isolated variant sequences are depicted in FIG. 18 and FIG. 8. Initially VLDLR CR6-8, constituting the last three CR domains of human VLDLR, was used as a substrate for panning using a phage-display library encoding mutants of RAP d3 alone. Following five rounds of panning, five of eight randomly chosen clones had the same mutation set: R205S, E251R, K256L, K270E, R296L, G313D. This sequence variant, VRAP1) d3 was expressed for solid-phase binding studies. Binding of VRAP1d3, MegaRAP1d3 and RAP d3 to LRP1 CR3-5, LRP2 CR89 and VLDLR CR6-8 was compared. A similar variant sequence, E251T, Y256I, K270E, R296L, was selected on VLDLR CR78. We also panned on three CR pairs from human matriptase, MAT CR12, MAT CR23 and MAT CR34 using the same d3 library. Phage libraries were resolved to predominant sequences by the sixth round of panning on the matriptase pairs. The predominant sequence selected on MAT CR23 was E251G, K256R, K270W. This variant was name MatRAP1 (RAP vMA). The predominant sequence selected on MAT CR34 was S232P, E239G, E246G, E251L, K256P, I266T, A267V, H268R, K270P, H273Y, R287H, H290Y, K298R, S312F. This variant was named MatRAP2 (RAP vMB). Panning experiments were also performed on the CR pair from FDC-8D6 antigen. The predominant variant selected was K256S, K270S, L271M, D279Y, V283M, K305T, K306M. This variant was named 320RAP1.

To test the extent to which the length of a RAP d3 sequence variant could be minimized, sequentially-truncated sections of MatRAP1 were prepared by PCR, expressed, purified and tested for binding as described above (FIG. 9). Removal of 10 amino acids slightly diminished affinity but removal of 31 and 42 amino acids from the N-terminus resulted in incremental increases in affinity up to 3-fold over the full-length d3 variant. Further N-terminal truncations, beginning with an additional 10 amino acids (52 total), resulted in a complete loss of binding. Subsequent C-terminal truncation of the best N-terminally truncated variant (MatRAP1 N-42) resulted in further, significant increases in binding affinity, starting with a 2-fold increase (6-fold from full-length) with removal of the C-terminal linker and affinity tag and then a 4-fold increase (12-fold over full-length) after removal of an additional 6 amino acids from the C-terminus. Further C-terminal truncations, beginning with an additional 19 amino acids, resulted in a complete loss of binding. The best truncated variant consisted of amino acids 243-313 (71 amino acids). To test the generality of this modification in improving affinity, we made identical truncations to 320RAP1. The resulting truncated form of this variant bound with a 3.5-fold improvement in affinity for the FDC-8D6 antigen pair as compared to the full-length variant (FIG. 10).

The apparent dissociation constant for binding of VRAP1d3 to VLDLR CR78 was determined to be 44-9 nM. We then compared binding of RAP d3, MegaRAP1 d3, VRAP1d3, MatRAP1d3 and MatRAP2 d3, each at a concentration of 80 nM, to fourteen CR pairs or triplets, including LRP1 CR3-5, LRP2 CR89, LRP2 CR2728, LRP2 CR3031, LRP2 CR34-36, LRP2 CR3536, VLDLR CR78, VLDLR CR6-8, LRP6 CR1-3, LRP6 CR12, LRP6 CR23, MAT CR12, MAT CR23 and MAT CR34 (FIG. 7). As before, RAP d3 only bound to LRP1 CR3-S. MegaRAP1d3 bound only to LRP2 CR89. VRAP1d3 bound to both VLDLR CR78 and VLDLR CR6-8, a triplet that includes the CR78 pair. MatRAP1 and MatRAP2 bound to both MAT CR12 and MAT CR23 but not appreciably to the other CR pairs.

In addition to panning on CR pairs and triplets, whole, CR pair-containing human proteins were used as targets for the RAP d3 variant phage panning procedure. These commercially-available proteins included the ectodomains of corin, LRP6, FDC-8D6 antigen and complement factor I. Panning was performed exactly as described for isolated CR pairs and triplets.

Example 2

Evaluation of RAP Variants or CR-Specific Antibody Using In Vitro and In Vivo Assays RAP variants or CR-specific antibodies are useful as therapeutic agents or to transport therapeutic or diagnostic agents across the blood-brain barrier or other types of tissue membranes to treat a variety of human conditions or disorders. In vitro activity or transport assays and in vivo measurement of RAP variant activity or distribution are examples of methods to assess the efficacy of RAP variants. Examples of such assays are disclosed below.

Preparation of CR-Specific Antibodies Binding to any of the Repeated CR domains described herein may be carried out using any means known in the art, and antibodies thus prepared may be screened for relatively higher binding to the desired CR pairs compared to other CR pairs. Antibodies thus selected will then be tested for binding to the desired CR-containing protein compared to one or more other CR-containing proteins in the family. Antibodies that meet these criteria can then be assayed, alone or conjugated to other active agents, for ability to target to desired tissues, alteration of receptor activity, and/or prevention or treatment of disease in exemplary assays as described below.

In Vivo Anti-Tumor Assays Using Matriptase-Selective RAP Variants—

To assess the antagonistic effect that matriptase-selective RAP variants or a CR-specific antibody have on tumor formation and progression, at least two in vivo models can be used. The first model utilizes nude mice innoculated with human tumor cell lines and is well-described in the literature. This system is useful for testing the ability of RAP variants or a CR-specific antibody to slow tumor progression. The second model utilizes a transgenic mouse model that overexpresses mouse matriptase under control of the keratin promoter, restricting expression to epithelial tissues. This model has also been described previously (List et al., Genes and Development, 2005, 19:1934-1950).

In Vitro Transport Assays of LRP2 and VLDLR-Selective RAP Using Recombinant MDCK Cells—

To assess the transport of RAP variants or CR-specific antibodies across cell membranes, in vitro transport assays are used. Stably-transfected MDCK cells expressing a mini-receptor of human LRP2 (LB2) and full-length human VLDLR are cultured in vitro. These cells are plated on Transwell polyacetate membrane inserts (Costar, Cambridge, Mass.) having a uniform pore size of 0.4 µm. Cells are seeded at a density of $2\times10^5$/ml and cultured in DMEM supplemented with 10% FBS. Medium is changed every three days. The cells are maintained in a 5% $CO_2$ incubator at 37° C. Transcytosis studies are performed in triplicate. Twenty minutes before the transport assay, the Transwell insert is equilibrated in transport buffer (Hank's balanced salt solution with 25 mM HEPES and 0.1% albumin) at 37° C. Transport is initiated by addition of $^{125}$I-RAP variant (1 µCi/ml) and $^{99m}$Tc-albumin (2 µCi/ml) to the upper or lower chambers. The plate is maintained at 37° C. with gentle agitation at 130 rpm during the entire procedure. At 5, 10, 15, 20, 30, 40, 50, and 60 minutes following addition of labeled protein, a 10 µl of sample is collected from the lower chamber and upper chambers of each well. At 60 minutes, the entire solution in the upper and lower chambers is transferred to separate test tubes on ice. The total radioactivity from $^{125}$I and $^{99m}$Tc is measured simultaneously in a γ-counter with a dual-channel program. The amount of intact RAP and albumin after transport is measured by acid precipitation and comparison of radioactive counts in the soluble and insoluble fractions of the sample.

Measurement of Tissue Distribution of RAP and RAP Variants in Mice—

To determine the ability of the RAP variants or CR-specific antibodies to transcytose tissue in vivo, the tissue distribution of RAP variants or CR-specific antibodies in tissue samples from treated animals is measured.

Male CD1 mice, weighing 25-35 grams (Charles River Laboratories), are anesthetized by intraperitoneal injection of pentobarbital 30 mg/kg and ketamine 30 mg/kg. Each mouse receives a bolus injection of $^{125}$I-RAP or RAP variant or CR-specific antibody and $^{131}$I-albumin as a vascular space marker (1 µCi of each labeled protein in lactated Ringers with 1% albumin) through the left jugular vein. At designated intervals (1-60 minutes after injection), blood is collected by cutting the right common carotid artery, and the mouse was decapitated. Brain and peripheral tissue samples are collected and assayed for weight and radioactivity. Volumes of distribution are calculated as using techniques well-known in the art. A decrease in radioactivity in tissue samples indicates that the RAP variant is competing for binding with the labeled wild-type RAP and is internalized instead of wild-type RAP.

Measurement of the Anti-Proliferative Effects of LRP6-Selective RAP Variants in Cell Proliferation Assays—

LRP6 overexpression has been correlated with increased tumorigenicity. RAP protein is a potent binder of LRP6, and variants of RAP may be useful to inhibit RAP/LRP6 interaction, or to deliver drug to LRP6 expressing cells. To examine the ability of RAP variants to modulate LRP6-mediated cell-proliferation, cell proliferation assays are performed.

HT1080 cells transfected with an LRP6 expression construct (L1, (2004) Oncogene 23, 9129-9135) seeded into 6-well plates ($5\times10^4$ cells per well). RAP variants and other test compounds are included in the growth medium at 5-50 nM. Medium is changed and cells harvested each day. Cells are counted and scored for viability using a Vi-Cell cell analysis system. Doubling times under the various test conditions are obtained by non-linear regression using GraphPad Prism software. A decrease in cell proliferation in the presence of RAP variants indicates the RAP variants are effective inhibitors of LRP6 induced cell proliferation. Similar assays can be carried out with CR-specific antibodies.

Measurement of the Anti-Proliferative Effects of LRP6-Selective RAP Variants in Soft Agar Colony Assays—

HT1080 cells transfected with an LRP6 expression construct are cultured in 6-well plates coated with an agar layer (DMEM medium with 0.5% agar and 5% FBS). Cell are seeded within a second layer containing $2\times10^3$ cells in DMEM with 0.33% agar and 5% FBS. The agar and cells are overlaid with medium to prevent drying. Test compounds, including RAP variants, are added directly to the medium and allowed to incubate with the cells. Medium is exchanged every three days. Triplicate wells are prepared for each cell line. After 3 weeks of incubation, colonies larger than 0.1 mm in diameter are scored. A decrease in colony formation in the presence of RAP variants indicates that RAP variants are effective inhibitors of LRP6 induced cell proliferation.

Measurement of the Anti-Tumor Effects of LRP6-Selective, Matriptase-Selective and FDC-8D6-Selective RAP Variants in a Nude Mouse Model of Tumorigenicity—

To examine the effects of RAP variants on LRP6, matriptase or FDC-8D6 antigen inhibition in vivo, experimental animal models of tumorigenicity are used. Similar assays can be carried out with CR-specific antibodies.

Female athymic nude mice (4-5 weeks old) (Harlan Sprague-Dawley) (Indianapolis, Ind.). are injected subcutaneously in the flank (9) with HT1080 cells transfected with an LRP6 expression construct ($6\times10^6$ cells in 200 µL of serum free DMEM with 50% Matrigel matrix (BD Biosciences)), CWR22R prostate carcinoma cells (matriptase)(67) or L3055 Burkitt's lymphoma cells (FDC-8D6 antigen)(36). Selective RAP variants, or vehicle alone, are administered by tail vein injection in sterile PBS every other day to mice receiving tumor cells or control animals. Tumor size are measured every 7 days, and tumor volumes calculated using width (a) and length (b) measurements ($a2\times b/2$, where $a<b$).

Measurement of the Effects of RAP Variants on LRP5-Dependent Wnt Signaling in Cultured Osteoblasts—

Wnt signaling through LRP5 has been demonstrated to increase osteoblast differentiation, inhibit osteoclast activity and enhance bone deposition (Westendorf, (2004) Gene 341, 19-39; Zhang, et al., (2004) Mol Cell Biol 24, 4677-4684; Mizuguchi, et al., (2004) J Hum Genet. 49, 80-86). Because RAP binds to CR in LRP5, RAP variants may be useful to modulate Wnt signaling through the receptor. The ability of RAP variants to modulate Wnt signaling is measured using cultured osteoblasts. Similar assays can be carried out with CR-specific antibodies.

Osteoblast cell lines MG63 expresses large amounts of LRP1 and no VLDLR. SAOS-2 cells express large amounts of VLDLR and almost no LRP1 (American Type Culture Collection (ATCC) Accession #HTB-85. MG63 and SAOS-2 cells are grown in DMEM supplemented with 10% FBS at 37° C. in 10% CO2. Media are supplemented with Wnt7a to induce the Wnt signaling pathway, along with buffer, DKK-1, Mesd, RAP or RAP variants. After washing in ice-cold PBS, cells are collected and homogenized in a glass Dounce homogenizer with 100 mM Tris-HCl, pH 7.4, 140 mM NaCl, 2 mM DTT, 2 mM PMSF, and 1× Complete™ protease inhibitors (500 µl/well). The homogenate is centrifuged for 10 minutes at 500×g, and the supernatant is further centrifuged at 100,000×g at 4° C. for 90 minutes. The β-catenin levels are measured in the clarified supernatant by Western blotting using β-catenin-specific antibody from Cell Signaling Technology. The immunoreactive proteins are detected using the ECL system. Alternatively, cells are first transfected with 0.5 µg of the TOP-FLASH TCF luciferase construct (Upstate Biotechnology) along with 0.5 µg of β-catenin-expressing vector, 0.5 µg of Wnt1-expressing vector, or empty pcDNA3 vector. A β-galactosidase-expressing vector (Promega, Madison, Wis.) is included as an internal control for transfection efficiency. After 48 hours, media is changed and either buffer, DKK-1, Mesd, RAP or RAP variants is added. After incubating for an addition 6 hours, cells are lysed and both luciferase and β-galactosidase activities determined with enzyme assay kits (Promega). The luciferase activity is determined with a luminometer using the Dual Luciferase Assay system (Promega). Luciferase activity is normalized to the activity of the β-galactosidase.

Example 3

Production and Characterization of a RAP-GDNF Fusion as a Potential Therapeutic Agent Production of RAP-GDNF in CHO Cells—

A recombinant CHO cell line expressing RAP-GDNF was maintained in UltraCHO medium with 2.5% fetal bovine serum, 400 µg/mL G418, 2 mM glutamine, penicillin and streptomycin. For medium-scale culture with microcarriers in 500 mL spinner flask, 4000 cells/mL were added to 0.3 g of Cytopore beads in solution into 150 mL of JRH 302 medium, 2.5% fetal bovine serum, 400 µg/mL G418, 2 mM glutamine, penicillin and streptomycin. The serum concentration was progressively decreased to zero and RAP-GDNF production followed for 2 weeks. The medium was changed daily, cell growth was evaluated by measuring glucose consumption (YSI 2700 analyzer) and RAP-GDNF production was quantified by functional ELISA. For adaptation in suspension culture without serum, 40,000 cells/mL were seeded into 20 mL of JRH 302 medium, 2.5% fetal bovine serum, 400 µg/mL G418, 2 mM glutamine, penicillin and streptomycin, in 12 L shaker. When the viability was stable, the serum concentration was progressively decreased to zero and the cells were passaged at a density of 2000 cells/mL. Before decreasing serum concentration and when the culture was serum free, a batch culture was performed with the aim of defining the characteristics of RAP-GDNF production and to select the best producer clone. Cell density, viability and RAP-GDNF production were monitored for 4 days, without changing the media.

Functional ELISA—

GFRα-1 (R&D Systems) was immobilized in a 96-well micro-titer plate (Nunc MaxiSorp) by coating each well with 1 µg of receptor in 100 µL of 20 mM carbonate buffer (pH 8.2) at 4° C. overnight. Except for the coating step, all procedures were performed at room temperature. After each step, wells were washed three times with DPBS containing 0.1% Tween 20. The ELISA plates were incubated for 2 hours with 20 µL of blocking buffer (Block & Sample Buffer, Promega). RAP-GDNF fusions and rhGDNF standard (Promega) were diluted in the blocking buffer, and then added to each well. After incubating for 2 hours, the unbound material was removed by washing and bound protein detected with anti-GDNF mAb diluted at 1:2,000 in blocking buffer. After an one hour incubation, immune complexes were detected by adding secondary antibody (anti-mouse IgG (H+L), HRP conjugate, Promega), for 1 hour, followed by colorimetric assay using TMB one solution (TMB Stabilized Substrate for Horseradish Peroxidase, Promega). Hydrochoric acid was used to halt color development. The optical density (OD) of each well was measured at 450 nm within 30 minutes of stopping the reaction (SPECTRAmax, Molecular Devices). This method allows for the accurate quantitation of RAP-GDNF in complex mixtures.

Solid-Phase Binding Assays—

Microtiter plates were coated with GDNF or RAP-GDNF in 50 mM sodium carbonate, pH 9.6. The plates were then blocked for 1 hour at room temperature with blocking buffer (Promega) and incubated with serial dilutions of GFRα-1 (0-10 nM) in the presence or the absence of 1 µM RET (2 hours, ambient temperature). Complexes were identified by probing with an anti-GDNF monoclonal antibody (B8, Santa Cruz Biotechriology) and then with anti-mouse P conjugate (Bio-Rad). After adding TMB solution (Bio-Rad), the color development was stopped with HCl and the OD 450 nm was measured using a plate reader. Between steps, the plates were washed three times with DPBS containing 0.1% Tween 20. This method provides a method for quantitating the affinity of RAP-GDNF for GFRα.

Tyrosine Phosphorylation Assays—

Prior to the beginning of the experiment (48 hours), flasks were seeded with SK-N-SH cells (ATCC HTB-11). Cells were treated with 1 µM retinoic acid (Sigma) to increase the level of RET expression 12 hours prior to addition of RAP-GDNF or GDNF. Cells were incubated for 1 hour at 37° C. in serum-free medium (MEM, 2 mM glutamine, 1 mg/mL BSA). Then, cells were incubated with or without GDNF standard (10 ng/mL) or RAP-GDNF (ng/mL) and soluble GFRα-1 (1 ng/mL) for 15 minutes at 37° C. Cells were then washed with ice-cold PBS, incubated for 10 minutes on ice with ice-cold lysis buffer (150 mM NaCl, 1% IGEPAL, 0.01 M vanadate, 0.5% deoxycholate, 50 mM Tris HCl pH 8.0, Complete™ protease inhibitor cocktail) and harvested by scraping. The cell lysate was centrifuged for 15 minutes at 3,000 RPM at 4° C. Clear lysates were transferred into fresh tubes. Anti-GDNF, GFRα-1, RET or phospho-tyrosine antibodies were added to the lysates and incubated for 2 hours at 4° C. with shaking. Protein G sepharose (Fast Flow, Amersham Biosciences) was then added to the tubes and incubated 2 hours at 4° C. with shaking. Beads were then washed twice with lysis buffer and once with PBS. The immunoprecipitated proteins were released by boiling the beads in SDS sample buffer (NuPAGE® LDS Sample Buffer, Invitrogen) for 5 minutes, separated on NuPAGE® Novex 4-12% Bis-Tris Gels (Invitrogen) and probed with either anti-RET (C-19 or H-300, Santa Cruz Biotechnology), anti-phosphotyrosine (recombinant 10, Upstate), anti-phospho-RET (Santa Cruz Biotechnology), anti-GDNF (B8, Santa Cruz Biotechnology), anti-GDNF (D20, Santa Cruz Biotechnology), anti-GFRα1 (R&D Systems) or anti-RAP (polyclonal, BioMarin). Alternatively, immobilized anti-RAP (previously washed twice and two fold diluted with lysis buffer) was added to cell lysate. The mixture was incubated for 3 hours at 4° C. with shaking. Anti-RAP beads were then washed twice with lysis buffer and once with PBS. The immunoprecipitated proteins were released by boiling the beads in SDS sample buffer (NuPAGE® LDS Sample Buffer, Invitrogen) for 5 minutes, separated on a NuPAGE® Novex 4-12% Bis-Tris Gel (Invitrogen) and probed with similar antibodies. This method measures the functionality of RAP-GDNF with respect to receptor tyrosine kinase activation.

Cell Differentiation Assays—

PC-12 cells were maintained in F-12 medium (ATCC) with 10% fetal horse serum, 2.5% fetal bovine serum, 2 mM glutamine, penicillin and streptomycin. For neurite outgrowth experiments, cells were plated on to 1 mm coverslips that had been coated for 1 hour in 60 µL of 10 µg/mL EHS laminin (Sigma) in F-12 medium with 10% fetal horse serum, 2.5% fetal bovine serum, 2 mM glutamine, 10 μg/mL GFRα-Fc chimera (R&D Systems), penicillin and streptomycin, at the bottom of 24-well plates (the coating solution was removed before the cells were added). Cells were then incubated for 3-4 days in the presence or the absence of different concentrations of GDNF or RAP-GDNF (10, 100, 1000 ng/mL), 3M sodium chlorate (Sigma), heparinase III or chondroitinase ABC (Sigma). Qualitative responses were noted by evaluating the level of differentiation as a function of the number and size of the neurites.

Results

Western blotting results indicated that RAP-GDNF was secreted as a disulfide-linked homodimer, like GDNF (FIG. 11). Binding experiments demonstrated that the RAP-GDNF/GFRα-1 complex had a dissociation constant of approximately 5 ng/mL, or 5 μM (molecular weight of RAP-GDNF is approximately 120 kD, FIG. 12). This value is close to that reported for the GDNF/GFRα-1 complex in the literature.

Tyrosine Phosphorylation Assays—

In vivo, GDNF homodimer binds to its receptor GFRα-1 (probably also a dimer), then the GDNF-GFRα-1 complex binds to the Ret protein, which dimerizes. The dimerization of Ret causes the autophosphorylation of tyrosine 1062. Since RAP-GDNF was shown to bind to GFRα-1, the next step was to demonstrate that the RAP-GDNF fusion protein was also able to bind Ret and induce autophosphorylation. The human neuroblastoma line SK-N-SH was exposed to different concentrations of RAP-GDNF or GDNF in combination with GFRα-1, and the level of Ret phosphorylation was determined by immunoprecipitation. A series of positive and negative controls were tested to ensure that the experimental conditions allowed detection of Ret phosphorylation. Immunoprecipitation (FIG. 13) showed the phosphorylation of Ret only occurred when GDNF and GFRα-1 were been added together; the activation of Ret was evidenced by a phosphorylated protein of about 160 Da, the expected size for Ret, that co-stained on blots with an anti-Ret antibody. Different concentrations of standard GDNF were tested to ascertain whether this assay could be quantitative as well as qualitative (FIG. 13). The intensity of this band increased with the quantity of GDNF added. This experiment shows that the immunoprecipitation assay allows both qualitative and quantitative studies on GDNF-induced phosphorylated of Ret.

Immunoprecipitation of the Ternary Complex—

The autophosphorylation of Ret occurs when the GDNF/GFRα-1 complex binds to Ret. If RAP-GDNF functions similarly, a ternary complex involving RAP-GDNF/GFRα-1 and Ret should be detectable. FIG. 14 shows the results from experiments designed to detect this complex. Using an anti-RAP antibody-agarose conjugate, we were able to purify the three components of the complex containing activated Ret. These results are consistent with the direct interaction of these proteins. Furthermore, the phosphorylation of Ret shown here is consistent with activation by RAP-GDNF.

Differentiation Assay—

Previous results had shown that the RAP-GDNF fusion protein was able to bind to its receptor and to activate Ret. Further downstream events can be confirmed through the induction of cell differentiation. Increasing concentrations of GDNF or RAP-GDNF were added to PC12 cells. Since these cells adhere poorly to plastic and tend to growth in large clusters, coverslips previously coated with laminin and GFRα-1 were used. The level of differentiation was evaluated by the presence, the quantity and the size of neurites. RAP-GDNF, like GDNF, was able to induce neurite outgrowth in PC12 cells. FIGS. 15A and 15B illustrate the differentiation resulting from the addition of RAP-GDNF. The level of differentiation was observed to be a function of the quantity of GDNF or RAP-GDNF added. The apparent level of induced differentiation was the same with same approximate molar concentrations of GDNF and RAP-GDNF, indicating that the RAP-GDNF fusion retained substantially the same potency as GDNF alone.

CONCLUSION

To resolve the inability of GDNF to cross the blood-brain barrier, GDNF was fused to a RAP, a protein previously shown to cross the blood-brain barrier. RAP-GDNF was produced in CHO cells and Western blot analysis confirmed the secretion of a disulfide-linked homodimer of approximately 120 kD. Further analysis demonstrated that RAP-GDNF bound to GFRα-1 with the same affinity (Kd) as GDNF; that the RAP-GDNF/GFRα complex bound and activated Ret; and that RAP-GDNF induced neurite outgrowth in PC12 cells in culture. This work demonstrates that RAP or receptor-selective RAP variant-GDNF fusions are likely to be potent effectors of physiological processes dependent on GDNF in vivo.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

REFERENCES

1. MAY, P., BOCK, H. H., AND HERZ, J. (2003) *SCI STKE* 2003, PE12.
2. HERZ, J., AND WILLNOW, T. E. (1995) *ATHEROSCLEROSIS* 118 SUPPL, S37-41.
3. TAKAHASHI, S., SAKAI, J., FUJINO, T., MIYAMORI, I., AND YAMAMOTO, T. T. (2003) *MOL. CELL. BIOCHEM.* 248, 121-7.
4. HERZ, J., AND BOCK, H. H. (2002) *ANNU. REV. BIOCHEM.* 71, 405-34.
5. HAHN-DANTONA, E., RUIZ, J. F., BORNSTEIN, P., AND STRICKLAND, D. K. (2001) *J BIOL. CHEM.* 276, 15498-503.
6. NEELS, J. G., BOVENSCHEN, N., VAN ZONNEVELD, A. J., AND LENTING, P. J. (2000) *TRENDS CARDIOVASC MED* 10, 8-14.
7. MARTIN, S., VINCENT, J. P., AND MAZELLA, J. (2003) *J. NEUROSCI.* 23, 1198-205.
8. SCHNEIDER, W. J., AND NIMPF, J. (2003) *CELL MOL LIFE SCI* 60, 892-903.
9. LI, Y., LU, W., HE, X., SCHWARTZ, A. L., AND BU, G. (2004) *ONCOGENE* 23, 9129-35.

10. HOANG, B. H., KUBO, T., HEALEY, J. H., SOWERS, R., MAZZA, B., YANG, R., HUVOS, A. G., MEYERS, P. A., AND GORLICK, R. (2004) *INT. J. CANCER* 109, 106-11.
11. VERDAGUER, N., FITA, I., REITHMAYER, M., MOSER, R., AND BLAAS, D. (2004) *NAT STRUCT MOL BIOL* 11, 429-34.
12. PFISTERMUELLER, D. M., BLAAS, D., AND HODITS, R. A. (1996) *FEBS LETT.* 396, 14-20.
13. HOE, H. S., HARRIS, D. C., AND REBECK, G. W. (2005) *J. NEUROCHEM.* 93, 145-55.
14. QIU, Z., CRUTCHER, K. A., HYMAN, B. T., AND REBECK, G. W. (2003) *NEUROSCIENCE* 122, 291-303.
15. BASU, S., BINDER, R. J., RAMALINGAM, T., AND SRIVASTAVA, P. K. (2001) *IMMUNITY* 14, 303-13.
16. BENCHENANE, K., BEREZOWSKI, V., ALI, C., FERNANDEZ-MONREAL, M., LOPEZ-ATALAYA, J. P., BRILLAULT, J., CHUQUET, J., NOUVELOT, A., MACKENZIE, E. T., BU, G., CECCHELLI, R., TOUZANI, O., AND VIVIEN, D. (2005) *CIRCULATION* 111, 2241-9.
17. DEHOUCK, B., FENART, L., DEHOUCK, M. P., PIERCE, A., TORPIER, G., AND CECCHELLI, R. (1997) *J. CELL BIOL.* 138, 877-89.
18. FILLEBEEN, C., DESCAMPS, L., DEHOUCK, M. P., FENART, L., BENAISSA, M., SPIK, G., CECCHELLI, R., AND PIERCE, A. (1999) *J. BIOL. CHEM.* 274, 7011-7.
19. PAN, W., KASTIN, A. J., ZANKEL, T. C., VAN KERKHOF, P., TERASAKI, T., AND BU, G. (2004) *J. CELL SCI. PT.*
20. MOESTRUP, S. K., AND VERROUST, P. J. (2001) *ANNU REV NUTR* 21, 407-28.
21. MARINO, M., ZHENG, G., CHIOVATO, L., PINCHERA, A., BROWN, D., ANDREWS, D., AND MCCLUSKEY, R. T. (2000) *J. BIOL. CHEM.* 275, 7125-37.
22. DEANE, R., WU, Z., SAGARE, A., DAVIS, J., DU YAN, S., HAMM, K., XU, F., PARISI, M., LARUE, B., HU, H. W., SPIJKERS, P., GUO, H., SONG, X., LENTING, P. J., VAN NOSTRAND, W. E., AND ZLOKOVIC, B. V. (2004) *NEURON* 43, 333-44.
23. MIZUGUCHI, T., FURUTA, I., WATANABE, Y., TSUKAMOTO, K., TOMITA, H., TSUJIHATA, M., OHTA, T., KISHINO, T., MATSUMOTO, N., MINAKAMI, H., NIKAWA, N., AND YOSH, K. (2004) *J HUM GENET* 49, 80-6.
24. BOUCHER, P., GOTTHARDT, M., LI, W. P., ANDERSON, R. G., AND HERZ, J. (2003) *SCIENCE* 300, 329-32.
25. TANIMOTO, H., SHIGEMASA, K., TIAN, X., GU, L., BEARD, J. B., SAWASAKI, T., AND O'BRIEN, T. J. (2005) *BR J CANCER* 92, 278-83.
26. KATAOKA, H., TANAKA, H., NAGAIKE, K., UCHIYAMA, S., AND ITOH, H. (2003) *HUM CELL* 16, 1-14.
27. JOHNSON, M. D., OBERST, M. D., LIN, C. Y., AND DICKSON, R. B. (2003) *EXPERT REV MOL DIAGN* 3, 331-8.
28. SANTIN, A. D., CANE, S., BELLONE, S., BIGNOTTI, E., PALMIERI, M., DE LAS CASAS, L. E., ANFOSSI, S., ROMAN, J. J., O'BRIEN, T., AND PECORELLI, S. (2003) *CANCER* 98, 1898-904.
29. OBERST, M., ANDERS, J., XIE, B., SINGH, B., OSSANDON, M., JOHNSON, M., DICKSON, R. B., AND LIN, C. Y. (2001) *AM J PATHOL* 158, 1301-11.
30. LEE, J. W., YONG SONG, S., CHOI, J. J., LEE, S. J., KIM, B. G., PARK, C. S., LEE, J. H., LIN, C. Y., DICKSON, R. B., AND BAE, D. S. (2005) *HUM PATHOL* 36, 626-33.
31. HOANG, C. D., D'CUNHA, J., KRATZKE, M. G., CASMEY, C. E., FRIZELLE, S. P., MADDAUS, M. A., AND KRATZKE, R. A. (2004) *CHEST* 125, 1843-52.
32. SANTIN, A. D., ZHAN, F., BELLONE, S., PALMIERI, M., CANE, S., BIGNOTTI, E., ANFOSSI, S., GOKDEN, M., DUNN, D., ROMAN, J. J., O'BRIEN, T. J., TIAN, E., CANNON, M. J., SHAUGHNESSY, J., JR., AND PECORELLI, S. (2004) *INT J CANCER* 112, 14-25.
33. OBERST, M. D., JOHNSON, M. D., DICKSON, R. B., LIN, C. Y., SINGH, B., STEWART, M., WILLIAMS, A., AL-NAFUSSI, A., SMYTH, J. F., GABRA, H., AND SELLAR, G. C. (2002) *CLIN CANCER RES* 8, 1101-7.
34. NAGAIKE, K., KOHAMA, K., UCHIYAMA, S., TANAKA, H., CHIJIIWA, K., ITOH, H., AND KATAOKA, H. (2004) *CANCER SCI* 95, 728-35.
35. SUZUKI, M., KOBAYASHI, H., KANAYAMA, N., SAGA, Y., LIN, C. Y., DICKSON, R. B., AND TERAO, T. (2004) *J BIOL CHEM* 279, 14899-908.
36. LI, L., YOON, S. O., FU, D. D., ZHANG, X., AND CHOI, Y. S. (2004) *BLOOD* 104, 815-21.
37. LI, L., ZHANG, X., KOVACIC, S., LONG, A. J., BOURQUE, K., WOOD, C. R., AND CHOI, Y. S. (2000) *J. EXP. MED.* 191, 1077-84.
38. POSTINA, R., SCHROEDER, A., DEWACHTER, I., BOHL, J., SCHMITT, U., KOJRO, E., PRINZEN, C., ENDRES, K., HIEMKE, C., BLESSING, M., FLAMEZ, P., DEQUENNE, A., GODAUX, E., VAN LEUVEN, F., AND FAHRENHOLZ, F. (2004) *J CLIN. INVEST.* 113, 1456-64.
39. POLLACK, A. (2005) *NY TIMES (PRINT)*, C1, C2.
40. IRIE, S., AND TAVASSOLI, M. (1991) *CELL BIOL REV* 25, 317-33, 340-1.
41. BICKEL, U., YOSHIKAWA, T., AND PARDRIDGE, W. M. (2001) *ADV DRUG DELIV REV* 46, 247-79.
42. TSUZUKI, S., MURAI, N., MIYAKE, Y., INOUYE, K., HIRAYASU, H., IWANAGA, T., AND FUSHIKI, T. (2005) *BIOCHEM J* 388, 679-87.
43. OBERST, M. D., WILLIAMS, C. A., DICKSON, R. B., JOHNSON, M. D., AND LIN, C. Y. (2003) *J BIOL CHEM* 278, 26773-9.
44. HUNG, R. J., HSU IA, W., DREILING, J. L., LEE, M. J., WILLIAMS, C. A., OBERST, M. D., DICKSON, R. B., AND LIN, C. Y. (2004) *AM J PHYSIOL CELL PHYSIOL* 286, C1159-69.
45. SIMONOVIC, M., DOLMER, K., HUANG, W., STRICKLAND, D. K., VOLZ, K., AND GETTINS, P. G. (2001) BIOCHEMISTRY 40, 15127-34.
46. THOMPSON, J. D., HIGGINS, D. G., AND GIBSON, T. J. (1994) *NUCLEIC ACIDS RES.* 22, 4673-80.
47. RUDENKO, G., HENRY, L., HENDERSON, K., ICHTCHENKO, K., BROWN, M. S., GOLDSTEIN, J. L., AND DEISENHOFER, J. (2002) *SCIENCE* 298, 2353-8.
48. FISHER, C., BEGLOVA, N., AND BLACKLOW, S. C. (2006) *MOL CELL* 22, 277-83.
49. PRINCE, W. S., MCCORMICK, L. M., WENDT, D. J., FITZPATRICK, P. A., SCHWARTZ, K. L., AGUILERA, A. I., KOPPAKA, V., CHRISTIANSON, T. M., VELLARD, M. C., PAVLOFF, N., LEMONTT, J. F., QIN, M., STARR, C. M., BU, G., AND ZANKEL, T. C. (2004) *J. BIOL. CHEM.* 279, 35037-46.
50. WANG, Q. Y., DOLMER, K., HUANG, W., GETTINS, P. G., AND RONG, L. (2001) *J. VIROL.* 75, 2051-8.

51. HUANG, W., DOLMER, K., AND GETTINS, P. G. (1999) *J. BIOL. CHEM.* 274, 14130-6.
52. DOLMER, K., HUANG, W., AND GETTINS, P. G. (2000) *J. BIOL. CHEM.* 275, 3264-9.
53. DOLMER, K., HUANG, W., AND GETTINS, P. G. (1998) *BIOCHEMISTRY* 37, 17016-23.
54. VASH, B., PHUNG, N., ZEIN, S., AND DECAMP, D. (1998) *BLOOD* 92, 3277-85.
55. MIGLIORINI, M. M., BEHRE, E. H., BREW, S., INGHAM, K. C., AND STRICKLAND, D. K. (2003) *J BIOL. CHEM.* 278, 17986-92.
56. ANDERSEN, O. M., CHRISTENSEN, L. L., CHRISTENSEN, P. A., SORENSEN, E. S., JACOBSEN, C., MOESTRUP, S. K., ETZERODT, M., AND THOGERSEN, H. C. (2000) *J. BIOL. CHEM.* 275, 21017-24.
57. ANDERSEN, O. M., SCHWARZ, F. P., EISENSTEIN, E., JACOBSEN, C., MOESTRUP, S. K., ETZERODT, M., AND THOGERSEN, H. C. (2001) *BIOCHEMISTRY* 40, 15408-17.
58. OLSEN, B. R. (1999) *J. CELL BIOL.* 147, 909-12.
59. ANDERSEN, O. M., PETERSEN, H. H., JACOBSEN, C., MOESTRUP, S. K., ETZERODT, M., ANDREASEN, P. A., AND THOGERSEN, H. C. (2001) *BIOCHEM. J* 357, 289-96.
60. ANDERSEN, O. M., VORUM, H., HONORE, B., AND THOGERSEN, H. C. (2003) *BMC BIOCHEM* 4, 7.
61. HORN, I. R., VAN DEN BERG, B. M., VAN DER MEIJDEN, P. Z., PANNEKOEK, H., AND VAN ZONNEVELD, A. J. (1997) *J. BIOL. CHEM.* 272, 13608-13.
62. ANDERSEN, O. M., CHRISTENSEN, P. A., CHRISTENSEN, L. L., JACOBSEN, C., MOESTRUP, S. K., ETZERODT, M., AND THOGERSEN, H. C. (2000) *BIOCHEMISTRY* 39, 10627-33.
63. MEDVED, L. V., MIGLIORINI, M., MIHAILENKO, I., BARRIENTOS, L. G., LLINAS, M., AND STRICKLAND, D. K. (1999) *J. BIOL. CHEM.* 274, 717-27.
64. ZHENG, G., BACHINSKY, D. R., STAMENKOVIC, I., STRICKLAND, D. K., BROWN, D., ANDRES, G., AND MCCLUSKEY, R. T. (1994) *J. HISTOCHEM. CYTOCHEM.* 42, 531-42.
65. ORLANDO, R. A., EXNER, M., CZEKAY, R. P., YAMAZAKI, H., SAITO, A., ULLRICH, R., KERJASCHKI, D., AND FARQUHAR, M. G. (1997) *PROC. NATL. ACAD. SCI. U.S.A.* 94, 2368-73.
66. SIDHU, S. S., LOWMAN, H. B., CUNNINGHAM, B. C., AND WELLS, J. A. (2000) *METHODS ENZYMOL.* 328, 333-63.
67. GALKIN, A. V., MULLEN, L., FOX, W. D., BROWN, J., DUNCAN, D., MORENO, O., MADISON, E. L., AND AGUS, D. B. (2004) *PROSTATE* 61, 228-35.

What is claimed is:

1. An isolated polypeptide comprising an amino acid sequence variant of the mature alpha-2-macroglobulin/low density lipoprotein receptor-related protein-associated protein 1 (RAP) set out in SEQ ID NO: 121, wherein said RAP variant binds selectively to a pair of complement-type repeats within a protein selected from the group consisting of very low density lipoprotein receptor (VLDLR), matriptase and CD320, with an affinity that is at least 3-fold greater than the affinity of wild-type RAP for the same pair of complement-type repeats, wherein the RAP variant consists of
    (a) a polypeptide having an amino acid sequence at least 90% identical to SEQ ID NO: 121 and comprises mutations at at least two of the following positions: 251, 256, 257, 266 and 270, and optionally comprises a mutation at one or more of positions 175, 205, 213, 217, 226, 230, 232, 239, 246, 249, 251, 256, 257, 261, 266, 267, 268, 270, 273, 287, 290, 294, 296, 297, 298, 305, 312 or 313 of mature RAP; or
    (b) a polypeptide having an amino acid sequence at least 90% identical to amino acids 200-323 of SEQ ID NO: 121 and comprises mutations at at least two of the following positions: 251, 256, 257, 266 and 270, and optionally comprises a mutation at one or more of positions 205, 213, 217, 226, 230, 232, 239, 246, 249, 251, 256, 257, 261, 266, 267, 268, 270, 273, 287, 290, 294, 296, 297, 298, 305, 312, or 313 of mature RAP.

2. The polypeptide of claim 1 wherein said RAP variant lacks amino acids 1-143 and 320-323 of a mature RAP.

3. A RAP variant of claim 1 missing at least 200 and up to 243 amino acids from the N-terminus.

4. The RAP variant of claim 3 further missing up to 11 amino acids from the C-terminus.

5. The RAP variant of claim 4 missing at least 4 amino acids from the C-terminus.

6. The RAP variant of claim 1 comprising a continuous portion of mature RAP that is (a) at least 71 amino acids in length and (b) comprises amino acids 256-270.

7. The RAP variant of claim 1 comprising a continuous portion of RAP d3 that is (a) at least 71 amino acids in length and (b) comprises amino acids 256-270.

8. The polypeptide of claim 7 wherein the variant contains a mutation at any one of positions 251, 256, 257, 266, 270, 279, 280, 296 or 305 of RAP.

9. The polypeptide of claim 1 wherein the variant binds selectively to a matriptase protein.

10. The polypeptide of claim 9 wherein the variant contains a mutation at any one of positions 251, 256, 257, 266, 270, or 280 of RAP.

11. The polypeptide of any one of claims 9-10 wherein the variant comprises a mutation at position 251 of RAP.

12. The polypeptide of any one of claims 9-10 wherein the variant comprises a mutation at position 256 of RAP.

13. The polypeptide of any one of claims 9-10 wherein the variant comprises a mutation at position 14 of RAP.

14. The polypeptide of any one of claims 9-10 wherein the variant comprises a mutation at position 266 of RAP.

15. The polypeptide of any one of claims 9-10 wherein the variant comprises a mutation at position 270 of RAP.

16. The polypeptide of any one of claims 9-10 wherein the variant comprises a mutation at position 280 of RAP.

17. The polypeptide of claim 1 wherein the variant binds selectively to a VLDLR protein.

18. The polypeptide of claim 17 wherein the variant contains mutations at at least two positions selected from any one of positions 251, 256, 270 or 296 of RAP.

19. The polypeptide of any one of claims 17-18 wherein the variant comprises a mutation at position 251 of RAP.

20. The polypeptide of any one of claims 17-18 wherein the variant comprises a mutation at position 256 of RAP.

21. The polypeptide of any one of claims 17-18 wherein the variant comprises a mutation at position 270 of RAP.

22. The polypeptide of any one of claims 17-18 wherein the variant comprises a mutation at position 296 of RAP.

23. The polypeptide of claim 1 wherein the variant binds selectively to a CD320 protein.

24. The polypeptide of claim 23 wherein the variant contains a mutation at any one of positions 251, 256, 270, 279 or 305 of RAP.

25. The polypeptide of any one of claims 23-24 wherein the variant comprises a mutation at position 251 of RAP.

26. The polypeptide of any one of claims 23-24 wherein the variant comprises a mutation at position 256 of RAP.

27. The polypeptide of any one of claims 23-24 wherein the variant comprises a mutation at position 270 of RAP.

28. The polypeptide of any one of claims 23-24 wherein the variant comprises a mutation at position 279 of RAP.

29. The polypeptide of any one of claims 23-24 wherein the variant comprises a mutation at position 305 of RAP.

30. The polypeptide of claim 1 wherein the variant contains at least one additional mutation within positions 271-319 of RAP.

31. The polypeptide of claim 1 wherein the variant contains at least one mutation within positions 205-250 of RAP.

32. The polypeptide according to any one of claims 8, 9, 17, or 23, wherein any of the mutations comprises the replacement of an acidic amino acid with a basic amino acid.

33. The polypeptide of claim 32, wherein said acidic amino acid is selected from the group consisting of D and E.

34. A polypeptide of claim 32, wherein said basic amino acid is selected from the group consisting of K and R.

35. A polypeptide according to any one of claims 8, 9, 17, or 23, wherein any of the mutations comprises the replacement of a basic amino acid with an acidic amino acid.

36. A polypeptide of claim 35, wherein said basic amino acid is selected from the group consisting of K and R.

37. A polypeptide of claim 35, wherein said acidic amino acid is selected from the group consisting of D and E.

38. A polypeptide according to any one of claims 8, 9, 17, or 23, wherein any of the mutations comprises the replacement of an amino acid selected from the group consisting of A, C, D, E, G, I, K, L, M, N, P, Q, R, S, T, and V with an amino acid selected from the group consisting of F, Y, W, and H.

39. The polypeptide of any one of claims 1, 7, 8, 9, 17, or 23 that comprises a mutation at three or more of the following positions: 175, 205, 213, 217, 226, 230, 232, 239, 246, 249, 251, 256, 257, 261, 266, 267, 268, 270, 273, 287, 290, 294, 296, 297, 298, 305, 312, 313.

40. The polypeptide of any one of claims 1, 7, 8, 9, 17, or 23 that comprises a mutation at three or more of the following positions: 205, 217, 249, 251, 256, 257, 266, 270, 294, 296, 297, 305.

41. The polypeptide of any one of claims 1, 7, 8, 9, 17, or 23 that comprises three or more of the following mutations: R205S, S213T, E217K, L226M, H249Y, A230V, S232P, E239G, E246G, E251L, E251K, E251T, E251G, E251P, E251N, E251R, K256R, K256V, K256A, K256I, K256P, K256L, I266F, I266T, H257Y, Q261R, A267V, H268R, K270P, K270D, K270N, K270G, K270E, K270W, L271M, H273Y, D279Y, V283M, R287H, H290Y, H290L, E294V, R296L, T297I, K298R, K305T, K306M, S312F, G313D.

42. A polypeptide consisting of oligomeric combinations of polypeptides of any one of claims 1, 7, 8, 9, 17, or 23 with binding multivalent binding properties defined by each polypeptide of the combination.

43. A compound comprising the polypeptide according to any one of claims 1, 7, 8, 9, 17, or 23 conjugated to a diagnostic or therapeutic agent.

44. The compound of claim 43, wherein the polypeptide and diagnostic or therapeutic agent are linked through a linker.

45. The compound of claim 44, wherein said linker is a peptide linker.

46. The compound of claim 43, wherein the therapeutic agent is selected from the group consisting of a glial cell-derived neuronal growth factor (GDNF), brain-derived neuronal growth factor (BDNF), neuronal growth factor (NGF), disintegrin and metalloproteinase domain 10 (ADAM10), a chaperone protein for LRP5/6 (MESD), cancer chemotherapeutic agents, protease inhibitors, pro-apoptotic molecules, autoimmune antigens, lysosomal enzymes, nanoparticles, glycoconjugates and nucleic acids.

47. A pharmaceutical composition comprising a compound of claim 43 in a pharmaceutically acceptable carrier, diluent or excipient.

* * * * *